(12) United States Patent
Millar et al.

(10) Patent No.: US 7,833,942 B2
(45) Date of Patent: Nov. 16, 2010

(54) METHODS FOR SIMPLIFYING MICROBIAL NUCLEIC ACIDS BY CHEMICAL MODIFICATION OF CYTOSINES

(75) Inventors: Douglas Spencer Millar, Revesby (AU); George L. Gabor Miklos, Newport (AU)

(73) Assignee: Human Genetic Signatures Pty. Ltd., North Ryde (AU)

( * ) Notice: Subject to any disclaimer, the term of this patent is extended or adjusted under 35 U.S.C. 154(b) by 0 days.

(21) Appl. No.: 11/573,873

(22) PCT Filed: Dec. 5, 2005
(Under 37 CFR 1.47)

(86) PCT No.: PCT/AU2005/001840

§ 371 (c)(1),
(2), (4) Date: Jan. 15, 2008

(87) PCT Pub. No.: WO2006/058393

PCT Pub. Date: Jun. 8, 2006

(65) Prior Publication Data

US 2009/0042732 A1    Feb. 12, 2009

(30) Foreign Application Priority Data

Dec. 3, 2004    (AU) .............................. 2004906915

(51) Int. Cl.
*C40B 30/02* (2006.01)
*C40B 30/04* (2006.01)
*C07H 21/00* (2006.01)
*C12Q 1/68* (2006.01)
*C12Q 1/70* (2006.01)
*A61K 31/00* (2006.01)

(52) U.S. Cl. ................... 506/7; 506/8; 506/9; 536/25.3; 435/91.2; 435/5; 435/6

(58) Field of Classification Search ....................... None
See application file for complete search history.

(56) References Cited

U.S. PATENT DOCUMENTS

| 5,629,156 A | 5/1997 | Shah et al. |
| 5,750,338 A | 5/1998 | Collins et al. |
| 5,786,146 A | 7/1998 | Herman et al. |

(Continued)

FOREIGN PATENT DOCUMENTS

EP    1 130 113    9/2001

(Continued)

OTHER PUBLICATIONS

Zeschnigk (Nucleic Acids Research 2004 vol. 32 p. 1).*

(Continued)

*Primary Examiner*—Jeffrey S Lundgren
*Assistant Examiner*—Christian Boesen
(74) *Attorney, Agent, or Firm*—Knobbe, Martens, Olson & Bear, LLP

(57) ABSTRACT

A method for simplification of a microbial genome or microbial nucleic acid comprising treating microbial genome or nucleic acid with an agent that modifies cytosine to form derivative microbial nucleic acid and amplifying the derivative microbial nucleic acid to produce a simplified form of the microbial genome or nucleic acid.

63 Claims, 15 Drawing Sheets

Staphylococcus specific PCR

1. *Escherichia coli*
2. *Neisseria gonorrheae*
3. *Klebsiella pneumoniae*
4. *Moraxella catarrhalis*
5. *Pseudomonas aeruginosa*
6. *Proteus vulgaris*
7. *Enterococcus faecalis*
8. *Staphylococcus epidermidis*
9. *Staphylococcus aureus*
10. *Staphylococcus xylosis*
11. *Streptococcus pneumoniae*
12. *Streptococcus haemolyticus*

U.S. PATENT DOCUMENTS

| | | | |
|---|---|---|---|
| 5,824,517 | A | 10/1998 | Cleuziat et al. |
| 5,952,174 | A | 9/1999 | Nikiforov et al. |
| 6,156,501 | A | 12/2000 | McGall et al. |
| 6,251,637 | B1 | 6/2001 | Blusch |
| 6,265,171 | B1 | 7/2001 | Herman et al. |
| 6,331,393 | B1 | 12/2001 | Laird et al. |
| 6,692,918 | B2 | 2/2004 | Kurn |
| 6,960,436 | B2 | 11/2005 | Cottrell |
| 7,008,770 | B1 | 3/2006 | Berlin |
| 7,288,373 | B2 | 10/2007 | Millar et al. |
| 7,413,855 | B2 | 8/2008 | Bergmann et al. |
| 7,504,207 | B2 | 3/2009 | Bergquist et al. |
| 2002/0086324 | A1 | 7/2002 | Laird et al. |
| 2002/0142397 | A1 | 10/2002 | Collas et al. |
| 2003/0073081 | A1 | 4/2003 | Mukai et al. |
| 2003/0082600 | A1 | 5/2003 | Olek et al. |
| 2003/0119025 | A1 | 6/2003 | Olek et al. |
| 2003/0143577 | A1 | 7/2003 | Hogrefe et al. |
| 2004/0067559 | A1 | 4/2004 | McCarthy et al. |
| 2004/0086944 | A1 | 5/2004 | Grigg et al. |
| 2004/0203004 | A1 | 10/2004 | Bernard et al. |
| 2004/0219539 | A1 | 11/2004 | Millar et al. |
| 2005/0019762 | A1 | 1/2005 | Olek |
| 2005/0059003 | A1 | 3/2005 | Enoki et al. |
| 2005/0118578 | A1 | 6/2005 | Mineno et al. |
| 2005/0202490 | A1 | 9/2005 | Makarov et al. |
| 2006/0014144 | A1 | 1/2006 | Christensen et al. |
| 2006/0051771 | A1 | 3/2006 | Murphy et al. |
| 2006/0166203 | A1 | 7/2006 | Took |
| 2006/0286576 | A1 | 12/2006 | Lofton-Day |
| 2007/0020633 | A1 | 1/2007 | Millar |
| 2007/0020639 | A1 | 1/2007 | Shapero |
| 2007/0020653 | A1 | 1/2007 | Holliger |
| 2007/0026070 | A1 | 2/2007 | Vonwiller |
| 2007/0042365 | A1 | 2/2007 | Millar et al. |
| 2007/0178457 | A1 | 8/2007 | Millar |
| 2007/0178459 | A1 | 8/2007 | Millar |
| 2007/0190530 | A1 | 8/2007 | Birkner et al. |
| 2007/0264653 | A1 | 11/2007 | Berlin et al. |
| 2008/0050738 | A1 | 2/2008 | Millar |
| 2009/0029346 | A1 | 1/2009 | Millar et al. |
| 2009/0042732 | A1 | 2/2009 | Millar |
| 2009/0130657 | A1 | 5/2009 | Millar |
| 2009/0263909 | A1 | 10/2009 | Millar |
| 2010/0041013 | A1 | 2/2010 | Millar et al. |
| 2010/0092972 | A1 | 4/2010 | Millar et al. |

FOREIGN PATENT DOCUMENTS

| | | |
|---|---|---|
| EP | 1 319 718 | 6/2003 |
| EP | 1 443 052 | 8/2004 |
| EP | 1 801 213 | 6/2007 |
| WO | WO 98/020157 A2 * | 5/1988 |
| WO | WO 95/01456 | 1/1995 |
| WO | WO 95/22623 | 8/1995 |
| WO | WO 97/41254 | 11/1997 |
| WO | WO 97/45559 | 12/1997 |
| WO | WO 98/20157 A | 5/1998 |
| WO | WO 98/29108 | 7/1998 |
| WO | WO 99/09211 A2 | 2/1999 |
| WO | WO 99/14226 | 3/1999 |
| WO | WO 99/49081 A2 | 9/1999 |
| WO | WO 00/44934 | 8/2000 |
| WO | WO 00/50869 A2 | 8/2000 |
| WO | WO 01/09374 A2 | 2/2001 |
| WO | WO 01/38565 A2 | 5/2001 |
| WO | WO 01/42493 A2 | 6/2001 |
| WO | WO 01/76451 A2 | 10/2001 |
| WO | WO 02/36821 A2 | 5/2002 |
| WO | WO 02/38801 | 5/2002 |
| WO | WO 02/46452 | 6/2002 |
| WO | WO 02/072880 | 9/2002 |
| WO | WO 02/097065 | 12/2002 |
| WO | WO 03/008623 A2 | 1/2003 |
| WO | WO 03/048732 | 6/2003 |
| WO | WO 03/051901 A2 | 6/2003 |
| WO | WO 03/052132 A2 | 6/2003 |
| WO | WO 03/052133 A2 | 6/2003 |
| WO | WO 03/052134 A2 | 6/2003 |
| WO | WO 2004/015139 | 2/2004 |
| WO | WO 2004 015139 A * | 2/2004 |
| WO | WO 2004/015139 A1 * | 2/2004 |
| WO | WO 2004 015139 A1 * | 2/2004 |
| WO | WO 2004/065625 | 8/2004 |
| WO | WO 2004/090166 A1 | 10/2004 |
| WO | WO 2004/096825 | 11/2004 |
| WO | WO 2004/111266 A | 12/2004 |
| WO | WO 2005/021778 | 3/2005 |
| WO | WO 2005/021778 A | 3/2005 |
| WO | WO 2005/056790 A1 | 6/2005 |
| WO | WO 2006/058393 | 6/2006 |
| WO | WO 2006/066353 | 6/2006 |
| WO | WO 2006/113770 A1 | 10/2006 |
| WO | WO 2007/106802 A2 | 9/2007 |
| WO | WO 2008/109945 | 9/2008 |
| WO | WO 2008/135512 A2 | 11/2008 |
| WO | WO 2009/067743 | 6/2009 |
| WO | WO 2009/070843 | 6/2009 |
| WO | WO 2009/079703 | 7/2009 |

OTHER PUBLICATIONS

Zeschnigk (Sep. 7, 2004) Nucleic Acids Research vol. 32 pp. 1 to 5.*

The Supplementary European Search Report issued on corresponding European Patent Application No. EP 05 81 3335, dated Mar. 12, 2009.

Venter et al., "The Sequence of the Human Genome," *Science*, vol. 291 (5523): pp. 1304-1351, (2001).

Badal Sushma et al.: "The human papillomavirus-18 genome is efficiently targeted by cellular DNA methylation" Virology, vol. 324, No. 2, Jul. 1, 2004, pp. 483-492.

Badal V. et al.: "CpG methylation of human papillomavirus type 16 DNA in cervical cancer cell lines and in clinical specimens: Genomic hypomethylation correlates with carcinogenic progression" Journal of Virology, the American Society for Microbiology, US, vol. 77, No. 11, Jun. 1, 2003, pp. 6227-6234.

Baleriola C et al.: "Comparison of a novel HPV test with the Hybrid Capture II (hcII) and a reference PCR method shows high specificity and positive predictive value for 13 high-risk human papillomavirus infections" Journal of Clinical Virology, Elsevier, Amsterdam, NL, vol. 42, No. 1, May 1, 2008, pp. 22-26.

NCBI Database Accession No. M24485, Dec. 5, 1994.

European Search Report issued in corresponding European Application No. 06774977, dated Jul. 28, 2009.

Extended European Search Report issued in corresponding European Application No. 05779000.8, dated Dec. 4, 2008.

Extended European Search Report issued in corresponding European Application No. 05821631.8, dated Dec. 7, 2008.

Feng et al.: "Detection of hypermethylated genes in women with and without cervical neoplasia." Journal of the National Cancer Institute Feb. 16, 2005, vol. 97, No. 4, pp. 273-282.

Gu W. et al, Depletion of *Saccharomyces cerevisiae* tRNAHis Guanylyltransferase Thglp leads to uncharged tRNAH is with additional m5C, Mol Cell Biol. Sep. 2005; vol. 25, No. 18, pp. 8191-8201.

International Search Report issued on corresponding PCT Application No. PCT/AU2008/000367, dated May 14, 2008.

International Search Report issued on corresponding PCT Application No. PCT/AU2006/000755, dated Aug. 30, 2006.

Kalantari, Mina et al. "Conserved methylation patterns of human papillomavirus type 16 DNA in asymptomatic infection and cervical neoplasia," *Journal of Virology,*.vol. 78, No. 23, Dec. 2004, pp. 12762-12772.

Kim T.Y et al: "DNA hypermethylation in gastric cancer" Alimentary Pharmacology & Therapeutics, vol. 20, No. Suppl. 1, Jul. 2004, pp. 131-142.

Kozak et al.: "Influence of secondary structure on binding and migration of 40S ribosomal subunits," Cell, vol. 19, 1980, pp. 79-90.

Malyukova A.V et al: "Methylation of the Putative Tumor Suppressor Gene RASSF1A in Primary Cervical Tumors" Molecular Biology, Kluwer Academic Publishers-Plenum Publishers, NE, vol. 38, No. 6, Nov. 1, 2004, pp. 857-864.

Narayan, Gopeshwar et al: "Frequent Promoter Methylation of CDH1, DAPK, RARB, and HIC1 Genes in Carcinoma of Cervix Uteri: Its Relationship to Clinical Outcome" Molecular Cancer, Biomed Central, London, GB, vol. 2, No. 1, May 13, 2003, p. 24.

Nousbaum, J. et al., "Prospective Characteristics of Full-Length Hepatitis C Virus NS5A Quasispecies during Induction and Combination Antiviral Therapy," Journal of Virology, 74, No. 19, pp. 9028-9038 (2000).

Office Action in U.S. Appl. No. 10/543,017 dated Dec. 8, 2008.
Office Action in U.S. Appl. No. 10/543,017 dated Jun. 20, 2008.
Office Action in U.S. Appl. No. 10/543,017 dated Oct. 19, 2007.
Office Action in U.S. Appl. No. 11/660,586 dated Sep. 15, 2009.
Office Action in U.S. Appl. No. 11/573,873 dated Sep. 2, 2009.
Office Action in U.S. Appl. No. 11/573,873 dated May 4, 2009.

Ratushna V.G. et al.: "Secondary structure in the target as a confounding factor in synthetic oligomer microarray design," BMC Genomics, vol. 6, No. 1, Mar. 2005, p. 31.

Supplementary European Search Report issued on corresponding European Patent Application No. EP 05 81 3335, dated Mar. 12, 2009.

Supplementary European Search Report issued on corresponding European Patent Application No. EP 06 77 4977, dated Jul. 28, 2009.

Ushijima Toshikazu et al.: "Aberrant Methylations in Cancer Cells: Where Do They Come From?" Cancer Science, vol. 96, No. 4, Apr. 2005, pp. 206-211.

Verma M: "Viral Genes and Methylation" Annals of the New York Academy of Sciences 200303 US, vol. 983, Mar. 2003, pp. 170-180.

Widschwendter et al.: "Analysis of Aberrant DNA Methylation and Human Papillomavirus DNA in Cervicovaginal Specimens to Detect Invasive Cervical Cancer and Its Precursors" Clinical Cancer Research, The American Association for Cancer Research, US, vol. 10, No. 10, May 15, 2004, pp. 3396-3400.

Yanagi et al., "Hepatitis C Virus: An Infectious Molecular Clone of a Second Major Genotype (2A) and Lack of Viability of Intertypic 1A and 2A Chimeras," Virology 262, pp. 250-263 (1999).

Office Action in U.S. Appl. No. 11/756,534 dated Feb. 22, 2010.
Office Action in U.S. Appl. No. 11/660,586 date Apr. 15, 2010.
Office Action in U.S. Appl. No. 12/066,644 dated Apr. 22, 2010.

Bakker et al. JBC, vol. 277, No. 25, pp. 22573-22580, Jun. 2002.
Lee et al., Cancer Epidemiology, Biomarkers, Prevention, vol. 6, pp. 443-450, Jun. 1997.
Esteller et al., Cancer Research, vol. 58, pp. 4514-4518, Oct. 1998.
Virmani et al., Clinical Cancer Research, vol. 7, No. 3, pp. 584-489, Mar. 2001.
Melki et al., Cancer Research, vol. 59, pp. 3730-3740, Aug. 1999.
Toyota et al., Cancer Research, vol. 59, pp. 4535-4541, Sep. 1999.
Shao-Qing et al., Chinese Journal of Agricultural Biotechnology, vol. 4, No. 1, pp. 75-79, 2007.
Pao et al., Human Molecular Genetics, vol. 10, No. 9, pp. 903-910, 2001.
Cameron et al., Blood, vol. 94, No. 7, pp. 2445-2451, Oct. 1999.
Tsuda et al., Gynecologic Oncology, vol. 91, pp. 476-485, 2003.
Venter et al., "The Sequence of the Human Genome," Science, vol. 291 (5523): pp. 1304-1351, (2001).
Cohen, Y. et al, "Hypermethylation of CpG Island Loci of Multiple Tumor Suppressor Genes in Retinoblastoma", Experimental Eye Research, 2008, vol. 86, No. 2, pp. 201-206.
Grunau, C. et al. Bisulphite genomic sequencing: systematic investigation of critical experimental parameters. Nucleic Acids Research (2001) vol. 29, No. 13, e65.
International Search report issued in PCT Application No. PCT/AU2008/001751, mailed Feb. 18, 2009.
International Search report issued in corresponding PCT Application No. PCT/AU2008/001796, mailed Feb. 23, 2009.

Munson, K. et al. Recovery of bisulphite-converted genomic sequences in the methylation-sensitive QPCR. Nucleic Acids Research (2007) vol. 35, No. 9, pp. 2893-2903.

Shiraishi, M. et al. High Speed Conversion of Cytosine to Uracil in Bisulphite Genomic Sequencing Analysis of DNA Methylation; DNA Research (2004) vol. II, pp. 409-415.

Strategene, 1988 Catalog, p. 39.

Triplett, J. W. et al., Carbon-13 NMR Investigation of the bisulphite induced changes in yeast RNA; Biochemical and Biophysical Research Communications (1977), vol. 77, No. 4, pp. 1170-1175.

Yao, M. et al, ""Further Characterization of *Escherichia coli* Endonuclease V"", Journal of Biological Chemistry, 1997, vol. 272, No. 49, pp. 30774-30779.

Hitchcock, T.M. et al., "Cleavage of deoxyoxanosine-containing oligodeoxyribonucleotides by bacterial endonuclease V", Nucleic Acids Research, 2004, vol. 32, No. 13, pp. 4071-4080.

International Search Report issued in PCT Application No. PCT/AU2008/001891, mailed Feb. 3, 2009.

Longo, M.C. et al, "Use of Uracil DNA Glycosylase to Control Carry-Over Contamination in Polymerase Chain Reactions", Gene, vol. 93, No. I, pp. 125-128, Sep. 1990.

Notice of Allowance issued in U.S. Appl. No. 10/561,029 dated May 28, 2010.

Office Action in U.S. Appl. No. 11/756,534 dated Jun. 8, 2010.

Cottrell et al., A real-time PCR assay for DNA-methylation-specific blockers. Nucleic Acid Research, 32(1):e10 (8 pages). Jan. 13, 2004.

Notice of Allowance issued in U.S. Appl. No. 11/575,060, mailed Jun. 15, 2010.

Christensen et al., "Intercalating nucleic acids containing insertions of 1-o-(1-pyrenylmethyl)glycerol: stabilization of dsDNA and discrimination of DNA over RNA." Nucleic Acid Res. vol. 30, No. 22, pp. 4918-4925, (2002).

Clark et al., "High sensitivity mapping methylated cytosines." Nucleic Acids Research, 22(15): 2990-2997 (1994).

Clark, et al., "Bisulphite genomic sequencing of methylated cytosines." Laboratory Methods for the Detection of Mutations and Polymorphisms in DNA. Graham R. Taylor, Ed. CRC Press, New York (1997), pp. 151-162.

Dean et al., "Comprehensive human genomeamplification using multiple displacement amplification." PNAS, 99(8): 5261-5266 (2002).

Eads et al., "MethylLight: a high-throughput assay to measure DNA methylation." Nucleic Acids Research, 28(8): i-viii (2000).

Feil, et al., "Methylation analysis on individual chromoshomes: improved protocol for bisulphate genomic sequencing." (1994) Nucleic Acids Research 22(4): 695-696.

Frommer et al., "A genomic sequencing protocol that yields a positive display of 5-methylcytosine residues in individual DNA strands," Proc. Natl. Acad. Sci. 89: 1827-1831 (1992).

Grigoriev et al., "A Triple Helix-forming Oligonucleotide-Intercalator Conjugate Acts as a Transcriptional Repressor via Inhibition of NFkB Binding to Interleukin-2 Receptor a-Regulatory Sequence." The Journal of Biological Chemistry, 267 (5): 3389-3395 (1992).

Grunau, et al., "Bisulfite genomic sequencing: systematic investigation of critical experimental parameters." Nucleic Acid Research, (2001) vol. 29, No. 13e65, pp. 1-7.

Hakelien et al., "Reprogramming fibroblasts to express T-cell functions using cell extracts." Nature Briotechnology, 20(5): 460-466 (2002).

Hakelien et al., Cloning and Stem Cells, 4: 379-387 (2002).

Herman, et al., "Methylation-specific PCR-: a novel PCR assayfor methylation status of CpG islands." (1996) Proc. Natl. Acad. Sci. 93:9821-9826.

Hosono et al. "Unbiased Whole-Genome Amplification Directly from Clinical Samples." *Genome Research;* 13:954-964 (2003).

International Human Genome Sequencing Consrtium, "Initial sequencing and analysis of the human genome," Nature, 409(6822): 860-921 (2001).

International Preliminary Report on Patentability issued on the corresponding PCT Application No. PCT/AU2006/000698, dated Apr. 20, 2007.

International Search Report Issued on the corresponding PCT Application No. PCT/AU2006/000698, dated Aug. 1, 2006.

Kinoshita et al., "Methylation of the androgen receptor minimal promoter silences transcription in human prostate cancer." Cancer Research, 60(13): 3623-3630 (Jul. 1, 2000).

Kono, "Nuclear transfer and reprogramming." Reviews of Reproduction, Journal of Reproduction and Fertility, vol. 2 No. 2, pp. 74-80 (May 1997).

Millar et al., "A distinct sequence (ATAAA)in separates methylated and unmethylated domains at the 5'-end of the GSTPI CpG island," J. Biol. Chem., 275(32): 24893-24899 (2000).

Millar et al., "Detailed methylation analysis of the glutathione S-transferase pi (GSTPI) gene in prostate cancer," Oncogene 18(6): 1313-1324, (1999).

Monk, "Epigentic programming of differential gene expression in development and evolution" Dev. Genetics, vol. 17, pp. 183-197 (1995).

Newton et al., "The production of PCR products with 5' single-stranded tails using primers that incorporate novel phosphoramidite intermediates." Nucleic Acid Res. vol. 21 No. 5, pp. 1155-1162 (1993).

Nilsson et al., Science; 265:2085-2088 (1994).

Office Action in U.S. Appl. No. 10/416,637 dated May 4, 2006.

Office Action in U.S. Appl. No. 10/428,310 dated Aug. 31, 2006.

Office Action in U.S. Appl. No. 10/428,310 dated Jan. 4, 2006.

Office Action in U.S. Appl. No. 10/428,310 dated Jul. 5, 2006.

Office Action in U.S. Appl. No. 10/428,310 dated Nov. 3, 2006.

Office Action in U.S. Appl. No. 10/536,633 dated Apr. 4, 2007.

Office Action in U.S. Appl. No. 10/536,633 dated Jan. 25, 2007.

Okada, et al., "Sequence Determination of Rat U5 RNA Unsing a Chemical Modification Procedure for Counteracting Sequence Compression." (1982) J. Biochem. 91: 1281-1291.

Olek, et al. "A modified and improved method for bisulphate based cytosine methylation analysis." (1996) Nucleic Acids Research, 24(24): 2065-5066.

Paulin et al., "Urea improves efficiency of bisulphite-mediated sequencing of 5'-methylcytosine in genomic DNA." Nucleic Acid Research, 26(21): 5009-5010 (Nov. 1, 1998).

Pietrobono et al., "Quantitative analysis of DNA demethylation and transcriptional reactivation of the FMR1 gene in fragile X cellstreated with 5-azadeoxycytidine." Nucleic Acids Research, 30(14): 3278-3285 (2002).

Raizis et al., Anal. Biochem., 226: 161-166 (1995).

Rein et al., "Identifying 5-methylcytosine and related modifications in DNA genomes." Nucleic Acids Research, 26 (10): 2255-2264 (May 15,1998).

Robertson et al., "Blood" 90: 4480-4484 (1997).

Robertson et al. "DNA methylation: past, present, and future directions." Carcinogenesis. 21(3): 461-467 (2000).

Sakaguchi et al. "Cautionary Note on the Use of dUMP-Containing PCR Primers with *Pfu* and Vent$_R$® DNA Polymerases." *Biotechniques;* 21(3):368 & 370 (1996).

Sakashita et al., J. Clin. Invest., 108: 1195-1204 (2001).

Shapiro et al., "Deamination of cytosine derivatives by bisulfite. Mechanism of the reaction," J. Am. Chem. Soc., 96: 206-212 (1974).

Tada et al., "Embryonic germ cells induce epigenetic reprogramming of somatic nucleus in hybrid cells." The EMBO Journal, 16(21): 6510-6520 (1997).

Telenius et al. "Degenerate Oligonucleotide-Primed PCR: General Amplification of Target DNA by a Single Degenerate Primer." *Genomics;* 13(3):718-725 (1992).

Tohgi et al., "Molecular Brain Research," 65:124-128 (1999).

Waranecke et al., "Detection and measurement of PCR bias in quantitative methylation analysis of bisulphite-treated DNA," Nucleic Acids Research, vol. 25 No. 21, pp. 4422-4426, (1997).

Xiong et al., "COBRA: a sensititive and quantitative DNA methylation assay." (1997) Nucleic Acids Research, 25 (12): 2532-2534.

* cited by examiner

Figure 1.

Neisseria iga sequences

Non-Converted sequence

Neisseria meningitidis    GTAATCA AGGTCGTCTT GAAGACTACA ACATGGC (SEQ ID No 145)
Neisseria gonorrhoeae     GCAATTT AGGCCGCCTC GAAGATTATA ATATGGC (SEQ ID No 146)

Consensus sequence        GYAATYW AGGYCGYCTY GAAGAYTAYA AYATGGC (SEQ ID No 3)
                          512 Possible primer combinations
                          74% sequence similarity Simplified sequence Neisseria meningitidis    GTAATTA AGGTTGTTTT GAAGATTATA ATATGGT (SEQ ID No 147)
Neisseria gonorrhoeae     GTAATTT AGGTTGTTTT GAAGATTATA ATATGGT (SEQ ID No 148)

Consensus sequence        GTAATTW AGGTTGTTTT GAAGATTATA ATATGGT (SEQ ID No 4)
                          2 Primer combinations
                          97% sequence similarity

Figure 2.

Neisseria iga sequences

Non-Converted sequence

Neisseria meningitidis    GTAATCA AGGTCGTCTT GAAGACTACA ACATGGC (SEQ ID No 145)
Neisseria gonorrhoeae     GCAATTT AGGCCGCCTC GAAGATTATA ATATGGC (SEQ ID No 146)

Consensus INA sequence            AGGYCGYCTY GAAGAY (SEQ ID No 149)
                          16 possible primer combinations
                          75% sequence similarity Simplified sequence Neisseria meningitidis    GTAATTA AGGTTGTTTT GAAGATTATA ATATGGT (SEQ ID No 147)
Neisseria gonorrhoeae     GTAATTT AGGTTGTTTT GAAGATTATA ATATGGT (SEQ ID No 148)

Consensus INA sequence            AGGTTGTTTT GAAGAT (SEQ ID No 150)
                          100% sequence similarity

Figure 3.

*iga* gene sequences

|  | Non-converted | Simplified |
|---|---|---|
| *Haemophilus influenza* | TAACTACGG AAGATCA(151) | TAATTATGG AAGATTA(152) |
| *Neisseria meningitidis* | GTAATCAAG GTCGTCT(153) | GTAATTAAG GTTGTTT(154) |
| *Neisseria gonorrhoeae* | GCAATTTAG GCCGCCT(155) | GTAATTTAG GTTGTTT(156) |

Figure 4.

*Streptococcus* tuf gene

Non-Converted sequence

| | | |
|---|---|---|
| *S.oralis* | AAGCTCTTGA AGGTGACTCT AAATACGAAG ACATCATCAT | (SEQ ID No 157) |
| *S.mitis* | AAGCCCTTGA AGGTGACACT AAATACGAAG ACATCGTTAT | (SEQ ID No 158) |
| *S.dysgalactiae* | AAGCTCTTGA AGGTGACTCA AAATACGAAG ATATCATCAT | (SEQ ID No 159) |
| *S.cristatus* | AAGCTCTTGA AGGTGATACT AAGTACGAAG ACATCATCAT | (SEQ ID No 160) |
| *S.gordonii* | AAGCTCTTGA AGGTGACTCT AAATACGAAG ATATCATCAT | (SEQ ID No 161) |
| *S.parauberis* | AAGCTCTTGA AGGCGATACA GCACATGAAG ATATCATCAT | (SEQ ID No 162) |
| *S.pneumoniae* | AAGCTCTTGA AGGTGACTCT AAATACGAAG ACATCGTTAT | (SEQ ID No 163) |
| *S.bovis* | AAGCTCTTGA AGGTGACACT CAGTACGAAG ATATCATCAT | (SEQ ID No 164) |
| *S.vestibularis* | AAGCTCTTGA AGGTGATTCT AAATACGAAG ACATCATCAT | (SEQ ID No 165) |
| *S.uberis* | AAGCTCTTGA AGGTGATTCT AAATACGAAG ACATCATCAT | (SEQ ID No 166) |
| Consensus | AAGCYCTTGA AGGYGAYWCW VMRYAYGAAG AYATCRTYAT | (SEQ ID No 167) |

67.5% Homology
12,288 possible primer combinations

Simplified sequence

| | | |
|---|---|---|
| *S.oralis* | AAGTTTTTGA AGGTGATTTT AAATATGAAG ATATTATTAT | (SEQ ID No 168) |
| *S.mitis* | AAGTTTTTGA AGGTGATATT AAATATGAAG ATATTGTTAT | (SEQ ID No 169) |
| *S.dysgalactiae* | AAGTTTTTGA AGGTGATTTA AAATATGAAG ATATTATTAT | (SEQ ID No 170) |
| *S.cristatus* | AAGTTTTTGA AGGTGATATT AAGTATGAAG ATATTATTAT | (SEQ ID No 171) |
| *S.gordonii* | AAGTTTTTGA AGGTGATTTT AAATATGAAG ATATTATTAT | (SEQ ID No 172) |
| *S.parauberis* | AAGTTTTTGA AGGTGATATA GTATATGAAG ATATTATTAT | (SEQ ID No 173) |
| *S.pneumoniae* | AAGTTTTTGA AGGTGATTTT AAATATGAAG ATATTGTTAT | (SEQ ID No 174) |
| *S.bovis* | AAGTTTTTGA AGGTGATATT TAGTATGAAG ATATTATTAT | (SEQ ID No 175) |
| *S.vestibularis* | AAGTTTTTGA AGGTGATTTT AAATATGAAG ATATTATTAT | (SEQ ID No 176) |
| *S.uberis* | AAGTTTTTGA AGGTGATTTT AAATATGAAG ATATTATTAT | (SEQ ID No 177) |
| Consensus | AAGTTTTTGA AGGTGATWTW RWRTATGAAG ATATTRTTAT | (SEQ ID No 178) |

85% Homology
64 possible primer combinations

Figure 5.

Staphylococcal enterotoxin genes (SE)

|  | Non-Converted sequence | Simplified sequence |
|---|---|---|
| SEC | TAC AACGACAATA AAACGGTTGA(179) | TAT AATGATAATA AAATGGTTGA(180) |
| SEI | TAC GGAGATAATA AAGTTGTTGA(181) | TAT GGAGATAATA AAGTTGTTGA(182) |
| SEC3 | TAC AACGACAATA AAACGGTTGA(183) | TAT AATGATAATA AAATGGTTGA(184) |
| SEC1 | TAC AACGACAATA AAACGGTTGA(185) | TAT AATGATAATA AAATGGTTGA(186) |
| SEA | TAT AGAGATAATA AAACGATTAA(187) | TAT AGAGATAATA AAATGATTAA(188) |
| SEE | TAC AGAGATAATA AAACTATTAA(189) | TAT AGAGATAATA AAATTATTAA(190) |
| SEB | TAC AATGACAATA AAATGGTTGA(191) | TAT AATGATAATA AAATGGTTGA(192) |
| CONCENSUS | TAY RRHGAYAATA AARYKRTTRA(193) | TAT RRWGATAATA AARTKRTTRA(194) |
|  | 56% Homology | 74% Homology |
|  | 1536 primer combinations | 64 Primer combinations |

Figure 6.

Influenza virus neuraminidase

Non-Converted sequence

| | | |
|---|---|---|
| Influenza A virus H5N1 | TGTGTGTGCA GGGATAATTG | (SEQ ID No 195) |
| Influenza A virus H7N3 | TGTATATGTA GGGACAATTG | (SEQ ID No 196) |
| Influenza A virus H5N8 | TGTGTTTGTA GAGACAACTG | (SEQ ID No 197) |
| Influenza A virus H5N3 | TGTATATGTA GGGACAATTG | (SEQ ID No 198) |
| Influenza A virus H5N2 | TGTGTTTGCA GAGATAATTG | (SEQ ID No 199) |
| Influenza A virus H6N6 | TGCATTTGCA GGGACAATTG | (SEQ ID No 200) |
| Influenza A virus H2N9 | TGCACTTGCA GGGATAATTG | (SEQ ID No 201) |
| Influenza A virus H6N5 | TGCGTTTGCC GAGATAATTG | (SEQ ID No 202) |
| Influenza B virus NA | TGTGCCTGTA GAGATAACAG | (SEQ ID No 203) |

Consensus      TGYRYNTGYM GRGAYAAYWG (SEQ ID No 204)
2048 Possible primer combinations
50% Homology Simplified sequence

| | | |
|---|---|---|
| Influenza A virus H5N1 | TGTGTGTGTA GGGATAATTG | (SEQ ID No 205) |
| Influenza A virus H7N3 | TGTATATGTA GGGATAATTG | (SEQ ID No 206) |
| Influenza A virus H5N8 | TGTGTTTGTA GAGATAATTG | (SEQ ID No 207) |
| Influenza A virus H5N3 | TGTATATGTA GGGATAATTG | (SEQ ID No 208) |
| Influenza A virus H5N2 | TGTGTTTGTA GAGATAATTG | (SEQ ID No 209) |
| Influenza A virus H6N6 | TGTATTTGTA GGGATAATTG | (SEQ ID No 210) |
| Influenza A virus H2N9 | TGTATTTGTA GGGATAATTG | (SEQ ID No 211) |
| Influenza A virus H6N5 | TGTGTTTGTT GAGATAATTG | (SEQ ID No 212) |
| Influenza B virus NA | TGTGTTTGTA GAGATAATAG | (SEQ ID No 213) |

Consensus      TGTRTDTGTW GRGATAATWG (SEQ ID No 214)
48 Possible primer combinations
75% homology

Figure 7.

Rotavirus VP4 genes

| | Non-Converted | Simplified |
|---|---|---|
| Rotavirus Strain A VP4 | CTAAATTCGC TCCGATTTA(215) | TTAAATTTGT TTTGATTTA(216) |
| Rotavirus Strain B VP4 | CAAAATTGAC CCAGACTTA(217) | TAAAATTGAT TTAGATTTA(218) |
| Rotavirus Strain C VP4 | TTAAATTCGT TAAGATTCA(219) | TTAAATTTGT TAAGATTTA(220) |
| Consensus Sequence | YWAAATTSRY YMMGAYTYA(221) | TWAAATTKRT TWWGATTTA(222 |
| | 52% Homology | 74% Homology |
| | 512 primer combinations | 32 primer combinations |

Figure 8.

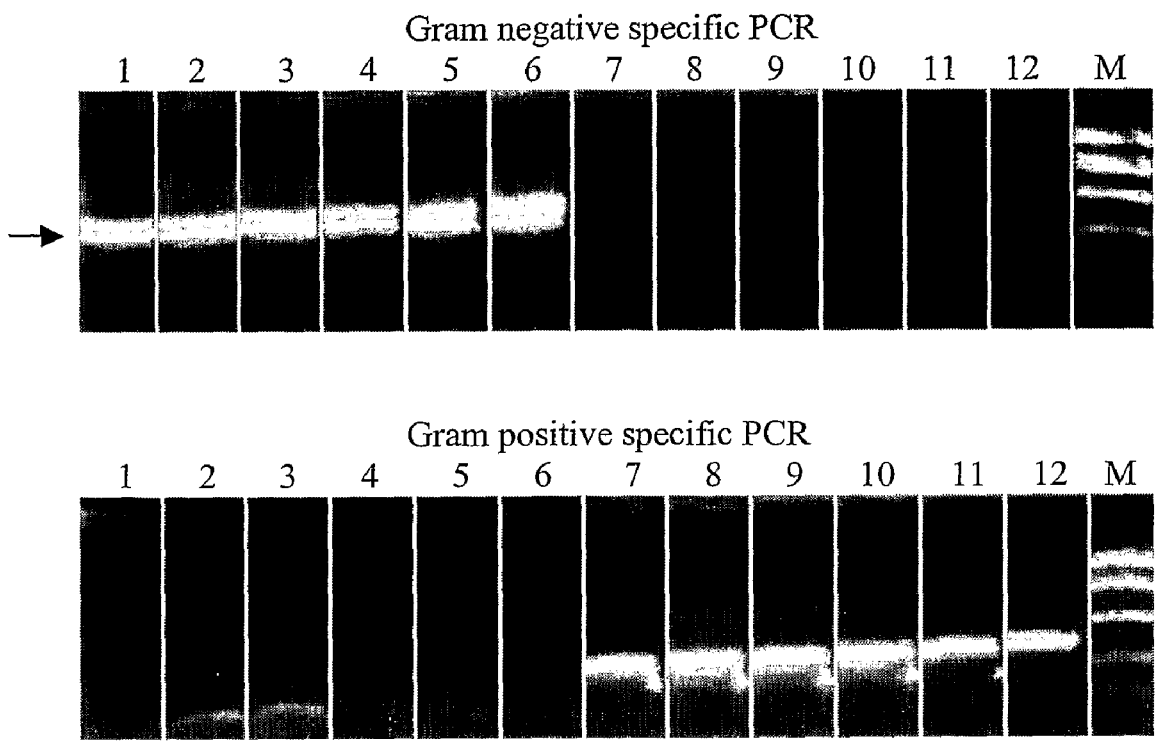

| | Gram Stain |
|---|---|
| 1. *Escherichia coli* | Negative |
| 2. *Neisseria gonorrheae* | Negative |
| 3. *Klebsiella pneumoniae* | Negative |
| 4. *Moraxella catarrhalis* | Negative |
| 5. *Pseudomonas aeruginosa* | Negative |
| 6. *Proteus vulgaris* | Negative |
| 7. *Enterococcus faecalis* | Positive |
| 8. *Staphylococcus epidermidis* | Positive |
| 9. *Staphylococcus aureus* | Positive |
| 10. *Staphylococcus xylosis* | Positive |
| 11. *Streptococcus pneumoniae* | Positive |
| 12. *Streptococcus haemolyticus* | Positive |

1. Escherichia coli
2. Neisseria gonorrheae
3. Klebsiella pneumoniae
4. Moraxella catarrhalis
5. Pseudomonas aeruginosa
6. Proteus vulgaris
7. Enterococcus faecalis
8. Staphylococcus epidermidis
9. Staphylococcus aureus
10. Staphylococcus xylosis
11. Streptococcus pneumoniae
12. Streptococcus haemolyticus Neisseria specific PCR 1. *Escherichia coli*
2. *Neisseria gonorrheae*
3. *Klebsiella pneumoniae*
4. *Moraxella catarrhalis*
5. *Pseudomonas aeruginosa*
6. *Proteus vulgaris*
7. *Enterococcus faecalis*
8. *Staphylococcus epidermidis*
9. *Staphylococcus aureus*
10. *Staphylococcus xylosis*
11. *Streptococcus pneumoniae*
12. *Streptococcus haemolyticus*

Escherichia coli specific PCR

1. *Escherichia coli*
2. *Neisseria gonorrheae*
3. *Klebsiella pneumoniae*
4. *Moraxella catarrhalis*
5. *Pseudomonas aeruginosa*
6. *Proteus vulgaris*
7. *Enterococcus faecalis*
8. *Staphylococcus epidermidis*
9. *Staphylococcus aureus*
10. *Staphylococcus xylosis*
11. *Streptococcus pneumoniae*
12. *Streptococcus haemolyticus*

1. *Escherichia coli*
2. *Neisseria gonorrheae*
3. *Klebsiella pneumoniae*
4. *Moraxella catarrhalis*
5. *Pseudomonas aeruginosa*
6. *Proteus vulgaris*
7. *Enterococcus faecalis*
8. *Staphylococcus epidermidis*
9. *Staphylococcus aureus*
10. *Staphylococcus xylosis*
11. *Streptococcus pneumoniae*
12. *Streptococcus haemolyticus*

1. Escherichia coli
2. Neisseria gonorrheae
3. Klebsiella pneumoniae
4. Moraxella catarrhalis
5. Pseudomonas aeruginosa
6. Proteus vulgaris
7. Enterococcus faecalis
8. Staphylococcus epidermidis
9. Staphylococcus aureus
10. Staphylococcus xylosis
11. Streptococcus pneumoniae
12. Streptococcus haemolyticus Staphylococcus epidermidis specific PCR 1. *Escherichia coli*
2. *Neisseria gonorrheae*
3. *Klebsiella pneumoniae*
4. *Moraxella catarrhalis*
5. *Pseudomonas aeruginosa*
6. *Proteus vulgaris*
7. *Enterococcus faecalis*
8. *Staphylococcus epidermidis*
9. *Staphylococcus aureus*
10. *Staphylococcus xylosis*
11. *Streptococcus pneumoniae*
12. *Streptococcus haemolyticus*

Figure 16A. *Staphylococcus epidermidis*

Normal DNA sequence (SEQ ID NO 223)

GATTAAGTTATTAAGGGCGCACGGTGGATGCCTTGGCACTAGAAGCCGATGAAGGACGTTACTAACGA
CGATATGCTTTGGGTAGCTGTAAGTAAGCGTTGATCCAGAGATTTCCGAATGGGGGAACCCAGCATGA
GTTATGTCATGTTATCGATATGTGAATTTATAGCATGTCAGAAGGCAGACCCGGAGAACTGAAACATC
TTAGTACCCGGAGGAAGAGAAAGAAAAATCGATTCCCTGAGTAGCGGCGAGCGAAACGGGAAGAGCCC
AAACCAACAAGCTTGCTTGTTGGGGTTGTAGGACACTCTATACGGAGTTACAAAAGAACATGTTAGAC
GAATCATCTGGAAAGATGAATCAAAGAAGGTAATAATCCTGTAGTCGAAAACATATTCTCTCTTGAGT
GGATCCTGAGTACGACGGAGCACGTGAAATTCCGTCGGAATCTGGGAGGACCATCTCCTAAGGCTAAA
TACTCTCTAGTGACCGATAGTGAACCAGTACCGTGAGGGAAAGGTGAAAAGTACCCCGGAAGGGGAGT
GAAAGAGAACTTGAAACCGTGTGCTTACAAGTAGTCAGAGCCCGTTAATGGGTGATGGCGTGCCTTTT
GTAGAATGAACCGGCGAGTTACGATCTGATGCAAGGTTAAGCAGCAAATGCGGAGCCGCAGCGAAAGC
GAGTCTGAATAGGGCGTTGAGTATTTGGTCGTAGACCCGAAACCAGGTGATCTACCCTTGGTCAGGTT
GAAGTTCAGGTAACACTGAATGGAGGACCGAACCGACTTACGTTGAAAAGTGAGCGGATGAACTGAGG
GTAGCGGAGAAATTCCAATCGAACTTGGAGATAGCTGGTTCTCTCCGAAATAGCTTTAGGGCTAGCCT
CAAGTGATGATTATTGGAGGTAGAGCACTGTTTGGACGAGGGGCCCCTCTCGGGTTACCGAATTCAGA
CAAACTCCGAATGCCAATTAATTTAACTTGGGAGTCAGAACATGGGTGATAAGGTCCGTGTTCGAAAG
GGAAACAGCCCAGACCACCAGCTAAGGTCCCAAAATATATGTTAAGTGGAAAAGGATGTGGCGTTGCC
CAGACAACTAGGATGTTGGCTTAGAAGCAGCCATCATTTAAAGAGTGCGTAATAGCTCACTAGTCGAG
TGACACTGCGCCGAAAATGTACCGGGGCTAAACATATTACCGAAGCTGTGGATTGTCCTTTGGACAAT
GGTAGGAGAGCGTTCTAAGGGCGTCGAAGCATGATCGCAAGGACATGTGGAGCGCTTAGAAGTGAGAA
TGCCGGTGTGAGTAGCGAAAGACGGGTGAGAATCCCGTCCACCGATTGACTAAGGTTTCCAGAGGAAG
GCTCGTCCGCTCTGGGTTAGTCGGGTCCTAAGCTGAGGCCGACAGGCGTAGGCGATGGATAACAGGTT
GATATTCCTGTACCACCTAGTATCGTTTTAATCGATGGGGGGACGCAGTAGGATAGGCGAAGCGTGCT
GTTGGAGTGCACGTCCAAGCAGTAAGGCTGAGTGTTAGGCAAATCCGGCACTCATAAGGCTGAGCTGT
GATGGGGAGAGGAAATTGTTTCCTCGAGTCGTTGATTTCACACTGCCGAGAAAAGCCTCTAGATAGAT
AACAGGTGCCCGTACCGCAAACCGACACAGGTAGTCAAGATGAGAATTCTAAGGTGAGCGAGCGAACT
CTCGTTAAGGAACTCGGCAAAATGACCCCGTAACTTCGGGAGAAGGGGTGCTCTTTAGGGTTCACGCC
CAGAAGAGCCGCAGTGAATAGGCCCAAGCGACTGTTTATCAAAAACACAGGTCTCTGCTAAACCGTAA
GGTGATGTATAGGGCTGACGCCTGCCCGGTGCTGGAAGGTTAAGAGGAGTGGTTAGCTTCTGCGAAG
CTACGAATCGAAGCCCCAGTAAACGGCGGCCGTAACTATAACGGTCCTAAGGTAGCGAAATTCCTTGT
CGGGTAAGTTCCGACCCGCACGAAAGGCGTAACGATTTGGGCACTGTCTCAACGAGAGACTCGGTGAA
ATCATAGTACCTGTGAAGATGCAGGTTACCCGCGACAGGACGGAAAGACCCCGTGGAGCTTTACTGTA
GCCTGATATTGAAATTCGGCACAGCTTGTACAGGATAGGTAGGAGCCTTTGAAACGTGAGCGCTAGCT
TACGTGGAGGCGTTGGTGGGATACTACCCTAGCTGTGTTGGCTTTCTAACCCGCACCACTTATCGTGG
TGGGAGACAGTGTCAGGCGGGCAGTTTGACTGGGGCGGTCGCCTCCTAAAAGGTAACGGAGGCGCTCA
AAGGTTCCCTCAGAATGGTTGGAAATCATTCATAGAGTGTAAAGGCATAAGGGAGCTTGACTGCGAGA
CCTACAAGTCGAGCAGGGTCGAAAGACGGACTTAGTGATCCGGTGGTTCCGCATGGAAGGGCCATCGC
TCAACGGATAAAAGCTACCCCGGGGATAACAGGCTTATCTCCCCCAAGAGTTCACATCGACGGGGAGG
TTTGGCACCTCGATGTCGGCTCATCGCATCCTGGGGCTGTAGTCGGTCCCAAGGGTTGGGCTGTTCGC
CCATTAAAGCGGTACGCGAGCTGGGTTCAGAACGTCGTGAGACAGTTCGGTCCCTATCCGTCGTGGGC
GTAGGAAATTTGAGAGGAGCTGTCCTTAGTACGAGAGGACCGGGATGGACATACCTCTGGTGTACCAG
TTGTCGTGCCAACGGCATAGCTGGGTAGCTATGTATGGACGGGATAAGTGCTGAAAGCATCTAAGCAT
GAAGCCCCCCTCAAGATGAGATTTCCCAACTTCGGTTATAAGATCCCTCGAAGATGACGAGGTTAATA
GGTTCGAGGTGGAAGCGTGGTGACACGTGGAGCTGACGAATACTAATCGATCGAAGACTTAATCAA

Figure 16B. *Staphylococcus epidermidis*

Simplified sequence (SEQ ID NO 224)

```
GATTAAGTTATTAAGGGTGTATGGTGGATGTTTTGGTATTAGAAGTTGATGAAGGATGTTATTAATGA
TGATATGTTTTGGGTAGTTGTAAGTAAGTGTTGATTTAGAGATTTTTGAATGGGGAATTTAGTATGA
GTTATGTTATGTTATTGATATGTGAATTTATAGTATGTTAGAAGGTAGATTTGGAGAATTGAAATATT
TTAGTATTTGGAGGAAGAGAAAGAAAAATTGATTTTTTGAGTAGTGGTGAGTGAAATGGGAAGAGTTT
AAATTAATAAGTTTGTTTGTTGGGGTTGTAGGATATTTATATGGAGTTATAAAAGAATATGTTAGAT
GAATTATTTGGAAAGATGAATTAAAGAAGGTAATAATTTTGTAGTTGAAAATATATTTTTTTTGAGT
GGATTTTGAGTATGATGGAGTATGTGAAATTTTGTTGGAATTTGGGAGGATTATTTTTTAAGGTTAAA
TATTTTTTAGTGATTGATAGTGAATTAGTATTGTGAGGGAAAGGTGAAAAGTATTTTGGAAGGGGAGT
GAAAGAGAATTTGAAATTGTGTGTTTATAAGTAGTTAGAGTTTGTTAATGGGTGATGGTGTGTTTTTT
GTAGAATGAATTGGTGAGTTATGATTTGATGTAAGGTTAAGTAGTAAATGTGGAGTTGTAGTGAAAGT
GAGTTTGAATAGGGTGTTGAGTATTTGGTTGTAGATTTGAAATTAGGTGATTTATTTTTGGTTAGGTT
GAAGTTTAGGTAATATTGAATGGAGGATTGAATTGATTTATGTTGAAAAGTGAGTGGATGAATTGAGG
GTAGTGGAGAAATTTTAATTGAATTTGGAGATAGTTGGTTTTTTTTGAAATAGTTTTAGGGTTAGTTT
TAAGTGATGATTATTGGAGGTAGAGTATTGTTTGGATGAGGGGTTTTTTTTGGGTTATTGAATTTAGA
TAAATTTTGAATGTTAATTAATTTAATTTGGGAGTTAGAATATGGGTGATAAGGTTTGTGTTTGAAAG
GGAAATAGTTTAGATTATTAGTTAAGGTTTTAAAATATATGTTAAGTGGAAAAGGATGTGGTGTTGTT
TAGATAATTAGGATGTTGGTTTAGAAGTAGTTATTATTTAAAGAGTGTGTAATAGTTTATTAGTTGAG
TGATATTGTGTTGAAAATGTATTGGGGTTAAATATATTATTGAAGTTGTGGATTGTTTTTTGGATAAT
GGTAGGAGAGTGTTTTAAGGGTGTTGAAGTATGATTGTAAGGATATGTGGAGTGTTTAGAAGTGAGAA
TGTTGGTGTGAGTAGTGAAAGATGGGTGAGAATTTTGTTTATTGATTGATTAAGGTTTTTAGAGGAAG
GTTTGTTTGTTTTGGGTTAGTTGGGTTTTAAGTTGAGGTTGATAGGTGTAGGTGATGGATAATAGGTT
GATATTTTGTATTATTTAGTATTGTTTTAATTCATGGGGGGATGTAGTAGGATAGGTGAAGTGTGTT
GTTGGAGTGTATGTTTAAGTAGTAAGGTTGAGTGTTAGGTAAATTTGGTATTTATAAGGTTGAGTTGT
GATGGGAGAGGAAATTGTTTTTTTGAGTTGTTGATTTTATATTGTTGAGAAAGTTTTTAGATAGAT
AATAGGTGTTTGTATTGTAAATTGATATAGGTAGTTAAGATGAGAATTTTAAGGTGAGTGAGTGAATT
TTTGTTAAGGAATTTGGTAAAATGATTTTGTAATTTTGGGAGAAGGGGTGTTTTTTAGGGTTTATGTT
TAGAAGAGTTGTAGTGAATAGGTTTAAGTGATTGTTTATTAAAAATATAGGTTTTTGTTAAATTGTAA
GGTGATGTATAGGGGTTGATGTTTGTTTGGTGTTGGAAGGTTAAGAGGAGTGGTTAGTTTTTGTGAAG
TTATGAATTGAAGTTTTAGTAAATGGTGGTTGTAATTATAATGGTTTTAAGGTAGTGAAATTTTTGT
TGGGTAAGTTTTGATTTGTATGAAAGGTGTAATGATTTGGGTATTGTTTTAATGAGAGATTTGGTGAA
ATTATAGTATTTGTGAAGATGTAGGTTATTTGTGATAGGATGGAAAGATTTTGTGGAGTTTTATTGTA
GTTTGATATTGAAATTTGGTATAGTTTGTATAGGATAGGTAGGAGTTTTTGAAATGTGAGTGTTAGTT
TATGTGGAGGTGTTGGTGGGATATTATTTAGTTGTGTTGGTTTTTAATTTGTATTATTTATTGTGG
TGGGAGATAGTGTTAGGTGGGTAGTTTGATTGGGGTGGTTGTTTTTAAAAGGTAATGGAGGTGTTTA
AAGGTTTTTTTAGAATGGTTGGAAATTATTTATAGAGTGTAAAGGTATAAGGGAGTTTGATTGTGAGA
TTTATAAGTTGAGTAGGGTTGAAAGATGGATTTAGTGATTTGGTGGTTTTGTATGGAAGGGTTATTGT
TTAATGGATAAAAGTTATTTTGGGGATAATAGGTTTATTTTTTTAAGAGTTTATATTGATGGGGAGG
TTTGGTATTTTCATGTTGGTTTATTGTATTTGGGGTTGTAGTTGGTTTTAAGGGTTGGGTTGTTTGT
TTATTAAAGTGGTATGTGAGTTGGGTTTAGAATGTTGTGAGATAGTTTGGTTTTATTTGTTGTGGGT
GTAGGAAATTTGAGAGGAGTTGTTTTAGTATGAGAGGATTGGGATGGATATATTTTGGTGTATTAG
TTGTTGTGTTAATGGTATAGTTGGGTAGTTATGTATGGATGGGATAAGTGTTGAAAGTATTTAAGTAT
GAAGTTTTTTTTAAGATGAGATTTTTTAATTTTGGTTATAAGATTTTTTGAAGATGATGAGGTTAATA
GGTTTGAGGTGGAAGTGTGGTGATATGTGGAGTTGATGAATATTAATTGATTGAAGATTTAATTAA
```

Figure 17A  *E. coli* recA gene

Normal Sequence (SEQ ID NO 225)

ATGGCTATCGACGAAAACAAACAGAAAGCGTTGGCGGCAGCACTGGGCCAGATTGAGAAACAATTTGG
TAAAGGCTCCATCATGCGCCTGGGTGAAGACCGTTCCATGGATGTGGAAACCATCTCTACCGGTTCGC
TTTCACTGGATATCGCGCTTGGGGCAGGTGGTCTGCCGATGGGCCGTATCGTCGAAATCTACGGACCG
GAATCTTCCGGTAAAACCACGCTGACGCTGCAGGTGATCGCCGCAGCGCAGCGTGAAGGTAAAACCTG
TGCGTTTATCGATGCTGAACACGCGCTGGACCCAATCTACGCACGTAAACTGGGCGTCGATATCGATA
ACCTGCTGTGCTCCCAGCCGGACACCGGCGAGCAGGCACTGGAAATCTGTGACGCCCTGGCGCGTTCT
GGCGCAGTAGACGTTATCGTCGTTGACTCCGTGGCGGCACTGACGCCGAAAGCGGAAATCGAAGGCGA
AATCGGCGACTCTCACATGGGCCTTGCGGCACGTATGATGAGCCAGGCGATGCGTAAGCTGGCGGGTA
ACCTGAAGCAGTCCAACACGCTGCTGATCTTCATCAACCAGATCCGTATGAAAATTGGTGTGATGTTC
GGTAACCCGGAAACCACTACCGGTGGTAACGCGCTGAAATTCTACGCCTCTGTTCGTCTCGACATCCG
TCGTATCGGCGCGGTGAAAGAGGGCGAAAACGTGGTGGGTAGCGAAACCCGCGTGAAAGTGGTGAAGA
ACAAAATCGCTGCGCCGTTTAAACAGGCTGAATTCCAGATCCTCTACGGCGAAGGTATCAACTTCTAC
GGCGAACTGGTTGACCTGGGCGTAAAAGAGAAGCTGATCGAGAAAGCAGGCGCGTGGTACAGCTACAA
AGGTGAGAAGATCGGTCAGGGTAAAGCGAATGCGACTGCCTGGCTGAAAGATAACCCGGAAACCGCGA
AAGAGATCGAGAAGAAAGTACGTGAGTTGCTGCTGAGCAACCCGAACTCAACGCCGGATTTCTCTGTA
GATGATAGCGAAGGCGTAGCAGAAACTAACGAAGATTTTTAA

Figure 17B  *E. coli* recA gene

Simplified sequence (SEQ ID NO 226)

ATGGTTATTGATGAAAATAAATAGAAAGTGTTGGTGGTAGTATTGGGTTAGATTGAGAAATAATTTGG
TAAAGGTTTTATTATGTGTTTGGGTGAAGATTGTTTATGGATGTGGAATTATTTTATTGGTTTGT
TTTTATTGGATATTGTGTTTGGGGTAGGTGGTTTGTTGATGGGTTGTATTGTTGAAATTTATGGATTG
GAATTTTTTGGTAAAATTATGTTGATGTTGTAGGTGATTGTTGTAGTGTAGTGTGAAGGTAAAATTTG
TGTGTTTATTGATGTTGAATATGTGTTGGATTTAATTTATGTATGTAAATTGGGTGTTGATATTGATA
ATTTGTTGTGTTTTTAGTTGGATATTGGTGAGTAGGTATTGGAAATTTGTGATGTTTTGGTGTGTTTT
GGTGTAGTAGATGTTATTGTTGTTGATTTTGTGGTGGTATTGATGTTGAAAGTGGAAATTGAAGGTGA
AATTGGTGATTTTTATATGGGTTTTGTGGTATGTATGATGAGTTAGGTGATGTGTAAGTTGGTGGGTA
ATTTGAAGTAGTTTAATATGTTGTTGATTTTTATTAATTAGATTTGTATGAAAATTGGTGTGATGTTT
GGTAATTTGGAAATTATTATTGGTGGTAATGTGTTGAAATTTATGTTTTTGTTTGTTTTGATATTTG
TTGTATTGGTGTGGTGAAAGAGGGTGAAATGTGGTGGGTAGTGAAATTTGTGTGAAAGTGGTGAAGA
ATAAAATTGTTGTGTTGTTTAAATAGGTTGAATTTTAGATTTTTATGGTGAAGGTATTAATTTTTAT
GGTGAATTGGTTGATTTGGGTGTAAAAGAGAAGTTGATTGAGAAAGTAGGTGTGTGGTATAGTTATAA
AGGTGAGAAGATTGGTTAGGGTAAAGTGAATGTGATTGTTTGGTTGAAAGATAATTTGGAAATTGTGA
AAGAGATTGAGAAGAAAGTATGTGAGTTGTTGTTGAGTAATTTGAATTTAATGTTGGATTTTTTTGTA
GATGATAGTGAAGGTGTAGTAGAAATTAATGAAGATTTTTAA

SEQUENCE LISTING

<160> NUMBER OF SEQ ID NOS: 226

<210> SEQ ID NO 1
<211> LENGTH: 14
<212> TYPE: DNA
<213> ORGANISM: Artificial Sequence
<220> FEATURE:
<223> OTHER INFORMATION: Oligonucleotide primer

```
<400> SEQUENCE: 1
atatatatat atat                                                    14

<210> SEQ ID NO 2
<211> LENGTH: 14
<212> TYPE: DNA
<213> ORGANISM: Artificial Sequence
<220> FEATURE:
<223> OTHER INFORMATION: Oligonucleotide primer

<400> SEQUENCE: 2
aaaaaaattt tttt                                                    14

<210> SEQ ID NO 3
<211> LENGTH: 34
<212> TYPE: DNA
<213> ORGANISM: Neisseria gonorrhoeae

<400> SEQUENCE: 3
gyaatywagg ycgyctygaa gaytayaaya tggc                              34

<210> SEQ ID NO 4
<211> LENGTH: 34
<212> TYPE: DNA
<213> ORGANISM: Artificial Sequence
<220> FEATURE:
<223> OTHER INFORMATION: Oligonucleotide primer

<400> SEQUENCE: 4
gtaattwagg ttgttttgaa gattataata tggt                              34

<210> SEQ ID NO 5
<211> LENGTH: 16
<212> TYPE: DNA
<213> ORGANISM: Artificial Sequence
<220> FEATURE:
<223> OTHER INFORMATION: Oligonucleotide primer

<400> SEQUENCE: 5
aggycgycty gaagay                                                  16

<210> SEQ ID NO 6
<211> LENGTH: 16
<212> TYPE: DNA
<213> ORGANISM: Artificial Sequence
<220> FEATURE:
<223> OTHER INFORMATION: Oligonucleotide primer

<400> SEQUENCE: 6
aggttgtttt gaagat                                                  16

<210> SEQ ID NO 7
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 7 ggttttttt gaaatagttt tagggtta                                      28

<210> SEQ ID NO 8
<211> LENGTH: 28
<212> TYPE: DNA
<213> ORGANISM: Artificial Sequence
```

```
<220> FEATURE:
<223> OTHER INFORMATION: Oligonucleotide primer

<400> SEQUENCE: 8 ggttttttt gaaarttatt taggtagt                                    28

<210> SEQ ID NO 9
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 9
tggkagttag awtgtgrrwg ataag                                      25

<210> SEQ ID NO 10
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 10
tgggagatak atrgtgggtg ttaat                                      25

<210> SEQ ID NO 11
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 11
ggatgtggdr ttktkwagat aa                                         22

<210> SEQ ID NO 12
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 12
tgawgtggga aggtwtagat ag                                         22

<210> SEQ ID NO 13
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 13
hcaatmhhac ttcammmcmm yt                                         22

<210> SEQ ID NO 14
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 14
wcaahhcacc ttcahmaacy tac                                        23
```

<210> SEQ ID NO 15
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 15
accaacattc tcactymtaa wmamtccac                                    29

<210> SEQ ID NO 16
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 16
atcaacattc acacttctaa tacctccaa                                    29

<210> SEQ ID NO 17
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 17
ggttttttty gaaatagttt tagggtta                                     28

<210> SEQ ID NO 18
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 18
ggttttttty gaaarttatt taggtagt                                     28

<210> SEQ ID NO 19
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 19
yggkagttag awygygrrwg ataag                                        25

<210> SEQ ID NO 20
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 20
ygggagatak ayrgygggtg ttaat                                        25

<210> SEQ ID NO 21
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 21
ggatgtggdr ttkykwagat aa                                              22

<210> SEQ ID NO 22
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 22
ygawgtggga aggtwtagat ag                                              22

<210> SEQ ID NO 23
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 23
hcratmhhrc ttcrmmmcmm yt                                              22

<210> SEQ ID NO 24
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 24
wcrahhcacc ttcahmracy tac                                             23

<210> SEQ ID NO 25
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 25
accracattc tcactymtaa wmamtccac                                       29

<210> SEQ ID NO 26
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 26
atcaacattc rcacttctaa tacctccaa                                       29

<210> SEQ ID NO 27
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 27
kttragaaaa gtwtttagdd agrk                                            24

<210> SEQ ID NO 28

<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 28
tttargaaaa gttwttaagt wtta                                            24

<210> SEQ ID NO 29
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 29
agdtragrwg agdattttwa ggtkr                                           25

<210> SEQ ID NO 30
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 30
ggktrggwwg agaatwttaa ggtgt                                           25

<210> SEQ ID NO 31
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 31
aatytmymat taaaacaata cmcaa                                           25

<210> SEQ ID NO 32
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 32
aatctcaaaw aaaaacaaym ymacc                                           25

<210> SEQ ID NO 33
<211> LENGTH: 32
<212> TYPE: DNA
<213> ORGANISM: Artificial Sequence
<220> FEATURE:
<223> OTHER INFORMATION: Oligonucleotide primer

<400> SEQUENCE: 33
acmhacatct tcacwmayay tayaayttca cc                                   32

<210> SEQ ID NO 34
<211> LENGTH: 32
<212> TYPE: DNA
<213> ORGANISM: Artificial Sequence
<220> FEATURE:
<223> OTHER INFORMATION: Oligonucleotide primer

<400> SEQUENCE: 34

```
maytacatct tcacaacmah wtcaayttca ct                          32

<210> SEQ ID NO 35
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 35
cmatayyaaa ytacaataaa actc                                   24

<210> SEQ ID NO 36
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 36
caataymaaa ctayaataaa aatt                                   24

<210> SEQ ID NO 37
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 37
ggtgaarttr tartrtkwgt gaagatgtdk g                           31

<210> SEQ ID NO 38
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 38
agtgaarttg awdtkgttgt gaagatgtar t                           31

<210> SEQ ID NO 39
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 39
gatwggatgg aaagattttr trgag                                  25

<210> SEQ ID NO 40
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 40
kgtwagatgg aaagattttg tgaat                                  25

<210> SEQ ID NO 41
<211> LENGTH: 23
<212> TYPE: DNA
```

<210> SEQ ID NO 41
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 41
hymaymmway haaaataata tcc                                              23

<210> SEQ ID NO 42
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 42
tcaammmywm maaaataata ttt                                              23

<210> SEQ ID NO 43
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 43
awccattcta aaaaaacctt taaaca                                           26

<210> SEQ ID NO 44
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 44
aaccawwmyw aamhmacctt cawact                                           26

<210> SEQ ID NO 45
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 45
gttggtaagg tgatatgaat tgttataa                                         28

<210> SEQ ID NO 46
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 46
ttattattaa ttgaatttat aggtta                                           26

<210> SEQ ID NO 47
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 47
gaggagttta gagtttgaat tagtrtg                                          27

<210> SEQ ID NO 48
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 48
tatatacaaa actatcaccc tatatc                                        26

<210> SEQ ID NO 49
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 49
tcatcaaact cacaacayat ac                                            22

<210> SEQ ID NO 50
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 50
ttgagtaaga tattgatggg ggtaa                                         25

<210> SEQ ID NO 51
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 51
tatggttagg gggttattgt a                                             21

<210> SEQ ID NO 52
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 52
aatctatcat ttaaaacctt aacc                                          24

<210> SEQ ID NO 53
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 53
cctaactatc tataccttcc cact                                          24

<210> SEQ ID NO 54
<211> LENGTH: 25
<212> TYPE: DNA
<213> ORGANISM: Artificial Sequence
<220> FEATURE:

```
<223> OTHER INFORMATION: Oligonucleotide primer

<400> SEQUENCE: 54
cactccccta ccataccaat aaacc                                         25

<210> SEQ ID NO 55
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 55
gtatgatgag ttagggagtt aagttaaa                                      28

<210> SEQ ID NO 56
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 56
ggtgaggtta agggatatat a                                             21

<210> SEQ ID NO 57
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 57
aaaagagtga agagttgttt ggtttagata                                    30

<210> SEQ ID NO 58
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 58
tccaaacctt tttcaacatt aact                                          24

<210> SEQ ID NO 59
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 59
ccctaaaatt atttcaaaaa aaacaaaa                                      28

<210> SEQ ID NO 60
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 60
ttagtggggg tttattggtt tattaatgga                                    30
```

```
<210> SEQ ID NO 61
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 61
taaggaagtg atgatttgaa gatagttgga                                    30

<210> SEQ ID NO 62
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 62
acaccttctc tactaaatac t                                             21

<210> SEQ ID NO 63
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 63
tataccataa atcttcacta atatc                                         25

<210> SEQ ID NO 64
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 64
ttgtgtagat gatggagtag taggtta                                       27

<210> SEQ ID NO 65
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 65
gaatgatgga gtaagttaag tatgtgga                                      28

<210> SEQ ID NO 66
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 66
taaaaattat ttcttaaaaa cctcact                                       27

<210> SEQ ID NO 67
<211> LENGTH: 26
<212> TYPE: DNA
<213> ORGANISM: Artificial Sequence
<220> FEATURE:
<223> OTHER INFORMATION: Oligonucleotide primer
```

```
<400> SEQUENCE: 67
aaattatctc acacacctta aaatat                                           26

<210> SEQ ID NO 68
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 68
aatgttaaaa ggttaaaggg atat                                             24

<210> SEQ ID NO 69
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 69
tattgaattt aagttttggt gaatggtt                                         28

<210> SEQ ID NO 70
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 70
ccaatatttc aacattaact cccactctc                                        29

<210> SEQ ID NO 71
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 71
atatccatct tccaaattca taaaataat                                        29

<210> SEQ ID NO 72
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 72
taaacaacaa caattccact ttcc                                             24

<210> SEQ ID NO 73
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 73
ataggaaaag aaawtgaawg wgattttg                                         28

<210> SEQ ID NO 74
<211> LENGTH: 28
```

```
<212> TYPE: DNA
<213> ORGANISM: Artificial Sequence
<220> FEATURE:
<223> OTHER INFORMATION: Oligonucleotide primer

<400> SEQUENCE: 74
gtgtagtggt gagtgaaagt ggaatagg                                          28

<210> SEQ ID NO 75
<211> LENGTH: 32
<212> TYPE: DNA
<213> ORGANISM: Artificial Sequence
<220> FEATURE:
<223> OTHER INFORMATION: Oligonucleotide primer

<400> SEQUENCE: 75
taaacaamtt cmmtcaaaat aacatttyyc aa                                     32

<210> SEQ ID NO 76
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 76
ctaattaata tttaaactta ccc                                               23

<210> SEQ ID NO 77
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 77
ttttgaaatt atatgtttat aatgt                                             25

<210> SEQ ID NO 78
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 78
aagtatgagt tggtgagtta tgatagt                                           27

<210> SEQ ID NO 79
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 79
cctccamtta wtyataatct yac                                               23

<210> SEQ ID NO 80
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 80
```

```
caccwaaaya acaccatcat acatt                                      25
```

<210> SEQ ID NO 81
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 81

```
tgtagttaga tagtggggta taagttta                                   29
```

<210> SEQ ID NO 82
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 82

```
aggggaagag tttagattat taaa                                       24
```

<210> SEQ ID NO 83
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 83

```
ataacttcaw cycmwataca acactcat                                   28
```

<210> SEQ ID NO 84
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 84

```
atcaatttaa aaaattctca ctcycaaa                                   28
```

<210> SEQ ID NO 85
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 85

```
tttttatwat tggatttggg gwtaaa                                     26
```

<210> SEQ ID NO 86
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 86

```
tkktwwttag tattgagaat ga                                         22
```

<210> SEQ ID NO 87
<211> LENGTH: 24
<212> TYPE: DNA
<213> ORGANISM: Artificial Sequence

```
<220> FEATURE:
<223> OTHER INFORMATION: Oligonucleotide primer

<400> SEQUENCE: 87
tgtaaattwa ttttgtaagt twgt                                    24

<210> SEQ ID NO 88
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 88
gaatgagggg ggattgttta att                                     23

<210> SEQ ID NO 89
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 89
tctataacca aaacaatcaa aaaata                                  26

<210> SEQ ID NO 90
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 90 cattcacct aacaaatatc ttcacc                                   26

<210> SEQ ID NO 91
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 91
atwwataggt tgaataggtr agaaat                                  26

<210> SEQ ID NO 92
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 92
atagtgattt ggtggtttag tatggaat                                28

<210> SEQ ID NO 93
<211> LENGTH: 32
<212> TYPE: DNA
<213> ORGANISM: Artificial Sequence
<220> FEATURE:
<223> OTHER INFORMATION: Oligonucleotide primer

<400> SEQUENCE: 93
caaacctact tcaactcaaa aataaaataa at                           32
```

```
<210> SEQ ID NO 94
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 94
acaacaattt aaacccaact cacatatct                                    29

<210> SEQ ID NO 95
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 95
aaaayaamwc tyttcaatct tcctayaaa                                    29

<210> SEQ ID NO 96
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 96
atwwttgtta aggdwrtgar raggaag                                      27

<210> SEQ ID NO 97
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 97
tagragggta aattgargwg ttta                                         24

<210> SEQ ID NO 98
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 98
tkatttggga arrtwrgtta aagaga                                       26

<210> SEQ ID NO 99
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 99
tctcttcaac ttaacctcac atcat                                        25

<210> SEQ ID NO 100
<211> LENGTH: 24
<212> TYPE: DNA
<213> ORGANISM: Artificial Sequence
<220> FEATURE:
<223> OTHER INFORMATION: Oligonucleotide primer
```

<400> SEQUENCE: 100
ataatttcaa atctacawcm waat                                    24

<210> SEQ ID NO 101
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 101
ratktattgg aggattgaat taggg                                   25

<210> SEQ ID NO 102
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 102
atgttgaaaa gtgtttggat gat                                     23

<210> SEQ ID NO 103
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 103
tctaaaatya ataawccaaa ataamcccct c                            31

<210> SEQ ID NO 104
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 104
actaccaayh atawhtcatt aac                                     23

<210> SEQ ID NO 105
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 105
aggttgakat ttttgtatta gagta                                   25

<210> SEQ ID NO 106
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 106
rwagtgatgg agggatgtag taggttaat                               29

<210> SEQ ID NO 107

```
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 107
cttttctyaa caatataaca tcact                                          25

<210> SEQ ID NO 108
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 108
ctctcamtca cctaaaacta ctca                                           24

<210> SEQ ID NO 109
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 109
agaagttgat gaaggatgtt attaatga                                       28

<210> SEQ ID NO 110
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 110
gttattgata tgtgaatwta tagtatrtt                                      29

<210> SEQ ID NO 111
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 111
caaaaythtt accttctyta atyc                                           24

<210> SEQ ID NO 112
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 112
caacaaaatt ycacatactc cat                                            23

<210> SEQ ID NO 113
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 113
```

```
gatttgatgt aaggttaagt agt                                              23

<210> SEQ ID NO 114
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 114
ttggttaggt tgaagtttag gtaatattga a                                     31

<210> SEQ ID NO 115
<211> LENGTH: 32
<212> TYPE: DNA
<213> ORGANISM: Artificial Sequence
<220> FEATURE:
<223> OTHER INFORMATION: Oligonucleotide primer

<400> SEQUENCE: 115
gatttatgtt gaaaagtgag tggatgaatt ga                                    32

<210> SEQ ID NO 116
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 116
cctytttcta actcccaaat taaattaat                                        29

<210> SEQ ID NO 117
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 117
gaagttgtgg attgtttttt ggata                                            25

<210> SEQ ID NO 118
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 118
aagggtgttg aagtatgatt gtaaggatat                                       30

<210> SEQ ID NO 119
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 119
tacamtccaa ymacacactt cacctatcct a                                     31

<210> SEQ ID NO 120
<211> LENGTH: 26
<212> TYPE: DNA
```

```
<213> ORGANISM: Artificial Sequence
<220> FEATURE:
<223> OTHER INFORMATION: Oligonucleotide primer

<400> SEQUENCE: 120
caacaatata aaatcaacaa ctcaaa                                               26

<210> SEQ ID NO 121
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 121
aggagtggtt agttttttgtg aagtta                                              26

<210> SEQ ID NO 122
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 122
acaaattaaa aawccaacac aact                                                 24

<210> SEQ ID NO 123
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 123
taacactatc tcccaccaya atmaat                                               26

<210> SEQ ID NO 124
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 124
taggttgttg agttttaatt ata                                                  23

<210> SEQ ID NO 125
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 125
gaagtataaa gtaatggtgg ggtg                                                 24

<210> SEQ ID NO 126
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 126
tacaatatca actacaccac ttctaacaaa t                                         31
```

```
<210> SEQ ID NO 127
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 127
taataaaaat aacaattata ttt                                              23

<210> SEQ ID NO 128
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 128
aaggttgtag agtattaagt attttaag                                         28

<210> SEQ ID NO 129
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 129
gttgataatg tattaggggt tgga                                             24

<210> SEQ ID NO 130
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 130
atatggattt gaaagtttag gtaagatg                                         28

<210> SEQ ID NO 131
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 131
tactactaaa tcaacaacaa caatatccac a                                     31

<210> SEQ ID NO 132
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 132
cttaatactt aaaacattaa tct                                              23

<210> SEQ ID NO 133
<211> LENGTH: 27
<212> TYPE: DNA
<213> ORGANISM: Artificial Sequence
<220> FEATURE:
```

```
<223> OTHER INFORMATION: Oligonucleotide primer

<400> SEQUENCE: 133
gagaataagt aaaaggtgtt agttgtg                                              27

<210> SEQ ID NO 134
<211> LENGTH: 34
<212> TYPE: DNA
<213> ORGANISM: Artificial Sequence
<220> FEATURE:
<223> OTHER INFORMATION: Oligonucleotide primer

<400> SEQUENCE: 134
gatttttatt ggtttattgt tatttgatat tgtt                                      34

<210> SEQ ID NO 135
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 135
caaataatca atatcaacac ccaactttt c                                          31

<210> SEQ ID NO 136
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 136
tacacaccac caaacccata tac                                                  23

<210> SEQ ID NO 137
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 137
gaaaataaat agaaagtgtt ggtg                                                 24

<210> SEQ ID NO 138
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 138 tgttttatt ggatattgtg ttt                                                   23

<210> SEQ ID NO 139
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 139
caataacatc tactacacca aaacac                                               26
```

<210> SEQ ID NO 140
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 140
catattaaac tacttcaaat taccc                                          25

<210> SEQ ID NO 141
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 141
tatgtgtttt ggtgaagatt gttta                                          25

<210> SEQ ID NO 142
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 142
ttttgatatt gtattggggg tg                                             22

<210> SEQ ID NO 143
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 143
ggtttgttaa tggggtgtat tgttgag                                        27

<210> SEQ ID NO 144
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 144
catactctac atcaataaaa                                                20

<210> SEQ ID NO 145
<211> LENGTH: 34
<212> TYPE: DNA
<213> ORGANISM: Artificial Sequence
<220> FEATURE:
<223> OTHER INFORMATION: Oligonucleotide primer

<400> SEQUENCE: 145
gtaatcaagg tcgtcttgaa gactacaaca tggc                                34

<210> SEQ ID NO 146
<211> LENGTH: 34
<212> TYPE: DNA
<213> ORGANISM: Artificial Sequence
<220> FEATURE:
<223> OTHER INFORMATION: Oligonucleotide primer

```
<400> SEQUENCE: 146
gcaatttagg ccgcctcgaa gattataata tggc                              34

<210> SEQ ID NO 147
<211> LENGTH: 34
<212> TYPE: DNA
<213> ORGANISM: Artificial Sequence
<220> FEATURE:
<223> OTHER INFORMATION: Oligonucleotide primer

<400> SEQUENCE: 147
gtaattaagg ttgttttgaa gattataata tggt                              34

<210> SEQ ID NO 148
<211> LENGTH: 34
<212> TYPE: DNA
<213> ORGANISM: Artificial Sequence
<220> FEATURE:
<223> OTHER INFORMATION: Oligonucleotide primer

<400> SEQUENCE: 148
gtaatttagg ttgttttgaa gattataata tggt                              34

<210> SEQ ID NO 149
<211> LENGTH: 16
<212> TYPE: DNA
<213> ORGANISM: Artificial Sequence
<220> FEATURE:
<223> OTHER INFORMATION: Oligonucleotide primer

<400> SEQUENCE: 149
aggycgycty gaagay                                                  16

<210> SEQ ID NO 150
<211> LENGTH: 16
<212> TYPE: DNA
<213> ORGANISM: Artificial Sequence
<220> FEATURE:
<223> OTHER INFORMATION: Oligonucleotide primer

<400> SEQUENCE: 150
aggttgtttt gaagat                                                  16

<210> SEQ ID NO 151
<211> LENGTH: 16
<212> TYPE: DNA
<213> ORGANISM: Artificial Sequence
<220> FEATURE:
<223> OTHER INFORMATION: Oligonucleotide primer

<400> SEQUENCE: 151
taactacgga agatca                                                  16

<210> SEQ ID NO 152
<211> LENGTH: 16
<212> TYPE: DNA
<213> ORGANISM: Artificial Sequence
<220> FEATURE:
<223> OTHER INFORMATION: Oligonucleotide primer

<400> SEQUENCE: 152
taattatgga agatta                                                  16

<210> SEQ ID NO 153
<211> LENGTH: 16
```

```
<212> TYPE: DNA
<213> ORGANISM: Artificial Sequence
<220> FEATURE:
<223> OTHER INFORMATION: Oligonucleotide primer

<400> SEQUENCE: 153
gtaatcaagg tcgtct                                                    16

<210> SEQ ID NO 154
<211> LENGTH: 16
<212> TYPE: DNA
<213> ORGANISM: Artificial Sequence
<220> FEATURE:
<223> OTHER INFORMATION: Oligonucleotide primer

<400> SEQUENCE: 154
gtaattaagg ttgttt                                                    16

<210> SEQ ID NO 155
<211> LENGTH: 16
<212> TYPE: DNA
<213> ORGANISM: Artificial Sequence
<220> FEATURE:
<223> OTHER INFORMATION: Oligonucleotide primer

<400> SEQUENCE: 155
gcaatttagg ccgcct                                                    16

<210> SEQ ID NO 156
<211> LENGTH: 16
<212> TYPE: DNA
<213> ORGANISM: Artificial Sequence
<220> FEATURE:
<223> OTHER INFORMATION: Oligonucleotide primer

<400> SEQUENCE: 156
gtaatttagg ttgttt                                                    16

<210> SEQ ID NO 157
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 157
aagctcttga aggtgactct aaatacgaag acatcatcat                          40

<210> SEQ ID NO 158
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 158
aagcccttga aggtgacact aaatacgaag acatcgttat                          40

<210> SEQ ID NO 159
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 159
```

-continued aagctcttga aggtgactca aaatacgaag atatcatcat 40

```
<210> SEQ ID NO 160
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 160
```
aagctcttga aggtgatact aagtacgaag acatcatcat 40

```
<210> SEQ ID NO 161
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 161
```
aagctcttga aggtgactct aaatacgaag atatcatcat 40

```
<210> SEQ ID NO 162
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 162
```
aagctcttga aggcgataca gcacatgaag atatcatcat 40

```
<210> SEQ ID NO 163
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 163
```
aagctcttga aggtgactct aaatacgaag acatcgttat 40

```
<210> SEQ ID NO 164
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 164
```
aagctcttga aggtgacact cagtacgaag atatcatcat 40

```
<210> SEQ ID NO 165
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 165
```
aagctcttga aggtgattct aaatacgaag acatcatcat 40

```
<210> SEQ ID NO 166
<211> LENGTH: 40
<212> TYPE: DNA
<213> ORGANISM: Artificial Sequence
```

```
<220> FEATURE:
<223> OTHER INFORMATION: Oligonucleotide primer

<400> SEQUENCE: 166
aagctcttga aggtgattct aaatacgaag acatcatcat                    40

<210> SEQ ID NO 167
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 167
aagcycttga aggygaywcw vmryaygaag ayatcrtyat                    40

<210> SEQ ID NO 168
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 168
aagtttttga aggtgatttt aaatatgaag atattattat                    40

<210> SEQ ID NO 169
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 169
aagtttttga aggtgatatt aaatatgaag atattgttat                    40

<210> SEQ ID NO 170
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 170
aagtttttga aggtgattta aaatatgaag atattattat                    40

<210> SEQ ID NO 171
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 171
aagtttttga aggtgatatt aagtatgaag atattattat                    40

<210> SEQ ID NO 172
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 172
aagtttttga aggtgatttt aaatatgaag atattattat                    40
```

<210> SEQ ID NO 173
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 173
aagtttttga aggtgatata gtatatgaag atattattat                        40

<210> SEQ ID NO 174
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 174
aagtttttga aggtgatttt aaatatgaag atattgttat                        40

<210> SEQ ID NO 175
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 175
aagtttttga aggtgatatt tagtatgaag atattattat                        40

<210> SEQ ID NO 176
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 176
aagtttttga aggtgatttt aaatatgaag atattattat                        40

<210> SEQ ID NO 177
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 177
aagtttttga aggtgatttt aaatatgaag atattattat                        40

<210> SEQ ID NO 178
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 178
aagtttttga aggtgatwtw rwrtatgaag atattrttat                        40

<210> SEQ ID NO 179
<211> LENGTH: 23
<212> TYPE: DNA
<213> ORGANISM: Artificial Sequence
<220> FEATURE:
<223> OTHER INFORMATION: Oligonucleotide primer

```
<400> SEQUENCE: 179
tacaacgaca ataaaacggt tga                                          23

<210> SEQ ID NO 180
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 180
tataatgata ataaaatggt tga                                          23

<210> SEQ ID NO 181
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 181
tacggagata ataagttgt tga                                           23

<210> SEQ ID NO 182
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 182
tatggagata ataagttgt tga                                           23

<210> SEQ ID NO 183
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 183
tacaacgaca ataaaacggt tga                                          23

<210> SEQ ID NO 184
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 184
tataatgata ataaaatggt tga                                          23

<210> SEQ ID NO 185
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 185
tacaacgaca ataaaacggt tga                                          23

<210> SEQ ID NO 186
```

```
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 186
tataatgata ataaaatggt tga                                         23

<210> SEQ ID NO 187
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 187
tatagagata ataaaacgat taa                                         23

<210> SEQ ID NO 188
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 188
tatagagata ataaaatgat taa                                         23

<210> SEQ ID NO 189
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 189
tacagagata ataaaactat taa                                         23

<210> SEQ ID NO 190
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 190
tatagagata ataaaattat taa                                         23

<210> SEQ ID NO 191
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 191
tacaatgaca ataaaatggt tga                                         23

<210> SEQ ID NO 192
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 192
```

-continued

```
tataatgata ataaaatggt tga                                          23

<210> SEQ ID NO 193
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 193
tayrrhgaya ataaarykrt tra                                          23

<210> SEQ ID NO 194
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 194
tatrrwgata ataaartkrt tra                                          23

<210> SEQ ID NO 195
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 195
tgtgtgtgca gggataattg                                              20

<210> SEQ ID NO 196
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 196
tgtatatgta gggacaattg                                              20

<210> SEQ ID NO 197
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 197
tgtgtttgta gagacaactg                                              20

<210> SEQ ID NO 198
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 198
tgtatatgta gggacaattg                                              20

<210> SEQ ID NO 199
<211> LENGTH: 20
<212> TYPE: DNA
```

```
<213> ORGANISM: Artificial Sequence
<220> FEATURE:
<223> OTHER INFORMATION: Oligonucleotide primer

<400> SEQUENCE: 199
tgtgtttgca gagataattg                                                    20

<210> SEQ ID NO 200
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 200
tgcatttgca gggacaattg                                                    20

<210> SEQ ID NO 201
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 201
tgcacttgca gggataattg                                                    20

<210> SEQ ID NO 202
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 202
tgcgtttgcc gagataattg                                                    20

<210> SEQ ID NO 203
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 203
tgtgcctgta gagataacag                                                    20

<210> SEQ ID NO 204
<211> LENGTH: 20
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: 6
<223> OTHER INFORMATION: n = a, c, t, or g

<400> SEQUENCE: 204
tgyryntgym grgayaaywg                                                    20

<210> SEQ ID NO 205
<211> LENGTH: 20
<212> TYPE: DNA
<213> ORGANISM: Artificial Sequence
<220> FEATURE:
<223> OTHER INFORMATION: Oligonucleotide primer
```

<400> SEQUENCE: 205
tgtgtgtgta gggataattg          20

<210> SEQ ID NO 206
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 206
tgtatatgta gggataattg          20

<210> SEQ ID NO 207
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 207
tgtgtttgta gagataattg          20

<210> SEQ ID NO 208
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 208
tgtatatgta gggataattg          20

<210> SEQ ID NO 209
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 209
tgtgtttgta gagataattg          20

<210> SEQ ID NO 210
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 210
tgtatttgta gggataattg          20

<210> SEQ ID NO 211
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 211
tgtatttgta gggataattg          20

<210> SEQ ID NO 212

```
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 212
tgtgtttgtt gagataattg                                                    20

<210> SEQ ID NO 213
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 213
tgtgtttgta gagataatag                                                    20

<210> SEQ ID NO 214
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 214
tgtrtdtgtw grgataatwg                                                    20

<210> SEQ ID NO 215
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 215
ctaaattcgc tccgattta                                                     19

<210> SEQ ID NO 216
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 216
ttaaatttgt tttgattta                                                     19

<210> SEQ ID NO 217
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 217
caaaattgac ccagactta                                                     19

<210> SEQ ID NO 218
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 218
```

-continued

```
taaaattgat ttagattta                                                    19

<210> SEQ ID NO 219
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 219
ttaaattcgt taagattca                                                    19

<210> SEQ ID NO 220
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 220
ttaaatttgt taagattta                                                    19

<210> SEQ ID NO 221
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 221
ywaaattsry ymmgaytya                                                    19

<210> SEQ ID NO 222
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 222
twaaattkrt twwgattta                                                    19

<210> SEQ ID NO 223
<211> LENGTH: 2922
<212> TYPE: DNA
<213> ORGANISM: Artificial Sequence
<220> FEATURE:
<223> OTHER INFORMATION: Oligonucleotide primer

<400> SEQUENCE: 223
gattaagtta ttaagggcgc acggtggatg ccttggcact agaagccgat gaaggacgtt        60
actaacgacg atatgctttg ggtagctgta agtaagcgtt gatccagaga tttccgaatg       120
ggggaaccca gcatgagtta tgtcatgtta tcgatatgtg aatttatagc atgtcagaag       180
gcagacccgg agaactgaaa catcttagta cccggaggaa gagaaagaaa atcgattcc        240 ctgagtagcg gcgagcgaaa cgggaagagc ccaaccaac aagcttgctt gttggggttg       300
taggacactc tatacggagt tacaaaagaa catgttagac gaatcatctg gaaagatgaa       360
tcaaagaagg taataatcct gtagtcgaaa acatattctc tcttgagtgg atcctgagta       420
cgacggagca cgtgaaattc cgtcggaatc tgggaggacc atctcctaag gctaaatact       480
ctctagtgac cgatagtgaa ccagtaccgt gagggaaagg tgaaaagtac cccggaaggg       540
```

-continued

```
gagtgaaaga gaacttgaaa ccgtgtgctt acaagtagtc agagcccgtt aatgggtgat    600
ggcgtgcctt ttgtagaatg aaccggcgag ttacgatctg atgcaaggtt aagcagcaaa    660
tgcggagccg cagcgaaagc gagtctgaat agggcgttga gtatttggtc gtagacccga    720
aaccaggtga tctacccttg gtcaggttga agttcaggta acactgaatg gaggaccgaa    780
ccgacttacg ttgaaaagtg agcggatgaa ctgagggtag cggagaaatt ccaatcgaac    840
ttggagatag ctggttctct ccgaaatagc tttagggcta gcctcaagtg atgattattg    900
gaggtagagc actgtttgga cgaggggccc ctctcgggtt accgaattca gacaaactcc    960
gaatgccaat taatttaact tgggagtcag aacatgggta taaggtccg tgttcgaaag    1020
ggaaacagcc cagaccacca gctaaggtcc caaatatat gttaagtgga aaaggatgtg    1080
gcgttgccca gacaactagg atgttggctt agaagcagcc atcatttaaa gagtgcgtaa    1140
tagctcacta gtcgagtgac actgcgccga aaatgtaccg gggctaaaca tattaccgaa    1200
gctgtggatt gtcctttgga caatggtagg agagcgttct aagggcgtcg aagcatgatc    1260
gcaaggacat gtggagcgct tagaagtgag aatgccggtg tgagtagcga aagacgggtg    1320
agaatcccgt ccaccgattg actaaggttt ccagaggaag gctcgtccgc tctgggttag    1380
tcgggtccta agctgaggcc gacaggcgta ggcgatggat aacaggttga tattcctgta    1440
ccacctagta tcgttttaat cgatgggggg acgcagtagg ataggcgaag cgtgctgttg    1500
gagtgcacgt ccaagcagta aggctgagtg ttaggcaaat ccggcactca taaggctgag    1560
ctgtgatggg gagaggaaat tgtttcctcg agtcgttgat ttcacactgc cgagaaaagc    1620
ctctagatag ataacaggtg cccgtaccgc aaaccgacac aggtagtcaa gatgagaatt    1680
ctaaggtgag cgagcgaact ctcgttaagg aactcggcaa aatgacccg taacttcggg    1740
agaaggggtg ctctttaggg ttcacgccca gaagagccgc agtgaatagg cccaagcgac    1800
tgtttatcaa aaacacaggt ctctgctaaa ccgtaaggtg atgtataggg gctgacgcct    1860
gcccggtgct ggaaggttaa gaggagtggt tagcttctgc gaagctacga atcgaagccc    1920
cagtaaacgg cggccgtaac tataacggtc ctaaggtagc gaaattcctt gtcgggtaag    1980
ttccgacccg cacgaaaggc gtaacgattt gggcactgtc tcaacgagag actcggtgaa    2040
atcatagtac ctgtgaagat gcaggttacc cgcgacagga cggaaagacc ccgtggagct    2100
ttactgtagc ctgatattga aattcggcac agcttgtaca ggataggtag gagcctttga    2160
aacgtgagcg ctagcttacg tggaggcgtt ggtgggatac taccctagct gtgttggctt    2220
tctaacccgc accacttatc gtggtgggag acagtgtcag gcgggcagtt tgactggggc    2280
ggtcgcctcc taaaaggtaa cggaggcgct caaaggttcc ctcagaatgg ttggaaatca    2340
ttcatagagt gtaaaggcat aagggagctt gactgcgaga cctacaagtc gagcagggtc    2400
gaaagacgga cttagtgatc cggtggttcc gcatggaagg gccatcgctc aacggataaa    2460
agctaccccg gggataacag gcttatctcc cccaagagtt cacatcgacg gggaggtttg    2520
gcacctcgat gtcggctcat cgcatcctgg ggctgtagtc ggtcccaagg gttgggctgt    2580
tcgcccatta aagcggtacg cgagctgggt tcagaacgtc gtgagacagt tcggtcccta    2640
tccgtcgtgg gcgtaggaaa tttgagagga gctgtcctta gtacgagagg accgggatgg    2700
acatacctct ggtgtaccag ttgtcgtgcc aacggcatag ctgggtagct atgtatggac    2760
gggataagtg ctgaaagcat ctaagcatga agccccctc aagatgagat ttcccaactt    2820
cggttataag atccctcgaa gatgacgagg ttaataggtt cgaggtggaa gcgtggtgac    2880
acgtggagct gacgaatact aatcgatcga agacttaatc aa                      2922
```

<210> SEQ ID NO 224
<211> LENGTH: 2922
<212> TYPE: DNA
<213> ORGANISM: Artificial Sequence
<220> FEATURE:
<223> OTHER INFORMATION: Oligonucleotide primer

<400> SEQUENCE: 224

```
gattaagtta ttaagggtgt atggtggatg ttttggtatt agaagttgat gaaggatgtt      60
attaatgatg atatgttttg ggtagttgta agtaagtgtt gatttagaga tttttgaatg     120
ggggaattta gtatgagtta tgttatgtta ttgatatgtg aatttatagt atgttagaag     180
gtagatttgg agaattgaaa tattttagta tttggaggaa gagaaagaaa aattgatttt     240
ttgagtagtg gtgagtgaaa tgggaagagt ttaaattaat aagtttgttt gttggggttg     300
taggatattt tatatggagt tataaaagaa tatgttagat gaattatttg gaaagatgaa     360
ttaaagaagg taataatttt gtagttgaaa atatattttt ttttgagtgg attttgagta     420
tgatggagta tgtgaaattt tgttggaatt tgggaggatt attttttaag gttaaatatt     480
ttttagtgat tgatagtgaa ttagtattgt gagggaaagg tgaaaagtat tttggaaggg     540
gagtgaaaga gaatttgaaa ttgtgtgttt ataagtagtt agagtttgtt aatgggtgat     600
ggtgtgtttt ttgtagaatg aattggtgag ttatgatttg atgtaaggtt aagtagtaaa     660
tgtggagttg tagtgaaagt gagtttgaat agggtgttga gtatttggtt gtagatttga     720
aattaggtga tttattttg gttaggttga agtttaggta atattgaatg gaggattgaa     780
ttgatttatg ttgaaagtg agtggatgaa ttgagggtag tggagaaatt ttaattgaat     840
ttggagatag ttggttttt ttgaaatagt tttaggggta gttttaagtg atgattattg     900
gaggtagagt attgtttgga tgaggggttt tttttgggtt attgaattta gataaatttt     960
gaatgttaat taatttaatt tgggagttag aatatgggtg ataaggtttg tgtttgaaag    1020
ggaaatagtt tagattatta gttaaggttt taaaatatat gttaagtgga aaaggatgtg    1080
gtgttgttta gataattagg atgttggttt agaagtagtt attatttaaa gagtgtgtaa    1140
tagtttatta gttgagtgat attgtgttga aaatgtattg gggttaaata tattattgaa    1200
gttgtggatt gtttttggga taatggtagg agagtgtttt aagggtgttg aagtatgatt    1260
gtaaggatat gtggagtgtt tagaagtgag aatgttggtg tgagtagtga agatgggtg     1320
agaattttgt ttattgattg attaaggttt ttagaggaag gtttgtttgt tttgggttag    1380
ttgggtttta agttgaggtt gataggtgta ggtgatggat aataggttga tatttttgta    1440
ttatttagta ttgtttttaat tgatgggggg atgtagtagg ataggtgaag tgtgttgttg    1500
gagtgtatgt ttaagtagta aggttgagtg ttaggtaaat ttggtatta taaggttgag    1560
ttgtgatggg gagaggaaat tgttttttg agttgttgat tttatattgt tgagaaaagt     1620
ttttagatag ataataggtg tttgtattgt aaattgatat aggtagttaa gatgagaatt    1680
ttaaggtgag tgagtgaatt tttgttaagg aatttggtaa aatgattttg taattttggg    1740
agaagggtg ttttttaggg tttatgttta gaagagttgt agtgaatagg tttaagtgat    1800
tgttttattaa aaatataggt ttttgttaaa ttgtaaggtg atgtataggg gttgatgttt    1860
gtttggtgtt ggaaggttaa gaggagtggt tagttttgt gaagttatga attgaagttt    1920
tagtaaatgg tggttgtaat tataatggtt ttaaggtagt gaaatttttt gttgggtaag    1980
ttttgatttg tatgaaaggt gtaatgattt gggtattgtt ttaatgagag atttggtgaa    2040
```

-continued

```
attatagtat tgtgaagat gtaggttatt tgtgatagga tggaaagatt tgtggagtt      2100 ttattgtagt ttgatattga aatttggtat agtttgtata ggataggtag gagtttttga    2160
aatgtgagtg ttagtttatg tggaggtgtt ggtgggatat tattttagtt gtgttggttt    2220
tttaatttgt attatttatt gtggtgggag atagtgttag gtgggtagtt tgattggggt    2280
ggttgttttt taaaaggtaa tggaggtgtt taaaggtttt tttagaatgg ttggaaatta    2340
tttatagagt gtaaaggtat aagggagttt gattgtgaga tttataagtt gagtagggtt    2400
gaaagatgga tttagtgatt tggtggtttt gtatggaagg gttattgttt aatggataaa    2460
agttattttg gggataatag gtttattttt tttaagagtt tatattgatg gggaggtttg    2520
gtattttgat gttggtttat tgtattttgg ggttgtagtt ggttttaagg gttgggttgt    2580
ttgtttatta aagtggtatg tgagttgggt ttagaatgtt gtgagatagt ttggttttta    2640
tttgttgtgg gtgtaggaaa tttgagagga gttgttttta gtatgagagg attgggatgg    2700
atatattttt ggtgtattag ttgttgtgtt aatggtatag ttgggtagtt atgtatggat    2760
gggataagtg ttgaaagtat ttaagtatga agttttttttt aagatgagat ttttaatttt    2820
tggttataag atttttttgaa gatgatgagg ttaataggtt tgaggtggaa gtgtggtgat    2880
atgtggagtt gatgaatatt aattgattga agatttaatt aa                      2922
```

`<210>` SEQ ID NO 225
`<211>` LENGTH: 1062
`<212>` TYPE: DNA
`<213>` ORGANISM: Artificial Sequence
`<220>` FEATURE:
`<223>` OTHER INFORMATION: Oligonucleotide primer

`<400>` SEQUENCE: 225

```
atggctatcg acgaaaacaa acagaaagcg ttggcggcag cactgggcca gattgagaaa      60
caatttggta aaggctccat catgcgcctg ggtgaagacc gttccatgga tgtgaaaacc     120
atctctaccg gttcgctttc actggatatc gcgcttgggg caggtggtct gccgatgggc     180
cgtatcgtcg aaatctacgg accggaatct tccggtaaaa ccacgctgac gctgcaggtg     240
atcgccgcag cgcagcgtga aggtaaaacc tgtgcgttta tcgatgctga acacgcgctg     300
gacccaatct acgcacgtaa actgggcgtc gatatcgata acctgctgtg ctcccagccg     360
gacaccggcg agcaggcact ggaaatctgt gacgccctgg cgcgttctgg cgcagtagac     420
gttatcgtcg ttgactccgt ggcggcactg acgccgaaag cggaaatcga aggcgaaatc     480
ggcgactctc acatgggcct tgcggcacgt atgatgagcc aggcgatgcg taagctggcg     540
ggtaacctga agcagtccaa cacgctgctg atcttcatca accagatccg tatgaaaatt     600
ggtgtgatgt tcggtaaccc ggaaaccact accggtggta acgcgctgaa attctacgcc     660
tctgttcgtc tcgacatccg tcgtatcggc gcggtgaaag agggcgaaaa cgtggtgggt     720
agcgaaaccc gcgtgaaagt ggtgaagaac aaaatcgctg cgccgtttaa acaggctgaa     780
ttccagatcc tctacggcga aggtatcaac ttctacggcg aactggttga cctgggcgta     840
aaagagaagc tgatcgagaa agcaggcgcg tggtacagct acaaaggtga aagatcggt      900 cagggtaaag cgaatgcgac tgcctggctg aaagataacc cggaaaccgc gaaagagatc     960
gagaagaaag tacgtgagtt gctgctgagc aacccgaact caacgccgga tttctctgta    1020
gatgatagcg aaggcgtagc agaaactaac gaagatttttt aa                      1062
```

`<210>` SEQ ID NO 226
`<211>` LENGTH: 1062

```
<212> TYPE: DNA
<213> ORGANISM: Artificial Sequence
<220> FEATURE:
<223> OTHER INFORMATION: Oligonucleotide primer

<400> SEQUENCE: 226
atggttattg atgaaaataa atagaaagtg ttggtggtag tattgggtta gattgagaaa      60
taatttggta aaggttttat tatgtgtttg ggtgaagatt gttttatgga tgtggaaatt     120
atttttattg gtttgttttt attggatatt gtgtttgggg taggtggttt gttgatgggt     180
tgtattgttg aaatttatgg attggaattt tttggtaaaa ttatgttgat gttgtaggtg     240
attgttgtag tgtagtgtga aggtaaaatt tgtgtgttta ttgatgttga atatgtgttg     300
gatttaattt atgtatgtaa attgggtgtt gatattgata atttgttgtg ttttttagttg    360 gatattggtg agtaggtatt ggaaatttgt gatgttttgg tgtgttttgg tgtagtagat     420
gttattgttg ttgattttgt ggtggtattg atgttgaaag tggaaattga aggtgaaatt     480
ggtgattttt atatgggttt tgtggtatgt atgatgagtt aggtgatgtg taagttggtg     540
ggtaatttga agtagtttaa tatgttgttg atttttatta attagatttg tatgaaaatt     600
ggtgtgatgt ttggtaattt ggaaattatt attggtggta atgtgttgaa attttatgtt     660
tttgtttgtt ttgatatttg ttgtattggt gtggtgaaag agggtgaaaa tgtggtgggt     720
agtgaaattt gtgtgaaagt ggtgaagaat aaaattgttg tgttgtttaa ataggttgaa     780
ttttagattt tttatggtga aggtattaat ttttatggtg aattggttga tttgggtgta     840
aaagagaagt tgattgagaa agtaggtgtg tggtatagtt ataaaggtga gaagattggt     900
tagggtaaag tgaatgtgat tgtttggttg aaagataatt tggaaattgt gaaagagatt     960
gagaagaaag tatgtgagtt gttgttgagt aatttgaatt taatgttgga ttttttttgta   1020 gatgatagtg aaggtgtagt agaaattaat gaagatttt aa                        1062
```

METHODS FOR SIMPLIFYING MICROBIAL NUCLEIC ACIDS BY CHEMICAL MODIFICATION OF CYTOSINES

TECHNICAL FIELD

The invention relates to nucleic acid detection assays for the detection of microorganisms. The invention also relates to methods for chemical treatment of nucleic acids to reduce the complexity of microbial genomes combined with the use of specific ligands for microbial detection.

BACKGROUND ART

A number of procedures are presently available for the detection of specific nucleic acid molecules. These procedures typically depend on sequence-dependent hybridisation between the target nucleic acid and nucleic acid probes which may range in length from short oligonucleotides (20 bases or less) to sequences of many kilobases (kb).

The most widely used method for amplification of specific sequences from within a population of nucleic acid sequences is that of polymerase chain reaction (PCR) (Dieffenbach, C. and Dveksler, G. eds. PCR Primer: A Laboratory Manual. Cold Spring Harbor Press, Plainview N.Y.). In this amplification method, oligonucleotides, generally 20 to 30 nucleotides in length on complementary DNA strands and at either end of the region to be amplified, are used to prime DNA synthesis on denatured single-stranded DNA. Successive cycles of denaturation, primer hybridisation and DNA strand synthesis using thermostable DNA polymerases allows exponential amplification of the sequences between the primers. RNA sequences can be amplified by first copying using reverse transcriptase to produce a complementary DNA (cDNA) copy. Amplified DNA fragments can be detected by a variety of means including gel electrophoresis, hybridisation with labelled probes, use of tagged primers that allow subsequent identification (eg by an enzyme linked assay), and use of fluorescently-tagged primers that give rise to a signal upon hybridisation with the target DNA (eg Beacon and TaqMan systems).

As well as PCR, a variety of other techniques have been developed for detection and amplification of specific nucleotide sequences. One example is the ligase chain reaction (1991, Barany, F. et al., Proc. Natl. Acad. Sci. USA 88, 189-193).

Another example is isothermal amplification which was first described in 1992 (Walker G T, Little M C, Nadeau J G and Shank D. Isothermal in vitro amplification of DNA by a restriction enzyme/DNA polymerase system. PNAS 89: 392-396 (1992) and termed Strand Displacement Amplification (SDA). Since then, a number of other isothermal amplification technologies have been described including Transcription Mediated Amplification (TMA) and Nucleic Acid Sequence Based Amplification (NASBA) that use an RNA polymerase to copy RNA sequences but not corresponding genomic DNA (Guatelli J C, Whitfield K M, Kwoh D Y, Barringer K J, Richmann D D and Gingeras T R. Isothermal, in vitro amplification of nucleic acids by a multienzyme reaction modeled after retroviral replication. PNAS 87: 1874-1878 (1990): Kievits T, van Gemen B, van Strijp D, Schukkink R, Dircks M, Adriaanse H, Malek L, Sooknanan R, Lens P. NASBA isothermal enzymatic in vitro nucleic acid amplification optimized for the diagnosis of HIV-1 infection. J Virol Methods. 1991 December; 35(3):273-86).

Other DNA-based isothermal techniques include Rolling Circle Amplification (RCA) in which a DNA polymerase extends a primer directed to a circular template (Fire A and Xu SQ. Rolling replication of short circles. PNAS 92: 4641-4645 (1995), Ramification Amplification (RAM) that uses a circular probe for target detection (Zhang W, Cohenford M, Lentrichia B, Isenberg H D, Simson E, Li H, Yi J, Zhang D Y. Detection of *Chlamydia trachomatis* by isothermal ramification amplification method: a feasibility study. J Clin Microbiol. 2002 January; 40(1):128-32.) and more recently, Helicase-Dependent isothermal DNA amplification (HDA), that uses a helicase enzyme to unwind the DNA strands instead of heat (Vincent M, Xu Y, Kong H. Helicase-dependent isothermal DNA amplification. EMBO Rep. 2004 August; 5(8):795-800.)

Recently, isothermal methods of DNA amplification have been described (Walker G T, Little M C, Nadeau J G and Shank D. Isothermal in vitro amplification of DNA by a restriction enzyme/DNA polymerase system. PNAS 89: 392-396 (1992). Traditional amplification techniques rely on continuing cycles of denaturation and renaturation of the target molecules at each cycle of the amplification reaction. Heat treatment of DNA results in a certain degree of shearing of DNA molecules, thus when DNA is limiting such as in the isolation of DNA from a small number of cells from a developing blastocyst, or particularly in cases when the DNA is already in a fragmented form, such as in tissue sections, paraffin blocks and ancient DNA samples, this heating-cooling cycle could further damage the DNA and result in loss of amplification signals. Isothermal methods do not rely on the continuing denaturation of the template DNA to produce single stranded molecules to serve as templates from further amplification, but on enzymatic nicking of DNA molecules by specific restriction endonucleases at a constant temperature.

The technique termed Strand Displacement Amplification (SDA) relies on the ability of certain restriction enzymes to nick the unmodified strand of hemi-modified DNA and the ability of a 5'-3' exonuclease-deficient polymerase to extend and displace the downstream strand. Exponential amplification is then achieved by coupling sense and antisense reactions in which strand displacement from the sense reaction serves as a template for the antisense reaction (Walker G T, Little M C, Nadeau J G and Shank D. Isothermal in vitro amplification of DNA by a restriction enzyme/DNA polymerase system. PNAS 89: 392-396 (1992). Such techniques have been used for the successful amplification of *Mycobacterium tuberculosis* (Walker G T, Little M C, Nadeau J G and Shank D. Isothermal in vitro amplification of DNA by a restriction enzyme/DNA polymerase system. PNAS 89: 392-396 (1992), HIV-1, Hepatitis C and HPV-16 Nuovo G. J., 2000), *Chlamydia trachomatis* (Spears P A, Linn P, Woodard D L and Walker G T. Simultaneous Strand Displacement Amplification and Fluorescence Polarization Detection of *Chlamydia trachomatis*. Anal. Biochem. 247: 130-137 (1997).

The use of SDA to date has depended on modified phosphorthioate nucleotides in order to produce a hemi-phosphorthioate DNA duplex that on the modified strand would be resistant to enzyme cleavage, resulting in enzymic nicking instead of digestion to drive the displacement reaction. Recently, however, several "nickase" enzyme have been engineered. These enzymes do not cut DNA in the traditional manner but produce a nick on one of the DNA strands. "Nickase" enzymes include N.Alw1 (Xu Y, Lunnen K D and Kong H. Engineering a nicking endonuclease N.Alw1 by domain swapping. PNAS 98: 12990-12995 (2001), N.BstNB1 (Morgan R D, Calvet C, Demeter M, Agra R, Kong H. Characterization of the specific DNA nicking activity of restriction endonuclease N.BstNBI. Biol. Chem. 2000 November; 381 (11):1123-5.) and MlyI (Besnier C E, Kong H. Converting MlyI endonuclease into a nicking enzyme by changing its oligomerization state. EMBO Rep. 2001 September; 2(9): 782-6. Epub 2001 Aug. 23). The use of such enzymes would thus simplify the SDA procedure.

In addition, SDA has been improved by the use of a combination of a heat stable restriction enzyme (Ava1) and Heat stable Exo-polymerase (Bst polymerase). This combination has been shown to increase amplification efficiency of the reaction from a $10^8$ fold amplification to $10^{10}$ fold amplification so that it is possible, using this technique, to the amplification of unique single copy molecules. The resultant amplification factor using the heat stable polymerase/enzyme combination is in the order of $10^9$ (Milla M. A., Spears P. A., Pearson R. E. and Walker G. T. Use of the Restriction Enzyme Ava1 and Exo-Bst Polymerase in Strand Displacement Amplification Biotechniques 1997 24:392-396).

To date, all isothermal DNA amplification techniques require the initial double stranded template DNA molecule to be denatured prior to the initiation of amplification. In addition, amplification is only initiated once from each priming event.

For direct detection, the target nucleic acid is most commonly separated on the basis of size by gel electrophoresis and transferred to a solid support prior to hybridisation with a probe complementary to the target sequence (Southern and Northern blotting). The probe may be a natural nucleic acid or analogue such as peptide nucleic acid (PNA) or locked nucleic acid (LNA) or intercalating nucleic acid (INA). The probe may be directly labelled (eg with $^{32}P$) or an indirect detection procedure may be used. Indirect procedures usually rely on incorporation into the probe of a "tag" such as biotin or digoxigenin and the probe is then detected by means such as enzyme-linked substrate conversion or chemiluminescence.

Another method for direct detection of nucleic acid that has been used widely is "sandwich" hybridisation. In this method, a capture probe is coupled to a solid support and the target nucleic acid, in solution, is hybridised with the bound probe. Unbound target nucleic acid is washed away and the bound nucleic acid is detected using a second probe that hybridises to the target sequences. Detection may use direct or indirect methods as outlined above. Examples of such methods include the "branched DNA" signal detection system, an example that uses the sandwich hybridization principle (1991, Urdea, M. S., et al., Nucleic Acids Symp. Ser. 24, 197-200). A rapidly growing area that uses nucleic acid hybridisation for direct detection of nucleic acid sequences is that of DNA microarrays, (2002, Nature Genetics, 32, [Supplement]; 2004, Cope, L. M., et al., Bioinformatics, 20, 323-331; 2004, Kendall, S. L., et al., Trends in Microbiology, 12, 537-544). In this process, individual nucleic acid species, that may range from short oligonucleotides, (typically 25-mers in the Affymetrix system), to longer oligonucleotides, (typically 60-mers in the Applied Biosystems and Agilent platforms), to even longer sequences such as cDNA clones, are fixed to a solid support in a grid pattern or photolithographically synthesized on a solid support. A tagged or labelled nucleic acid population is then hybridised with the array and the level of hybridisation to each spot in the array quantified. Most commonly, radioactively- or fluorescently-labelled nucleic acids (eg cRNAs or cDNAs) are used for hybridisation, though other detection systems can be employed, such as chemiluminescence.

A rapidly growing area that uses nucleic acid hybridisation for direct detection of nucleic acid sequences is that of DNA micro-arrays (Young R A Biomedical discovery with DNA arrays. Cell 102: 9-15 (2000); Watson A New tools. A new breed of high tech detectives. Science 289:850-854 (2000)). In this process, individual nucleic acid species, that may range from oligonucleotides to longer sequences such as complementary DNA (cDNA) clones, are fixed to a solid support in a grid pattern. A tagged or labelled nucleic acid population is then hybridised with the array and the level of hybridisation with each spot in the array quantified. Most commonly, radioactively- or fluorescently-labelled nucleic acids (eg cDNAs) were used for hybridisation, though other detection systems were employed.

Traditional methods for the detection of microorganisms such as bacteria, yeasts and fungi and include culture of the microorganisms on selective nutrient media then classification of the microorganism based on size, shape, spore production, characters such as biochemical or enzymatic reactions and specific staining properties (such as the Gram stain) as seen under conventional light microscopy. Viral species have to be grown in specialised tissue or cells then classified based on their structure and size determined by electron microscopy. A major drawback of such techniques is that not all microorganisms will grow under conventional culture or cell conditions limiting the usefulness of such approaches. With bacteria, for example, such as *Neisseria meningitidis*, *Streptococcus pneumoniae* and *Haemophilus influenzae* (which all cause meningitis and amongst which *N. meningitidis* causes both meningitis and fulminant meningococcaemia) all three species are difficult to culture. Blood culture bottles are routinely examined every day for up to seven days, and subculturing is required. *H. influenzae* requires special medium containing both nicotinamide adenine dinucleotide and haemin and growth on Chocolate Agar Plates. Blood cultures require trypticase soy broth or brain heart infusion and the addition of various additives such as sodium polyanetholesulphonate. For microorganisms such as *Clostridium botulinum*, which causes severe food poisoning and floppy baby syndrome, the identification of the toxin involves injection of food extracts or culture supernatants into mice and visualization of results after 2 days. In addition, culturing of the potential microorganism on special media takes a week. *Staphylococcus aureus* enterotoxin (a cause of food poisoning as well as skin infections, blood infections, pneumonia, osteomyelitis, arthritis and brain abscesses) is detected in minute amounts by selective absorption of the toxin via ion exchange resins or Reverse Passive Latex Agglutination using monoclonal antibodies. Its relative, *S. epidermis*, leads to blood infections and contaminates equipment and surfaces in hospitals and health care machines and appliances.

Non-viral microorganisms can also be classified based on their metabolic properties such as the production of specific amino acids or metabolites during fermentation reactions on substrates such as glucose, maltose or sucrose. Alternatively, microorganisms can be typed based on their sensitivity to antibiotics. Specific antibodies to cell surface antigens or excreted proteins such as toxins are also used to identify or type microorganisms. However, all the above methods rely on the culture of the microorganism prior to subsequent testing. Culture of microorganisms is expensive and time consuming and can also suffer from contamination or overgrowth by less fastidious microorganisms. The techniques are also relatively crude in that many tests must be done on the same sample in order to reach definitive diagnosis. Most microorganisms can not be readily grown in known media, and hence they fall below levels of detection when a typical mixed population of different species of microorganism is present in the wild or in association with higher organisms.

Other methods for the detection and identification of pathogenic microorganisms are based on the serological approach in which antibodies are produced in response to infection with the microorganism. Meningococci, for example, are classifiable on the basis of the structural differences in their capsular polysaccharides. These have different antigenicities, allowing five major serogroups to be determined, (A, B, C, Y and W-135). Enzyme Linked Immunosorbent Assays (ELISA) or Radio Immuno Assay (RIA) can assess the production of such antibodies. Both these methods detect the presence of specific antibodies produced by the host animal during the course of infection. These methods suffer the drawback in that it takes some time for an antibody to be produced by the host animal, thus very early infections are often missed. In addition, the use of such assays cannot reliably differentiate between past and active infection.

More recently, there has been much interest in the use of molecular methods for the diagnosis of infectious disease. These methods offer sensitive and specific detection of pathogenic microorganisms. Examples of such methods include the "branched DNA" signal detection system. This method is an example that uses the sandwich hybridization principle (Urdea M S et al. Branched DNA amplification multimers for the sensitive, direct detection of human HIV and hepatitis viruses. Nucleic Acids Symp Ser. 1991; (24):197-200).

Another method for the detection and classification of bacteria is the amplification of 16S ribosomal RNA sequences. 16S rRNA has been reported to be a suitable target for use in PCR amplification assays for the detection of bacterial species in a variety of clinical or environmental samples and has frequently been used to identify various specific microorganisms because 16S rRNA genes show species-specific polymorphisms (Cloud, J. L., H. Neal, R. Rosenberry, C. Y. Turenne, M. Jama, D. R. Hillyard, and K. C. Carroll. 2002. J. Clin. Microbiol. 40:400-406). However, pure culture of bacteria are required and after PCR amplification the sample still has to be sequenced or hybridized to a micro-array type device to determine the species (Fukushima M, Kakinuma K, Hayashi H, Nagai H, Ito K; Kawaguchi R. J Clin Microbiol. 2003 June; 41(6):2605-15). Such methods are expensive, time consuming and labour intensive.

The present inventors have developed new methods for detecting microorganisms which can be adapted to general detection or initial screening assays for any microbial species.

DISCLOSURE OF INVENTION

In a general aspect, the present invention relates to reducing the complexity of the base make up of a microbial genome or nucleic acid by treating microbial nucleic acid with an agent that modifies cytosine and amplifying the treated nucleic acid to produce a simplified form of the genome or nucleic acid.

In a first aspect, the present invention provides a method for simplification of a microbial genome or microbial nucleic acid comprising:

treating microbial genome or nucleic acid with an agent that modifies cytosine to form derivative microbial nucleic acid; and amplifying the derivative microbial nucleic acid to produce a simplified form of the microbial genome or nucleic acid.

In a second aspect, the present invention provides a method for producing a microbial-specific nucleic acid molecule comprising:

treating a sample containing microbial derived DNA with an agent that modifies cytosine to form derivative microbial nucleic acid; and amplifying at least part of the derivative microbial nucleic acid to form a simplified nucleic acid molecule having a reduced total number of cytosines compared with the corresponding untreated microbial nucleic acid, wherein the simplified nucleic acid molecule includes a nucleic acid sequence specific for a microorganism or microorganism type.

In a third aspect, the present invention provides a method for producing a microbial-specific nucleic acid molecule comprising:

obtaining a DNA sequence from a microorganism;

forming a simplified form of the microbial DNA sequence by carrying out a conversion of the microbial DNA sequence by changing each cytosine to thymine such that the simplified form of the microbial DNA comprises substantially bases adenine, guanine and thymine; and selecting a microbial-specific nucleic acid molecule from the simplified form of the microbial DNA.

In a fourth aspect, the present invention provides a microbial-specific nucleic acid molecule obtained by the method according to the third aspect of the present invention.

In a fifth aspect, the present invention provides use of the method according to the third aspect of the present invention to obtain probes or primers to bind or amplify the microbial-specific nucleic acid molecule in a test or assay.

In a sixth aspect, the present invention provides probes or primers obtained by the fifth aspect of the present invention.

In a seventh aspect, the present invention provides a method for detecting the presence of a microorganism in a sample comprising:

obtaining microbial DNA from a sample suspected of containing the microorganism;

treating the microbial nucleic acid with an agent that modifies cytosine to form derivative microbial nucleic acid;

providing primers capable of allowing amplification of a desired microbial-specific nucleic acid molecule to the derivative microbial nucleic acid;

carrying out an amplification reaction on the derivative microbial nucleic acid to form a simplified nucleic acid; and assaying for the presence of an amplified nucleic acid product containing the desired microbial-specific nucleic acid molecule, wherein detection of the desired microbial-specific nucleic acid molecule is indicative of the presence of the microorganism in the sample.

If the genome or microbial nucleic acid is DNA it can be treated to form a derivative DNA which is then amplified to form simplified form of DNA.

If the genome or microbial nucleic acid is RNA it can be converted to DNA prior to treating the microbial genome or nucleic acid. Alternatively, microbial RNA can be treated to yield a derivative RNA molecule which is then converted a derivative DNA molecule prior to amplification. Methods of conversion of RNA to DNA are well known and include use of reverse transcriptase to form a cDNA.

The microbial genome or nucleic acid can be obtained from phage, virus, viroid, bacterium, fungus, alga, protozoan, spirochaete, or single cell organism.

The microbial genome or nucleic acid can be selected from protein encoding nucleic acid, non-protein encoding nucleic acid, ribosomal gene regions of prokaryotes or single celled eukaryotic microorganisms. Preferably, the ribosomal gene regions are 16S or 23S in prokaryotes and 18S and 28S in the case of single celled eukaryotic microorganisms. The agent can be selected from bisulfite, acetate or citrate. Preferably, the agent is sodium bisulfite.

Preferably, the agent modifies an cytosine to a uracil in each strand of complementary double stranded microbial genomic DNA forming two derivative but non-complementary microbial nucleic acid molecules. In a preferred form, the cytosine is unmethylated as is typically found in microbial nucleic acid.

Preferably, the derivative microbial nucleic acid has a reduced total number of cytosines compared with the corresponding untreated microbial genome or nucleic acid.

Preferably, the simplified form of the microbial genome or nucleic acid has a reduced total number of cytosines compared with the corresponding untreated microbial genome or nucleic acid.

In one preferred form, the derivative microbial nucleic acid substantially contains bases adenine (A), guanine (G), thymine (T) and uracil (U) and has substantially the same total number of bases as the corresponding untreated microbial genome or nucleic acid.

In another preferred form, the simplified form of the microbial genome or nucleic acid is comprised substantially of bases adenine (A), guanine (G) and thymine (T).

Preferably, the amplification is carried out by any suitable means such as polymerase chain reaction (PCR), isothermal amplification, or signal amplification.

The method according to the second aspect of the present invention may further comprise:
detecting the microbial-specific nucleic acid molecule.
In a preferred form, the microbial-specific nucleic acid molecule is detected by:
providing a detector ligand capable of binding to a target region of the microbial-specific nucleic acid molecule and allowing sufficient time for the detector ligand to bind to the target region; and
measuring binding of the detector ligand to the target region to detect the presence of the microbial-specific nucleic acid molecule.

In another preferred form, the microbial-specific nucleic acid molecule is detected by separating an amplification product and visualising the separated product. Preferably, the amplification product is separated by electrophoresis and detected by visualising one or more bands on a gel.

Preferably, the microbial-specific nucleic acid molecule does not occur naturally in the microorganism.

In a preferred form, the microbial-specific nucleic acid molecule has a nucleic acid sequence indicative of a taxonomic level of the microorganism. The taxonomic level of the microorganism includes, but not limited to, family, genus, species, strain, type, or different populations from the same or different geographic or benthic populations.

In a preferred form of the method according to third aspect of the present invention, simplified forms of two or more microbial DNA sequences are obtained and the two or more sequences are compared to obtain at least one microbial-specific nucleic acid molecule.

In a preferred form of the seventh aspect of the present invention, the nucleic acid molecules are detected by:
providing a detector ligand capable of binding to a region of the nucleic acid molecule and allowing sufficient time for the detector ligand to bind to the region; and
measuring binding of the detector ligand to the nucleic acid molecule to detect the presence of the nucleic acid molecule.

In another preferred form, the nucleic acid molecules are detected by separating an amplification product and visualising the separated product.

In situations where the microorganism does not have a DNA genome or the microbial genome or nucleic acid is RNA, for example a RNA virus, the RNA viral genome can be first converted to cDNA in order to treat DNA with the agent. RNA may also be treated and the derivative RNA is converted to DNA prior to amplification.

Preferably, the derivative nucleic acid substantially contains the bases adenine (A), guanine (G), thymine (T) and uracil (U) and has substantially the same total number of bases as the corresponding unmodified microbial nucleic acid. Importantly, the derivative nucleic acid molecule substantially does not contain cytosine (C), with the proviso that the microbial DNA was not methylated at any cytosines.

Preferably the amplified derivative nucleic acid substantially contains the bases A, T and G and has substantially the same total number of bases as the corresponding derivative nucleic acid (and unmodified microbial nucleic acid). The amplified derivative nucleic acid is termed simplified nucleic acid.

In a preferred form, the microbial-specific nucleic acid molecule has a nucleic acid sequence indicative of a taxonomic level of the microorganism. The taxonomic level of the microorganism can include family, genus, species, strain, type, or different populations from the same or different geographic or benthic populations. In the case of bacteria we can adhere to the generally recognized schema, such as; Bacteria, Proteobacteria; Betaproteobacteria; Neisseriales; Neisseriaceae; *Neisseria*. Different populations may be polymorphic for single nucleotide changes or variation that exists in DNA molecules that exist in an intracellular form within a microorganism (plasmids or phagemids), or polymorphic chromosomal regions of microorganism genomes such as pathogenicity islands.

The present invention can also be used to recognize the fluidity of microbial and viral genomes, and can be used to recognize the chimeric nature of viral genomes, which can be in independent pieces, and hence newly arising strains arise from re-assortment of genomic regions from different animals e.g. new human influenza strains as chimeras of segments that are picked up from other mammalian or avian viral genomes.

It will be appreciated that the method can be carried out in silico from known nucleic acid sequences of microorganisms where one or more cytosines in the original sequences is converted to thymine to obtain the simplified nucleic acid. Sequence identity can be determined from the converted sequences. Such an in silico method mimics the treatment and amplification steps.

When a microbial-specific nucleic acid molecule has been obtained for any given microorganism by this method, probes or primers can be designed to ensure amplification of the region of interest in an amplification reaction. Thus, when the probes or primers have been designed, it will be possible to carry out clinical or scientific assays on samples to detect a given microorganisms at a given taxonomic level.

The microbial-specific nucleic acid molecule can be unique or have a high degree of similarity within a taxonomic level. One advantage of the present invention is the ability to greatly simplify the potential base differences between, or within, taxonomic levels, for example, of a microorganism to either an unique molecule or molecules that have close sequence similarity. Specific primers or reduced number of degenerate primers can be used to amplify the microbial-specific nucleic acid molecule in a given sample.

For double stranded DNA which contains cytosines, the treating step results in two derivative nucleic acids (one for each complementary strand), each containing the bases adenine, guanine, thymine and uracil. The two derivative nucleic acids are produced from the two single strands of the double stranded DNA. The two derivative nucleic acids preferably have no cytosines but still have the same total number of bases and sequence length as the original untreated DNA molecule. Importantly, the two derivative nucleic acids are not complimentary to each other and form a top and a bottom strand template for amplification. One or more of the strands can be used as the target for amplification to produce the simplified nucleic acid molecule. During amplification of the derivative nucleic acids, uracils in the top (or bottom strand) are replaced by thymines in the corresponding amplified simplified form of the nucleic acid. As amplification continues, the top (and/or bottom strand if amplified) will be diluted out as each new complimentary strand will have only bases adenine, guanine, thymine.

It will be appreciated that this aspect of the invention also includes nucleic acid molecules having complementary sequences to the microbial-specific nucleic acid molecule, and nucleic acid molecules that can hybridize, preferably under stringent conditions, to the microbial-specific nucleic acid molecule.

The present invention can use probes or primers that are indicative of representative types of microorganism which can be used to determine whether any microorganism is present in a given sample. Further microbial type-specific probes can be used to actually detect or identify a given, type, subtype, variant and genotype examples of microorganism.

When a microbial-specific nucleic acid molecule has been obtained or identified for any given microorganism, probes or primers can be designed to ensure amplification of the region of interest in an amplification reaction. It is important to note that both strands of a treated and thus converted genome, (hereafter termed "derivative nucleic acid') can be analyzed for primer design, since treatment or conversion leads to asymmetries of sequence, and hence different primer sequences are required for the detection of the 'top' and 'bottom' strands of the same locus, (also known as the 'Watson' and 'Crick' strands). Thus, there are two populations of molecules, the converted genome as it exists immediately after conversion, and the population of molecules that results after the derivative nucleic acid is replicated by conventional enzymological means (PCR) or by methods such as isothermal amplification. Primers are typically designed for the converted top strand for convenience but primers can also be generated for the bottom strand. Thus, it will be possible to carry out clinical or scientific assays on samples to detect a given microorganism.

The primers or probes can be designed to allow specific regions of derivative nucleic acid to be amplified. In a preferred form, the primers cause the amplification of the microbial-specific nucleic acid molecule.

In a seventh aspect, the present invention provides a kit for detecting a microbial-specific nucleic acid molecule comprising primers or probes according to fifth aspect of the present invention together with one or more reagents or components for an amplification reaction.

Preferably, the microorganism is selected from phage, virus, viroid, bacterium, fungus, alga, protozoan, spirochaete, single cell organism, or any other microorganism, no matter how variously classified, such as the Kingdom Protoctista by Margulis, L., et al 1990, Handbook of Protoctista, Jones and Bartlett, Publishers, Boston USA, or microorganisms that are associated with humans, as defined in Harrisons Principles of Internal Medicine, 12$^{th}$ Edition, edited by J D Wilson et al., McGraw Hill Inc, as well as later editions. It also includes all microorganisms described in association with human conditions defined in OMIM, Online Mendelian Inheritance in Man, www.ncbi.gov.

The microorganism can be a pathogen, naturally occurring environmental sample, water or airborne organism, (or an organism existing or being carried in a liquid or gaseous medium), in either a mature or spore form, either extracellularly or intracellularly, or associated with a chimeric life form, or existing ectocommensally between two or more life forms, such as a microbe associated with a lichen, or a microbe associated with a bacterial film.

It is possible to assay for the presence of RNA viruses or viroids by first converting their RNA genome into a cDNA form via reverse transcription and then modifying the cDNA by the reagent. This gets over the problem of any methylation existing at cytosines in RNA viruses, as the reverse transcriptase will copy these as if they were regular cytosines.

Preferably, the agent modifies unmethylated cytosine to uracil which is then replaced as a thymine during amplification of the derivative nucleic acid. Preferably, the agent used for modifying cytosine is sodium bisulfite. Other agents that similarly modify unmethylated cytosine, but not methylated cytosine can also be used in the method of the invention. Examples include, but not limited to bisulfite, acetate or citrate. Preferably, the agent is sodium bisulfite, a reagent, which in the presence of water, modifies cytosine into uracil.

Sodium bisulfite ($NaHSO_3$) reacts readily with the 5,6-double bond of cytosine to form a sulfonated cytosine reaction intermediate which is susceptible to deamination, and in the presence of water gives rise to a uracil sulfite. If necessary, the sulfite group can be removed under mild alkaline conditions, resulting in the formation of uracil. Thus, potentially all cytosines will be converted to uracils. Any methylated cytosines, however, cannot be converted by the modifying reagent due to protection by methylation.

The present invention can be adapted to assist in circumventing some of the emerging problems revealed by the enormous unexpected genomic variation between isolates of the same bacterial species, (2005, Tettelin, H., et al., Proc. Natl. Acad. Sci. USA. 102, 13950-13955; Genome analysis of multiple pathogenic isolates of *Streptococcus agalacticiae*: implications for the microbial "pan-genome"). All isolates of this bacterial species have a "core" genome of protein coding genes which represents approximately 80% of the gene pool, plus a dispensable genome consisting of partially shared and strain-specific protein coding genes. By treating the 23S gene(s) present within a bacterial population by the methods according to the present invention, the inventors can deal with a core non-protein coding component that is present in all bacterial isolates.

The present invention is suitable for clinical, environmental, forensic, biological warfare, or scientific assays for microorganisms where the initial identity above or at the species level is useful, in order to first determine the general group to which the organism belongs. Examples include, but not limited to, diagnosis of disease in any organism, (be it vertebrate, invertebrate, prokaryotic or eukaryotic, e.g. diseases of plants and livestock, diseases of human food sources such as fish farms and oyster farms), screening or sampling of environmental sources be they natural or contaminated, determining contamination of cell cultures or in vitro fertilized eggs for human blastocyst production in in vitro fertilization clinics or for animal breeding. Detection of microorganisms in forensic settings or in biological warfare contexts, is of particular significance.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia prior to development of the present invention.

In order that the present invention may be more clearly understood, preferred embodiments will be described with reference to the following drawings and examples.

BRIEF DESCRIPTION OF THE DRAWINGS

FIG. 1 shows alignment of part of the *Neisseria meningitidis* and *Neisseria gonorrhoeae* iga gene before and after genomic simplification. As can be seen, prior to genomic simplification, a total of 512 probe combinations would be required for the universal detection of *Neisseria* species (74% sequence similarity) compared with only 2 combinations after simplification to form derivative nucleic acid (97% sequence similarity). (SEQ ID NO is listed after each sequence).

FIG. 2 shows the use of INA probes to further increase the sequence similarity of the simplified sequences, since INA probes can be of shorter length than standard oligonucleotide probes. Combining the genomic simplification procedure with INA probes allows the selection and use of probes with 100% sequence similarity to the target sequence. (SEQ ID NO is listed after each sequence).

FIG. 3 shows genomic simplification to differentiate between closely related species using alignments of the iga gene from *Neisseria* and *Haemophilus*. As can be seen, the method of the present invention allows the simplification of the genomic material in order to produce species specific probes. In addition, although simplifying the genomic DNA, it still allows differentiation between *Neisseria* and the closely related *Haemophilus* species. (SEQ ID NO is listed after each sequence).

FIG. 4 shows alignment of the Streptococcal tuf gene before and after genomic simplification in 10 different species of Streptococci. Before treatment, a total of 12,288 probe combinations would be required for the universal primer of the tuf gene. After genomic simplification, only 64 probe combinations would be required for universal detection. In addition, the sequence similarity before simplification is only 67.5% which increases to 85% after simplification. (SEQ ID NO is listed after each sequence).

FIG. 5 shows alignment of the Staphylococcal enterotoxin genes before and after genomic simplification. Before bisulfite treatment, a total of 1,536 probe combinations would be required for the universal primer of the Staphylococcal enterotoxin gene. After genomic simplification only 64 probe combinations would be required for universal detection. (SEQ ID NO is listed after each sequence).

FIG. 6 shows alignment of the Influenza group A and B neuraminidase gene of various influenza strains before and after genomic simplification. Before treatment, a total of 2,048 probe combinations would be required for the universal primer of group A and B neuraminidase gene. After genomic simplification only 48 probe combinations would be required for universal detection. In addition, the sequence similarity before simplification is only 50% which increases to 75% after simplification. (SEQ ID NO is listed after each sequence).

FIG. 7 shows alignment of the Rotavirus VP4 gene before and after genomic simplification. Before treatment, a total of 512 probe combinations would be required for the universal primer of the Rotavirus VP4 gene. After genomic simplification only 32 probe combinations would be required for universal detection. (SEQ ID NO is listed after each sequence).

FIG. 8 shows the amplification products obtained by PCR from the genomically simplified 23S ribosomal gene regions of Gram positive and Gram negative bacteria, with appropriate amplicons being detected as bands of specific length by agarose gel electrophoresis. The arrow indicates the expected size of the amplicons relative to standard sized markers run in the Marker lane, (M). Using primers specific for Gram negative bacteria reveals bands only in the six Gram negative lanes, (top panel). Using primers specific for Gram positive bacteria reveals only bands in the six Gram positive lanes, (lower panel).

FIG. 9 shows the amplification products obtained by PCR from the genomically simplified 23S ribosomal gene regions of *E. coli* (lane 1) and *K. pneumoniae*, (lane 3). The specificity of amplification is illustrated by the absence of amplification products from the remaining 10 species of bacteria.

FIG. 10 shows the amplification product obtained by PCR from the genomically simplified 23S ribosomal gene regions using primers specific for *Neisseria*.

FIG. 11 shows the amplification product obtained by PCR from a protein coding gene from the genomically simplified region of the recA gene of *E. coli*. The specificity of the amplicon is illustrated by the presence of the *E. coli* recA amplicon and its absence from the other 11 species of bacteria.

FIG. 12 shows the amplification products obtained by PCR from the genomically simplified 23S ribosomal gene regions using primers specific for Staphylococci.

FIG. 13 shows the amplification products obtained by PCR from the genomically simplified 23S ribosomal gene regions using primers specific for Streptococci.

FIG. 14 shows the amplification products obtained by PCR from a protein coding gene from the genomically simplified region of the recA gene of *Staphylococcus epidermidis*. The two bands (arrowed) represent carry over amplicons from the first round, (upper band) and second round (lower band), PCR amplifications.

FIG. 15 shows detection of amplicons using specific primers targeting the genomically simplified 23S ribosomal genes of *Chlamydia trachomatis*.

FIG. 16 shows sequences of normal genomic and genomically simplified 23S rDNA sequences from *Staphylococcus epidermidis*. (SEQ ID NO is listed after each sequence).

FIG. 17 shows sequences of genomic and genomically simplified sequences of the *E. coli* recA gene. (SEQ ID NO is listed after each sequence).

MODE(S) FOR CARRYING OUT THE INVENTION

Definitions

The term "genomic simplification" as used herein means the genomic (or other) nucleic acid is modified from being comprised of four bases adenine (A), guanine (G), thymine (T) and cytosine (C) to substantially containing the bases adenine (A), guanine (G), thymine (T) but still having substantially the same total number of bases.

The term "derivative nucleic acid" as used herein means a nucleic acid that substantially contains the bases A, G, T and U (or some other non-A, G or T base or base-like entity) and has substantially the same total number of bases as the corresponding unmodified microbial nucleic acid. Substantially all cytosines in the microbial DNA will have been converted to uracil during treatment with the agent. It will be appreciated that altered cytosines, such as by methylation, may not necessarily be converted to uracil (or some other non-A, G or T base or base-like entity). As microbial nucleic acid typically does not contain methylated cytosine (or other cytosine alterations) the treated step preferably converts all cytosines. Preferably, cytosine is modified to uracil.

Figure 9:
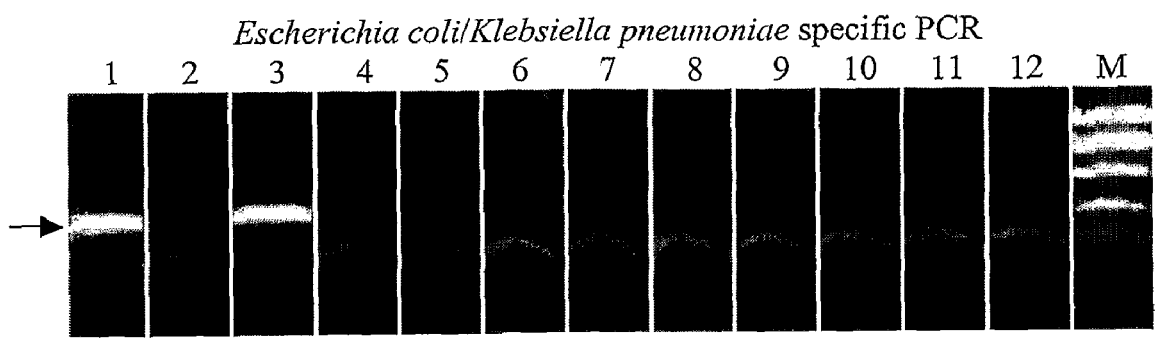

The term "simplified nucleic acid" as used herein means the resulting nucleic acid product obtained after amplifying derivative nucleic acid. Uracil in the derivative nucleic acid is then replaced as a thymine (T) during amplification of the derivative nucleic acid to form the simplified nucleic acid molecule. The resulting product has substantially the same number of total bases as the corresponding unmodified microbial nucleic acid but is substantially made up of a combination of three bases (A, G and T).

The term "simplified sequence" as used herein means the resulting nucleic acid sequence obtained after amplifying derivative nucleic acid to form a simplified nucleic acid. The resulting simplified sequence has substantially the same number of total bases as the corresponding unmodified microbial nucleic acid sequence but is substantially made up of a combination of three bases (A, G and T).

The term "non-converted sequence" as used herein means the nucleic acid sequence of the microbial nucleic acid prior to treatment and amplification. A non-converted sequence typically is the sequence of the naturally occurring microbial nucleic acid.

The term "modifies" as used herein means the conversion of an cytosine to another nucleotide. Preferably, the agent modifies unmethylated cytosine to uracil to form a derivative nucleic acid.

The term "agent that modifies cytosine" as used herein means an agent that is capable of converting cytosine to another chemical entity. Preferably, the agent modifies cytosine to uracil which is then replaced as a thymine during amplification of the derivative nucleic acid. Preferably, the agent used for modifying cytosine is sodium bisulfite. Other agents that similarly modify cytosine, but not methylated cytosine can also be used in the method of the invention. Examples include, but not limited to bisulfite, acetate or citrate. Preferably, the agent is sodium bisulfite, a reagent, which in the presence of acidic aqueous conditions, modifies cytosine into uracil. Sodium bisulfite ($NaHSO_3$) reacts readily with the 5,6-double bond of cytosine to form a sulfonated cytosine reaction intermediate which is susceptible to deamination, and in the presence of water gives rise to a uracil sulfite. If necessary, the sulfite group can be removed under mild alkaline conditions, resulting in the formation of uracil. Thus, potentially all cytosines will be converted to uracils. Any methylated cytosines, however, cannot be converted by the modifying reagent due to protection by methylation. It will be appreciated that cytosine (or any other base) could be modified by enzymatic means to achieve a derivative nucleic acid as taught by the present invention.

There are two broad generic methods by which bases in nucleic acids may be modified: chemical and enzymatic. Thus, modification for the present invention can also be carried out by naturally occurring enzymes, or by yet to be reported artificially constructed or selected enzymes. Chemical treatment, such as bisulphite methodologies, can convert cytosine to uracil via appropriate chemical steps. Similarly, cytosine deaminases, for example, may carry out a conversion to form a derivative nucleic acid. The first report on cytosine deaminases to our knowledge is 1932, Schmidt, G., Z. physiol. Chem., 208, 185; (see also 1950, Wang, T. P., Sable, H. Z., Lampen, J. O., J. Biol. Chem, 184, 17-28, Enzymatic deamination of cytosines nucleosides). In this early work, cytosine deaminase was not obtained free of other nucleodeaminases, however, Wang et al. were able to purify such an activity from yeast and E. coli. Thus any enzymatic conversion of cytosine to form a derivative nucleic acid which ultimately results in the insertion of a base during the next replication at that position, that is different to a cytosine, will yield a simplified genome. The chemical and enzymatic conversion to yield a derivative followed by a simplified genome are applicable to any nucleo-base, be it purines or pyrimidines in naturally occurring nucleic acids of microorganisms.

The term "simplified form of the genome or nucleic acid" as used herein means that a genome or nucleic acid, whether naturally occurring or synthetic, which usually contains the four common bases G, A, T and C, now consists largely of only three bases, G, A and T since most or all of the Cs in the genome have been converted to Ts by appropriate chemical modification and subsequent amplification procedures. The simplified form of the genome means that relative genomic complexity is reduced from a four base foundation towards a three base composition.

The term 'base-like entity' as used herein means an entity that is formed by modification of cytosine. A base-like entity can be recognised by a DNA polymerase during amplification of a derivative nucleic acid and the polymerase causes A, G or T to be placed on a newly formed complementary DNA strand at the position opposite the base-like entity in the derivate nucleic acid. Typically, the base-like entity is uracil that has been modified from cytosine in the corresponding untreated microbial nucleic acid. Examples of a base-like entity includes any nucleo-base, be it purine or pyrimidine.

The term "relative complexity reduction" as used herein relates to probe length, namely the increase in average probe length that is required to achieve the same specificity and level of hybridization of a probe to a specific locus, under a given set of molecular conditions in two genomes of the same size, where the first genome is "as is" and consists of the four bases, G, A T and C, whereas the second genome is of exactly the same length but some cytosines, (ideally all cytosines), have been converted to thymines. The locus under test is in the same location in the original unconverted as well as the converted genome. On average, an 11-mer probe will have a unique location to which it will hybridize perfectly in a regular genome of 4,194,304 bases consisting of the four bases G, A, T and C, ($4^{11}$ equals 4,194,304). However, once such a regular genome of 4,194,304 bases has been converted by bisulfite or other suitable means, this converted genome is now composed of only three bases and is clearly less complex. However the consequence of this decrease in genomic complexity is that our previously unique 11-mer probe no longer has a unique site to which it can hybridize within the simplified genome. There are now many other possible equivalent locations of 11 base sequences that have arisen de novo as a consequence of the bisulfite conversion. It will now require a 14-mer probe to find and hybridize to the original locus. Although it may initially appear counter intuitive, one thus requires an increased probe length to detect the original location in what is now a simplified three base genome, because more of the genome looks the same, (it has more similar sequences). Thus the reduced relative genomic complexity, (or simplicity of the three base genome), means that one has to design longer probes to find the original unique site.

The term "relative genomic complexity reduction" as used herein can be measured by increased probe lengths capable of being microbe-specific as compared with unmodified DNA. This term also incorporates the type of probe sequences that are used in determining the presence of a microorganism.

These probes may have non-conventional backbones, such as those of PNA or LNA or modified additions to a backbone such as those described in INA. Thus, a genome is considered to have reduced relative complexity, irrespective of whether the probe has additional components such as Intercalating pseudonucleotides, such as in INA. Examples include, but not limited to, DNA, RNA, locked nucleic acid (LNA), peptide nucleic acid (PNA), MNA, altritol nucleic acid (ANA), hexitol nucleic acid (HNA), intercalating nucleic acid (INA), cyclohexanyl nucleic acid (CNA) and mixtures thereof and hybrids thereof, as well as phosphorous atom modifications thereof, such as but not limited to phosphorothioates, methyl phospholates, phosphoramidites, phosphorodithiates, phosphoroselenoates, phosphotriesters and phosphoboranoates. Non-naturally occurring nucleotides include, but not limited to the nucleotides comprised within DNA, RNA, PNA, INA, HNA, MNA, ANA, LNA, CNA, CeNA, TNA, (2'-NH)-TNA, (3'-NH)-TNA, α-L-Ribo-LNA, α-L-Xylo-LNA, β-D-Xylo-LNA, α-D-Ribo-LNA, [3.2.1]-LNA, Bicyclo-DNA, 6-Amino-Bicyclo-DNA, 5-epi-Bicyclo-DNA, α-Bicyclo-DNA, Tricyclo-DNA, Bicyclo[4.3.0]-DNA, Bicyclo[3.2.1]-DNA, Bicyclo[4.3.0]amide-DNA, β-D-Ribopyranosyl-NA, α-L-Lyxopyranosyl-NA, 2'-R-RNA, α-L-RNA or α-D-RNA, β-D-RNA. In addition non-phosphorous containing compounds may be used for linking to nucleotides such as but not limited to methyliminomethyl, formacetate, thioformacetate and linking groups comprising amides. In particular nucleic acids and nucleic acid analogues may comprise one or more intercalator pseudonucleotides (IPN). The presence of IPN is not part of the complexity description for nucleic acid molecules, nor is the backbone part of that complexity, such as in PNA.

By 'INA' is meant an intercalating nucleic acid in accordance with the teaching of WO 03/051901, WO 03/052132, WO 03/052133 and WO 03/052134 (Unest A/S) incorporated herein by reference. An INA is an oligonucleotide or oligonucleotide analogue comprising one or more intercalator pseudonucleotide (IPN) molecules.

By 'HNA' is meant nucleic acids as for example described by Van Aetschot et al., 1995.

By 'MNA' is meant nucleic acids as described by Hossain et al, 1998.

'ANA' refers to nucleic acids described by Allert et al, 1999.

'LNA' may be any LNA molecule as described in WO 99/14226 (Exiqon), preferably, LNA is selected from the molecules depicted in the abstract of WO 99/14226. More preferably, LNA is a nucleic acid as described in Singh et al, 1998, Koshkin et al, 1998 or Obika et al., 1997.

'PNA' refers to peptide nucleic acids as for example described by Nielsen et al, 1991.

'Relative complexity reduction' as used herein, does not refer to the order in which bases occur, such as any mathematical complexity difference between a sequence that is ATATATATATATAT (SEQ ID NO: 1) versus one of the same length that is AAAAAAATTTTTTT (SEQ ID NO: 2), nor does it refer to the original re-association data of relative genome sizes, (and inferentially, genomic complexities), introduced into the scientific literature by Waring, M. & Britten R. J. 1966, Science, 154, 791-794; and Britten, R. J and Kohne D E., 1968, Science, 161, 529-540, and earlier references therein that stem from the Carnegie Institution of Washington Yearbook reports.

'Relative genomic complexity' as used herein refers to an unchanged position of bases in two genomes that is accessed by molecular probes (both the original and unconverted genomes have bases at invariant positions 1 to n. In the case of the 3 billion base pair haploid human genome of a particular human female, the invariant positions are defined as being from 1 to n, where n is 3,000,000,000. If in the sequence 1 to n, the $i^{th}$ base is a C in the original genome, then the $i^{th}$ base is a T in the converted genome.

The term "genomic nucleic acid" as used herein includes microbial (prokaryote and single celled eukaryote) RNA, DNA, protein encoding nucleic acid, non-protein encoding nucleic acid, and ribosomal gene regions of prokaryotes and single celled eukaryotic microorganisms.

The term "microbial genome" as used herein covers chromosomal as well as extrachromosomal nucleic acids, as well as temporary residents of that genome, such a plasmids, bacteriphage and mobile elements in the broadest sense. The "genome" has a core component as exemplified by *S. galactiae*, as well as possibly having coding and non-coding elements that vary between different isolates.

The term "microbial derived DNA" as used herein includes DNA obtained directly from a microorganism or obtained indirectly by converting microbial RNA to DNA by any of the known or suitable method such as reverse transcriptase.

The term "microorganism" as used herein includes phage, virus, viroid, bacterium, fungus, alga, protozoan, spirochaete, single cell organism, or any other microorganism, no matter how variously classified, such as the Kingdom Protoctista by Margulis, L., et al 1990, Handbook of Protoctista, Jones and Bartlett, Publishers, Boston USA, or microorganisms that are associated with humans, as defined in Harrisons Principles of Internal Medicine, $12^{th}$ Edition, edited by J D Wilson et al., McGraw Hill Inc, as well as later editions. It also includes all microorganisms described in association with human conditions defined in OMIM, Online Mendelian Inheritance in Man, www.ncbi.gov.

The term "microbial-specific nucleic acid molecule" as used herein means a molecule which has been determined or obtained using the method according to the present invention which has one or more sequences specific to a microorganism.

The term "taxonomic level of the microorganism" as used herein includes family, genus, species, strain, type, or different populations from the same or different geographic or benthic populations. While in the case of bacteria the generally recognized schema, such as; Bacteria, Proteobacteria; Betaproteobacteria; Neisseriales; Neisseriaceae; *Neisseria* is used. Different populations may be polymorphic for single nucleotide changes or variation that exists in DNA molecules that exist in an intracellular form within a microorganism (plasmids or phagemids), or polymorphic chromosomal regions of microorganism genomes such as pathogenicity islands. The fluidity of microbial and viral genomes is recognized, and includes the chimeric nature of viral genomes, which can be in independent nucleic acid pieces. Hence, newly arising strains from re-assortment of genomic regions from different animals e.g., new human influenza strains as chimeras of segments that are picked up from other mammalian or avian viral genomes.

The term "close sequence similarity" as used herein includes the above definition of relative sequence complexity and probe lengths as a measure.

Materials and Methods

Extraction of DNA

In general, microbial DNA (or viral RNA) can be obtained from any suitable source. Examples include, but not limited to, cell cultures, broth cultures, environmental samples, clinical samples, bodily fluids, liquid samples, solid samples such as tissue. Microbial DNA from samples can be obtained by standard procedures. An example of a suitable extraction is as follows. The sample of interest is placed in 400 µl of 7 M Guanidinium hydrochloride, 5 mM EDTA, 100 mM Tris/HCl pH6.4, 1% Triton-X-100, 50 mM Proteinase K (Sigma), 100 µg/ml yeast tRNA. The sample is thoroughly homogenised with disposable 1.5 ml pestle and left for 48 hours at 60° C. After incubation the sample is subjected to five freeze/thaw cycles of dry ice for 5 minutes/95° C. for 5 minutes. The sample is then vortexed and spun in a microfuge for 2 minutes to pellet the cell debris. The supernatant is removed into a clean tube, diluted to reduce the salt concentration then phenol:chloroform extracted, ethanol precipitated and resuspended in 50 µl of 10 mM Tris/0.1 mM EDTA.

Specifically, the DNA extractions from Gram positive and Gram negative bacteria grown on standard agar plates (with nutritional requirements specific to each species) were performed as follows.

For DNA extraction from Gram Negative bacteria the protocol was as follows:
a) Using a sterile toothpick bacterial colonies were scraped off the culture plate into a sterile 1.5 ml centrifuge tube.
b) 180 µl of Guanidinium thiocyanate extraction buffer (7M Guanidinium thiocyanate, 5 mM EDTA (pH8.0), 40 mM Tris/Hcl pH 7.6, 1% Triton-X-100) was added and the sample mixed to resuspend the bacterial colonies.
c) 20 µl (20 mg/ml) Proteinase K was added and the samples were mixed well.
d) Samples were incubated @ 55° C. for 3 hours to lyse the cells.
e) 200 µl of water was added to each sample and samples mixed by gentle pipetting.
f) 400 µl of Phenol/Chloroform/iso-amyl alcohol (25:24:1) was added and the samples vortexed for 2×15 seconds.
g) The samples were then spun in a microfuge at 14,000 rpm for 4 minutes.
h) The aqueous phase was removed into a clean 1.5 ml centrifuge tube.
i) 400 µl of Phenol/Chloroform/iso-amyl alcohol (25:24:1) was added and the samples vortexed for 2×15 seconds.
j) The samples were then spun in a microfuge at 14,000 rpm for 4 minutes.
k) The aqueous phase was removed into a clean 1.5 ml centrifuge tube.
l) 800 µl of 100% ethanol was added to each sample, the sample vortexed briefly then left at −20° c. for 1 hour.
m) The samples were spun in a microfuge at 14,000 rpm for 4 minutes at 4° C.
n) The DNA pellets were washed with 500 µl of 70% ethanol.
o) The samples were spun in a microfuge at 14,000 rpm for 5 minutes at 4° C., the ethanol was discarded and the pellets were air dried for 5 minutes.
p) Finally the DNA was resuspended in 100 µl of 10 mM Tris/HCl pH 8.0, 1 mM EDTA pH 8.0.
q) The DNA concentration and purity were calculated by measuring the absorbance of the solution at 230, 260, 280 nm.

For DNA extraction from Gram Positive bacteria the protocol was as follows:
a) Using a sterile toothpick bacterial colonies were scraped off the culture plate into a sterile 1.5 ml centrifuge tube.
b) 180 µl of 20 mg/ml Lysozyme (Sigma) and 200 µg of Lysostaphin (Sigma) was added to each sample and the samples were mixed gently to resuspend the bacterial colonies.
c) The samples were incubated at 37° C. for 30 minutes to degrade the cell wall.
d) The samples were then processed and the DNA extracted according to the QIAamp DNA mini kit protocol for Gram positive bacteria.

DNA extraction from Cytology samples from patients.
a) The sample was shaken vigorously by hand to resuspend any sedimented cells and to ensure the homogeneity of the solution.
b) 4 ml of the resuspended cells were transferred to a 15 ml Costar centrifuge tube.
c) The tubes were centrifuged in a swing-out bucket rotor at 3000×g for 15 minutes.
d) The supernatant was carefully decanted and discarded without disturbing the pelleted cellular material.
e) The pelleted cells were resuspended in 200 µl of lysis buffer (100 mM Tris/HCl pH 8.0, 2 mM EDTA pH 8.0, 0.5% SDS, 0.5% Triton-X-100) and mixed well until the solution was homogeneous.
f) 80 µl of the sample was transferred to a 96 well sample preparation plate
g) 20 µl of Proteinase K was added and the solution incubated at 55° C. for 1 hour (this procedure results in cell lysis)

DNA Extraction from Urine Samples

DNA was extracted from a starting volume of 1 ml of urine according to the QIAamp UltraSens™ Virus Handbook.

Bisulfite Treatment of DNA Samples

Bisulfite treatment was carried out according the MethylEasy™ High Throughput DNA bisulfite modification kit (Human Genetic Signatures, Australia) see also below.

Surprisingly, it has been found by the present inventors that there is no need to separate the microbial DNA from other sources of nucleic acids, for example when there is microbial DNA in a sample of human cells. The treatment step can be used for an vast mixture of different DNA types and yet a microbial-specific nucleic acid can be still identified by the present invention. It is estimated that the limits of detection in a complex DNA mixtures are that of the limits of standard PCR detection which can be down to a single copy of a target nucleic acid molecule.

Samples

Any suitable sample can be used for the present invention. Examples include, but not limited to, microbial cultures, clinical samples, veterinary samples, biological fluids, tissue culture samples, environmental samples, water samples, effluent. As the present invention is adaptable for detecting any microorganism, this list should not be considered as exhaustive.

Kits

The present invention can be implemented in the form of various kits, or combination of kits and instantiated in terms of manual, semi automated or fully robotic platforms. In a preferred form, the MethyEasy™ or HighThroughput MethylEasy™ kits (Human Genetic Signatures Pty Ltd, Australia) allow conversion of nucleic acids in 96 or 384 plates using a robotic platform such as EpMotion.

Bisulfite Treatment

An exemplary protocol for effective bisulfite treatment of nucleic acid is set out below. The protocol results in retaining substantially all DNA treated. This method is also referred to herein as the Human Genetic Signatures (HGS) method. It will be appreciated that the volumes or amounts of sample or reagents can be varied.

Preferred method for bisulfite treatment can be found in U.S. Ser. No. 10/428,310 or PCT/AU2004/000549 incorporated herein by reference.

To 2 µg of DNA, which can be pre-digested with suitable restriction enzymes if so desired, 2 µl (1/10 volume) of 3 M NaOH (6 g in 50 ml water, freshly made) was added in a final volume of 20 µl. This step denatures the double stranded DNA molecules into a single stranded form, since the bisulfite reagent preferably reacts with single stranded molecules. The mixture was incubated at 37° C. for 15 minutes. Incubation at temperatures above room temperature can be used to improve the efficiency of denaturation.

After the incubation, 208 µl 2 M Sodium Metabisulfite (7.6 g in 20 ml water with 416 ml 10 N NaOH; BDH AnalaR #10356.4D; freshly made) and 12 µl of 10 mM Quinol (0.055 g in 50 ml water, BDH AnalR #103122E; freshly made) were added in succession. Quinol is a reducing agent and helps to reduce oxidation of the reagents. Other reducing agents can also be used, for example, dithiothreitol (DTT), mercaptoethanol, quinone (hydroquinone), or other suitable reducing agents. The sample was overlaid with 200 µl of mineral oil. The overlaying of mineral oil prevents evaporation and oxidation of the reagents but is not essential. The sample was then incubated overnight at 55° C. Alternatively the samples can be cycled in a thermal cycler as follows: incubate for about 4 hours or overnight as follows: Step 1, 55° C./2 hr cycled in PCR machine; Step 2, 95° C./2 min. Step 1 can be performed at any temperature from about 37° C. to about 90° C. and can vary in length from 5 minutes to 8 hours. Step 2 can be performed at any temperature from about 70° C. to about 99° C. and can vary in length from about 1 second to 60 minutes, or longer.

After the treatment with Sodium Metabisulfite, the oil was removed, and 1 µl tRNA (20 mg/ml) or 2 µl glycogen were added if the DNA concentration was low. These additives are optional and can be used to improve the yield of DNA obtained by co-precipitating with the target DNA especially when the DNA is present at low concentrations. The use of additives as carrier for more efficient precipitation of nucleic acids is generally desired when the amount nucleic acid is <0.5 µg.

An isopropanol cleanup treatment was performed as follows: 800 µl of water were added to the sample, mixed and then 1 ml isopropanol was added. The water or buffer reduces the concentration of the bisulfite salt in the reaction vessel to a level at which the salt will not precipitate along with the target nucleic acid of interest. The dilution is generally about 1/4 to 1/1000 so long as the salt concentration is diluted below a desired range, as disclosed herein.

The sample was mixed again and left at 4° C. for a minimum of 5 minutes. The sample was spun in a microfuge for 10-15 minutes and the pellet was washed 2× with 70% ETOH, vortexing each time. This washing treatment removes any residual salts that precipitated with the nucleic acids.

The pellet was allowed to dry and then resuspended in a suitable volume of T/E (10 mM Tris/0.1 mM EDTA) pH 7.0-12.5 such as 50 µl. Buffer at pH 10.5 has been found to be particularly effective. The sample was incubated at 37° C. to 95° C. for 1 min to 96 hr, as needed to suspend the nucleic acids.

Another example of bisulfite treatment can be found in WO 2005021778 (incorporated herein by reference) which provides methods and materials for conversion of cytosine to uracil. In some embodiments, a nucleic acid, such as gDNA, is reacted with bisulfite and a polyamine catalyst, such as a triamine or tetra-amine. Optionally, the bisulfite comprises magnesium bisulfite. In other embodiments, a nucleic acid is reacted with magnesium bisulfite, optionally in the presence of a polyamine catalyst and/or a quaternary amine catalyst. Also provided are kits that can be used to carry out methods of the invention. It will be appreciated that these methods would also be suitable for the present invention in the treating step.

Amplification

PCR amplifications were performed in 25 µl reaction mixtures containing 2 µl of bisulfite-treated genomic DNA, using the Promega PCR master mix, 6 ng/µl of each of the primers. Strand-specific nested primers are used for amplification. $1^{st}$ round PCR amplifications were carried out using PCR primers 1 and 4 (see below). Following $1^{st}$ round amplification, 1 µl of the amplified material was transferred to $2^{nd}$ round PCR premixes containing PCR primers 2 and 3 and amplified as previously described. Samples of PCR products were amplified in a ThermoHybaid PX2 thermal cycler under the conditions: 1 cycle of 95° C. for 4 minutes, followed by 30 cycles of 95° C. for 1 minute, 50° C. for 2 minutes and 72° C. for 2 minutes; 1 cycle of 72° C. for 10 minutes.

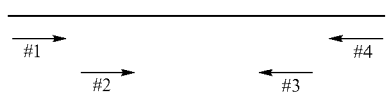

Multiplex Amplification

If multiplex amplification is required for detection, the following methodology can be carried out.

One µl of bisulfite treated DNA is added to the following components in a 25 µl reaction volume, x1 Qiagen multiplex master mix, 5-100 ng of each $1^{st}$ round INA or oligonucleotide primer 1.5-4.0 mM $MgSO_4$, 400 uM of each dNTP and 0.5-2 unit of the polymerase mixture. The components are then cycled in a hot lid thermal cycler as follows. Typically there can be up to 200 individual primer sequences in each amplification reaction

| Step 1 | 94° C. | 15 minute | 1 cycle |
|---|---|---|---|
| Step 2 | 94° C. | 1 minute | |
| | 50° C. | 3 minutes | 35 cycles |
| | 68° C. | 3 minutes | |
| Step 3 | 68° C. | 10 minutes | 1 cycle |

A second round amplification is then performed on a 1 µl aliquot of the first round amplification that is transferred to a second round reaction tube containing the enzyme reaction mix and appropriate second round primers. Cycling is then performed as above.

Primers

Any suitable PCR primers can be used for the present invention. A primer typically has a complementary sequence to a sequence which will be amplified. Primers are typically oligonucleotides but can be oligonucleotide analogues.

Probes

The probe may be any suitable nucleic acid molecule or nucleic acid analogue. Examples include, but not limited to, DNA, RNA, locked nucleic acid (LNA), peptide nucleic acid (PNA), MNA, altritol nucleic acid (ANA), hexitol nucleic acid (HNA), intercalating nucleic acid (INA), cyclohexanyl nucleic acid (CNA) and mixtures thereof and hybrids thereof, as well as phosphorous atom modifications thereof, such as but not limited to phosphorothioates, methyl phospholates, phosphoramidites, phosphorodithiates, phosphoroselenoates, phosphotriesters and phosphoboranoates. Non-naturally occurring nucleotides include, but not limited to the nucleotides comprised within DNA, RNA, PNA, INA, HNA, MNA, ANA, LNA, CNA, CeNA, TNA, (2'-NH)-TNA, (3'-NH)-TNA, α-L-Ribo-LNA, α-L-Xylo-LNA, β-D-Xylo-LNA, α-D-Ribo-LNA, [3.2.1]-LNA, Bicyclo-DNA, 6-Amino-Bicyclo-DNA, 5-epi-Bicyclo-DNA, α-Bicyclo-DNA, Tricyclo-DNA, Bicyclo[4.3.0]-DNA, Bicyclo[3.2.1]-DNA, Bicyclo[4.3.0]amide-DNA, β-D-Ribopyranosyl-NA, α-L-Lyxopyranosyl-NA, 2'-R-RNA, α-L-RNA or α-D-RNA, β-D-RNA. In addition non-phosphorous containing compounds may be used for linking to nucleotides such as but not limited to methyliminomethyl, formacetate, thioformacetate and linking groups comprising amides. In particular nucleic acids and nucleic acid analogues may comprise one or more intercalator pseudonucleotides.

Preferably, the probes are DNA or DNA oligonucleotides containing one or more internal IPNs forming INA.

Electrophoresis

Electrophoresis of samples was performed according to the E-gel system user guide (www.invitrogen.doc).

Detection Methods

Numerous possible detection systems exist to determine the status of the desired sample. It will be appreciated that any known system or method for detecting nucleic acid molecules could be used for the present invention. Detection systems include, but not limited to:

I. Hybridization of appropriately labelled DNA to a microarray type device which could select for 10→200,000 individual components. The arrays could be composed of either INAs, PNAs or nucleotide or modified nucleotides arrays onto any suitable solid surface such as glass, plastic, mica, nylon, bead, magnetic bead, fluorescent bead or membrane;

II. Southern blot type detection systems;

III. Standard PCR detection systems such as agarose gel, fluorescent read outs such as Genescan analysis. Sandwich hybridisation assays, DNA staining reagents such as ethidium bromide, Syber green, antibody detection, ELISA plate reader type devices, fluorimeter devices;

IV. Real-Time PCR quantitation of specific or multiple genomic amplified fragments or any variation on that.

V. Any of the detection systems outlined in the WO 2004/065625 such as fluorescent beads, enzyme conjugates, radioactive beads and the like;

VI. Any other detection system utilizing an amplification step such as ligase chain reaction or Isothermal DNA amplification technologies such as Strand Displacement Amplification (SDA).

VII. Multi-photon detection systems.

VIII. Electrophoresis and visualisation in gels.

IX. Any detection platform used or could be used to detect nucleic acid.

Intercalating Nucleic Acids

Intercalating nucleic acids (INA) are non-naturally occurring polynucleotides which can hybridize to nucleic acids (DNA and RNA) with sequence specificity. INA are candidates as alternatives/substitutes to nucleic acid probes in probe-based hybridization assays because they exhibit several desirable properties. INA are polymers which hybridize to nucleic acids to form hybrids which are more thermodynamically stable than a corresponding naturally occurring nucleic acid/nucleic acid complex. They are not substrates for the enzymes which are known to degrade peptides or nucleic acids. Therefore, INA should be more stable in biological samples, as well as, have a longer shelf-life than naturally occurring nucleic acid fragments. Unlike nucleic acid hybridization which is very dependent on ionic strength, the hybridization of an INA with a nucleic acid is fairly independent of ionic strength and is favoured at low ionic strength under conditions which strongly disfavour the hybridization of naturally occurring nucleic acid to nucleic acid. The binding strength of INA is dependent on the number of intercalating groups engineered into the molecule as well as the usual interactions from hydrogen bonding between bases stacked in a specific fashion in a double stranded structure. Sequence discrimination is more efficient for INA recognizing DNA than for DNA recognizing DNA.

Preferably, the INA is the phosphoramidite of (S)-1-O-(4,4'-dimethoxytriphenylmethyl)-3-O-(1-pyrenylmethyl)-glycerol.

INA are synthesized by adaptation of standard oligonucleotide synthesis procedures in a format which is commercially available. Full definition of INA and their synthesis can be found in WO 03/051901, WO 03/052132, WO 03/052133 and WO 03/052134 (Unest A/S) incorporated herein by reference.

There are indeed many differences between INA probes and standard nucleic acid probes. These differences can be conveniently broken down into biological, structural, and physico-chemical differences. As discussed above and below, these biological, structural, and physico-chemical differences may lead to unpredictable results when attempting to use INA probes in applications were nucleic acids have typically been employed. This non-equivalency of differing compositions is often observed in the chemical arts.

With regard to biological differences, nucleic acids are biological materials that play a central role in the life of living species as agents of genetic transmission and expression. Their in vivo properties are fairly well understood. INA, however, is a recently developed totally artificial molecule, conceived in the minds of chemists and made using synthetic organic chemistry. It has no known biological function.

Structurally, INA also differs dramatically from nucleic acids. Although both can employ common nucleobases (A, C, G, T, and U), the composition of these molecules is structurally diverse. The backbones of RNA, DNA and INA are composed of repeating phosphodiester ribose and 2-deoxyribose units. INA differ from DNA or RNA in having one or more large flat molecules attached via a linker molecule(s) to the polymer. The flat molecules intercalate between bases in the complementary DNA stand opposite the INA in a double stranded structure.

The physico/chemical differences between INA and DNA or RNA are also substantial. INA binds to complementary DNA more rapidly than nucleic acid probes bind to the same target sequence. Unlike DNA or RNA fragments, INA bind poorly to RNA unless the intercalating groups are located in terminal positions. Because of the strong interactions between the intercalating groups and bases on the complementary DNA strand, the stability of the INA/DNA complex is higher than that of an analogous DNA/DNA or RNA/DNA complex.

Unlike other nucleic acids such as DNA or RNA fragments or PNA, INA do not exhibit self aggregation or binding properties.

As INA hybridize to nucleic acids with sequence specificity, INA are useful candidates for developing probe-based assays and are particularly adapted for kits and screening assays. INA probes, however, are not the equivalent of nucleic acid probes. Consequently, any method, kits or compositions which could improve the specificity, sensitivity and reliability of probe-based assays would be useful in the detection, analysis and quantitation of DNA containing samples. INA have the necessary properties for this purpose.

Results

The detection of microorganisms (such as bacterial, viral or fungal strains) is often hampered by the large number of individual strains of microorganism within that species.

The general in silico principles of the invention are taught using the bacteria Neisseria meningitidis, Neisseria gonorrhoeae, Haemophilus influenzae, Streptococcus sp and Staphylococcus (FIGS. 1 to 5). The general principles of the invention have been taught using the Influenza virus and Rotavirus (FIGS. 6 and 7).

The general biochemical data for teaching and supporting the invention is described in FIGS. 8 to 18 using clinically relevant Gram positive as well as Gram negative bacteria.

Bacteria

FIG. 1 shows a 34 nucleotide region of the iga protease gene in N. meningitides and the corresponding locus in N. gonorrhoeae (as these regions exist in their natural bacterial genomes) (full classification; Bacteria; Proteobacteria; Betaproteobacteria; Neisseriales; Neisseriaceae; Neisseria meningitides, Z2491 Serogroup A and full locus characteristics; iga, IgA1 protease; GeneID 906889. Locus Tag NMA0905; RefSeq accession #NC_003116.1; PMID 10761919; Parkhill J et al., 2000, Nature, 404, 502-506). There is 74% sequence similarity between these two Neisseria 34 nucleotide sequences. PCR-based primers made to amplify these regions in both bacterial species would require degenerate primers with 512 possible combinations. The common sequence used for part of the PCR amplification would be the 34 nucleotide sequence GYAATYW AGGYCGYCTY GAAGAYTAYA AYATGGC (SEQ ID NO: 3) where the standard code for designating different positions is given below; N=A, G, T or C; D=A, G or T; H=A, T or C; B=G, T or C; V=G, A or C; K=G or T; S=C or G; Y=T or C; R=A or G; M=A or C and W=A or T.

However, when the bacterial DNA from these two species is treated with the bisulfite reagent, (resulting in the conversion of cytosines to thymines), the naturally occurring sequences are converted to derivative sequences that have no coding potential and do not exist in nature. The derivative sequences are now 97% sequence similar. PCR-based primers designed to allow PCR amplification of both these bacterial loci in a single test now only require only 2 primer combinations. The combination would be based on the sequence GTAATTW AGGTTGTTTT GAAGATTATA ATATGGT (SEQ ID NO: 4), where only the base at position 7 is either an adenine or a thymine (denoted W). Thus, the bisulfite conversion reduces the relative genomic complexity from 512 to 2 primer types. This massive reduction simplifies the amplification of the same locus from related bacterial species.

Further advantages accrue from optionally using INA probes to amplify regions from these two bacterial species, again using the same locus. FIG. 2 illustrates the same 34 nucleotide region of the iga genes of N. meningitides and N. gonorrhoeae as depicted in FIG. 1, with the added demonstration of the extent to which probe length and complexity can be reduced even further using INA probes. A short INA 16 mer sequence AGGYCGYCTY GAAGAY (SEQ ID NO: 5) would require 16 possible primer combinations to detect this region, but after conversion with bisulfite, a unique primer sequence, AGGTTGTTTT GAAGAT (SEQ ID NO: 6) would be sufficient. The advantage of the INA molecule is that; owing to the intercalating pseudonucleotides that are incorporated into its backbone, hybridization to the correct locus is much more easily distinguished from non specific binding, owing to the increased Tm of the INA relative to a standard oligonucleotide. It will be appreciated, however, that standard oligonucleotides will still perform adequately.

When closely related bacterial species cause similar clinical symptoms, bisulfite converted DNA can again be used to design simpler probes to assay for presence of specific bacterial types. FIG. 3 shows the DNA alignments of the iga gene in three bacterial species, one of which, Haemophilus influenzae is from a different taxonomic group. Bisulfite treatment of the bacterial DNA resulted in a much smaller number of probe combinations. This comparison illustrates the importance of being able to assay for unrelated species in one test. Both N. meningitides and H. influenzae cause meningitis, so it is advantageous to be able to assay in the one test for all microbes that cause the same clinical symptoms.

The analysis of a large number of different bacterial species from the same taxonomic group is again facilitated by the present invention. FIG. 4 shows a 40 nucleotide segment of the tuf gene in 10 bacterial species of the Streptococcus group namely S. oralis, S. mitis, S. dysgalactiae, S. cristatus, S. gordonii, S. parauberis, S. pneumoniae, S. bovis, S. vestivularis and S. uberis. This region has approximately 68% sequence similarity between the 10 species and requires 12,288 primer combinations in order to simultaneously assay for the 10 species in the one test. The bisulfite converted sequence between these species has 85% sequence similarity and now only requires 64 possible primer combinations.

The analysis of different strains belonging to the same bacterial species is also simplified by the invention. FIG. 5 illustrates a 23 nucleotide segment of the Staphylococcal aureus enterotoxin gene se. The natural sequence of this gene region has only 56% sequence similarity between all 7 strains and requires 1536 primer combinations, whereas the bisulfite converted sequence has 74% sequence similarity and requires only 64 primer combinations.

Viral Nucleic Acid Analyses and Relative Genomic Complexity Reduction

The principle of relative genomic complexity reduction can also be applied to viral groups, such as Influenza virus which has a DNA genome, as well as to viral groups which have RNA genomes, (as the RNA can be converted to DNA by reverse transcriptase and then bisulfite treated accordingly). To illustrate application for viral detection, the neuraminidase gene of strains of influenza virus, (Family Orthomyxoviridae), and the surface protein encoding VP4 gene of rotavirus strains, (Family Reoviridae), both viruses having a segmented RNA genome, have been used. The taxonomy of influenza viruses is complex, with types A, B and C for example being based on antigenic characteristics, and with further subtypes being based on site of origin, year of isolation, isolate number and subtype. This reinforces the need in the first instance to be able to identify influenza viruses as a group, and only then to drill down to analyse sub-sub-classification levels.

The taxonomy of rotaviruses is also complex. The number of rotavirus serotypes is large with two main serotypes being recognized, the P and G serotypes. There are minimally 14 different G serotypes and their unambiguous detection is of importance in paediatric medicine. It is estimated that by the age of three, nearly every child worldwide has already been infected at least once by Rotavirus, even though these infections may be subclinical and have only mild effects on the gastrointestinal tract.

The consequences of infection by influenza at the clinical level are well known, with significant morbidity and mortality nearly every winter. However there can be massive secondary complications following infection, especially by Streptococcus pneumoniae, Hemophilus influenzae and Staphylococcus aureus. It is very clearly advantageous to be able to simultaneously analyse for both viral infections and bacterial infections since pneumonial complications can arise from mixed features of bacterial and viral infections, and prompt antibiotic treatment can be an effective therapy.

The relative genomic complexity reduction in 9 different influenza strains is shown in FIG. 6. A 20 nucleotide region of the neuraminidase gene of influenza virus is shown in its DNA form. There is 50% sequence similarity between these 9 isolates. After bisulfite conversion, the sequence similarity has increased to 75%. In its original form it would require 2048 possible primer combinations to analyse these 9 strains, whereas after bisulfite conversion only 48 primer combinations are needed.

The relative genomic complexity reduction in the VP4 gene of 3 different rotavirus strains is shown in FIG. 7. A 20 nucleotide region of the VP4 gene has 52% sequence similarity before conversion and 74% after conversion. The number of primer combinations reduces from 512 to 32.

The molecular data supporting the in silico approach of simplifying microbial genomes as a means of detecting microorganisms is illustrated in FIGS. 8 through 15 using clinically relevant microbial species that are commonly encountered in hospital and pathology testing units.

It is a distinct advantage, and a clinical imperative for the rapid detection of contaminating microorganisms, if the initial decision could be made between the presence of Gram positive or Gram negative bacteria in a sample. The method described herein provides such a test using the 23S ribosomal genes of different bacterial species to generate a set of primers that allow either Gram positive or Gram negative bacteria to be detected by utilising such primers on simplified genomes via an amplification reaction. The 23S sequences are ideal for such high level distinctions, since they occur in all bacterial species, unlike some protein coding sequences which are optional additions to some bacterial genomes, such as seen in the previous *S. galactiae* example. Many protein coding microbial sequences are akin to genomic “flotsam and jetsam”, and their usefulness lies in differentiating between lower level taxonomic categories such as different microbial strains, types or isolates, or in the case of viruses, between different types or newly arisen mutations. The normal and simplified genomic sequences of both of these components, the non protein coding ribosomal RNA genes, and the protein coding recA gene of bacteria are given in FIGS. 15 and 16 respectively. The primer sequences used to perform the amplification reactions for the 23S bacterial amplicons are given in Table 1. The primer sequences used to perform the amplification reactions for the recA amplicons are given in Table 2. All primers are made to bisulfite treated DNA and are shown in the 5' to 3' orientation.

Table 1 sets out suitable bacterial primers sequences used in amplifying bisulfite simplified DNA from the 23S ribosomal RNA gene(s) using alignments to generate primers for the detection of Gram positive (Pos), Gram negative (Neg). In addition primers were designed for specific detection of *Mycoplasma* spp (Myc), *Staphylococcus* spp (Staph), *Streptococcus* spp (Strep), *Neisseria* spp (NG), *Chlamydia* (CT), and *Escherichia coli* and *Klebsiella pneumoniae* (EC).

The following symbols designate the following base-additions; N=A, G, T or C; D=A, G or T; H=A, T or C; B=G, T or C; V=G, A or C; K=G or T; S=C or G; Y=T or C; R=A or G; M=A or C and W=A or T.

All primers used were based on bisulfite simplified DNA sequences.

TABLE 1

Bacterial primers

| 23S Primers | Sequence 5'-3' | SEQ ID NO |
|---|---|---|
| Pos-R1F1 | GGTTTTTTTTGAAATAGTTTTAGGGTTA | 7 |
| Neg-R1F1 | GGTTTTTTTTGAAARTTATTTAGGTAGT | 8 |
| Pos-R1F2 | TGGKAGTTAGAWTGTGRRWGATAAG | 9 |
| Neg-R1F2 | TGGGAGATAKATRGTGGGTGTTAAT | 10 |
| Pos-R1F3 | GGATGTGGDRTTKTKWAGATAA | 11 |
| Neg-R1F3 | TGAWGTGGGAAGGTWTAGATAG | 12 |
| Pos-R1R1 | HCAATMHHACTTCAMMMCMMYT | 13 |
| Neg-R1R1 | WCAAHHCACCTTCAHMAACYTAC | 14 |
| Pos-R1R2 | ACCAACATTCTCACTYMTAAWMAMTCCAC | 15 |
| Neg-R1R2 | ATCAACATTCACACTTCTAATACCTCCAA | 16 |
| W-Pos-R1F1 | GGTTTTTTTYGAAATAGTTTTAGGGTTA | 17 |
| W-Neg-R1F1 | GGTTTTTTTYGAAARTTATTTAGGTAGT | 18 |
| W-Pos-R1F2 | YGGKAGTTAGAWYGYGRRWGATAAG | 19 |
| W-Neg-R1F2 | YGGGAGATAKAYRGYGGGTGTTAAT | 20 |
| W-Pos-R1F3 | GGATGTGGDRTTKYKWAGATAA | 21 |
| W-Neg-R1F3 | YGAWGTGGGAAGGTWTAGATAG | 22 |
| W-Pos-R1R1 | HCRATMHHRCTTCRMMMCMMYT | 23 |
| W-Neg-R1R1 | WCRAHHCACCTTCAHMRACYTAC | 24 |
| W-Pos-R1R2 | ACCRACATTCTCACTYMTAAWMAMTCCAC | 25 |
| W-Neg-R1R2 | ATCAACATTCRCACTTCTAATACCTCCAA | 26 |
| Pos-R2F1 | KTTRAGAAAAGTWTTTAGDDAGRK | 27 |
| Neg-R2F1 | TTTARGAAAAGTTWTTAAGTWTTA | 28 |
| Pos-R2F2 | AGDTRAGRWGAGDATTTTWAGGTKR | 29 |
| Neg-R2F2 | GGKTRGGWWGAGAATWTTAAGGTGT | 30 |
| Pos-R2R1 | AATYTMYMATTAAAACAATACMCAA | 31 |
| Neg-R2R1 | AATCTCAAAWAAAAACAAYMYMACC | 32 |
| Pos-R2R2 | ACMHACATCTTCACWMAYAYTAYAAYTTCACC | 33 |
| Neg-R2R2 | MAYTACATCTTCACAACMAHWTCAAYTTCACT | 34 |
| Pos-R2R3 | CMATAYYAAAYTACAATAAAACTC | 35 |
| Neg-R2R3 | CAATAYMAAACTAYAATAAAAATT | 36 |
| Pos-R3F1 | GGTGAARTTRTARTRTKWGTGAAGATGTDKG | 37 |
| Neg-R3F1 | AGTGAARTTGAWDTKGTTGTGAAGATGTART | 38 |
| Pos-R3F2 | GATWGGATGGAAAGATTTTRTRGAG | 39 |
| Neg-R3F2 | KGTWAGATGGAAAGATTTTGTGAAT | 40 |
| Pos-R3R1 | HYMAYMMWAYHAAAATAATATCC | 41 |
| Neg-R3R1 | TCAAMMMYWMMAAAATAATATTT | 42 |
| Pos-R3R2 | AWCCATTCTAAAAAAACCTTTAAACA | 43 |

TABLE 1-continued

Bacterial primers

| 23S Primers | Sequence 5'-3' | SEQ ID NO |
|---|---|---|
| Neg-R3R2 | AACCAWWMYWAAMHMACCTTCAWACT | 44 |
| EC-F1 | GTTGGTAAGGTGATATGAATTGTTATAA | 45 |
| EC-F2 | TTATTATTAATTGAATTTATAGGTTA | 46 |
| EC-F3 | GAGGAGTTTAGAGTTTGAATTAGTRTG | 47 |
| EC_R1 | TATATACAAAACTATCACCCTATATC | 48 |
| EC-R2 | TCATCAAACTCACAACAYATAC | 49 |
| NG-F1 | TTGAGTAAGATATTGATGGGGTAA | 50 |
| NG-F2 | TATGGTTAGGGGGTTATTGTA | 51 |
| NG-R1 | AATCTATCATTTAAAACCTTAACC | 52 |
| NG-R2 | CCTAACTATCTATACCTTCCCACT | 53 |
| NG-R3 | CACTCCCCTACCATACCAATAAACC | 54 |
| CT-R1F1 | GTATGATGAGTTAGGGAGTTAAGTTAAA | 55 |
| CT-R1F2 | GGTGAGGTTAAGGGATATATA | 56 |
| CT-R1F3 | AAAAGAGTGAAGAGTTGTTTGGTTTAGATA | 57 |
| CT-R1R1 | TCCAAACCTTTTTCAACATTAACT | 58 |
| CT-R1R2 | CCCTAAAATTATTTCAAAAAAACAAAA | 59 |
| CT-R2F1 | TTAGTGGGGGTTTATTGGTTTATTAATGGA | 60 |
| CT-R2F2 | TAAGGAAGTGATGATTTGAAGATAGTTGGA | 61 |
| CT-R2R1 | ACACCTTCTCTACTAAATACT | 62 |
| CT-R2R2 | TATACCATAAATCTTCACTAATATC | 63 |
| CT-R3F1 | TTGTGTAGATGATGGAGTAGTAGGTTA | 64 |
| CT-R3F2 | GAATGATGGAGTAAGTTAAGTATGTGGA | 65 |
| CT-R3R1 | TAAAAATTATTCTTAAAAACCTCACT | 66 |
| CT-R3R2 | AAATTATCTCACACACCTTAAAATAT | 67 |
| CT-R4F1 | AATGTTAAAAGGTTAAAGGGATAT | 68 |
| CT-R4F2 | TATTGAATTTAAGTTTTGGTGAATGGTT | 69 |
| CT-R4R1 | CCAATATTTCAACATTAACTCCCACTCTC | 70 |
| CT-R4R2 | ATATCCATCTTCCAAATTCATAAAATAAT | 71 |
| CT-R4R3 | TAAACAACAACAATTCCACTTTCC | 72 |
| Myc-R1F1 | ATAGGAAAAGAAAWTGAAWGWGATTTTG | 73 |
| Myc-R1F2 | GTGTAGTGGTGAGTGAAAGTGGAATAGG | 74 |
| Myc-R1R1 | TAAACAAMTTCMMTCAAAATAACATTTYYCAA | 75 |
| Myc-R1R2 | CTAATTAATATTTAAACTTACCC | 76 |
| Myc-R2F1 | TTTTGAAATTATATGTTTATAATGT | 77 |
| Myc-R2F2 | AAGTATGAGTTGGTGAGTTATGATAGT | 78 |
| Myc-R2R1 | CCTCCAMTTAWTYATAATCTYAC | 79 |

TABLE 1-continued

Bacterial primers

| 23S Primers | Sequence 5'-3' | SEQ ID NO |
|---|---|---|
| Myc-R2R2 | CACCWAAAYAACACCATCATACATT | 80 |
| Myc-R3F1 | TGTAGTTAGATAGTGGGGTATAAGTTTTA | 81 |
| Myc-R3F2 | AGGGGAAGAGTTTAGATTATTAAA | 82 |
| Myc-R3R1 | ATAACTTCAWCYCMWATACAACACTCAT | 83 |
| Myc-R3R2 | ATCAATTTAAAAAATTCTCACTCYCAAA | 84 |
| Myc-R4F1 | TTTTTATWATTGGATTTGGGGWTAAA | 85 |
| Myc-R4F2 | TKKTWWTTAGTATTGAGAATGA | 86 |
| Myc-R4F3 | TGTAAATTWATTTTGTAAGTTWGT | 87 |
| Myc-R4F4 | GAATGAGGGGGGATTGTTTAATT | 88 |
| Myc-R4R1 | TCTATAACCAAAACAATCAAAAAATA | 89 |
| Myc-R4R2 | CATTACACCTAACAAATATCTTCACC | 90 |
| Myc-R5F1 | ATWWATAGGTTGAATAGGTRAGAAAT | 91 |
| Myc-R5F2 | ATAGTGATTTGGTGGTTTAGTATGGAAT | 92 |
| Myc-R5R1 | CAAACCTACTTCAACTCAAAAATAAATAAAT | 93 |
| Myc-R5R2 | ACAACAATTTAAACCCAACTCACATATCT | 94 |
| Myc-R5R3 | AAAAYAAMWCTYTTCAATCTTCCTAYAAA | 95 |
| Strep-R1F1 | ATWWTGTTAAGGDWRTGARRAGGAAG | 96 |
| Strep-R1F2 | TAGRAGGGTAAATTGARGWGTTTA | 97 |
| Strep-R1F3 | TKATTTGGGAARRTWRGTTAAAGAGA | 98 |
| Strep-R1R1 | TCTCTTCAACTTAACCTCACATCAT | 99 |
| Strep-R1R2 | ATAATTTCAAATCTACAWCMWAAT | 100 |
| Strep-R2F1 | RATKTATTGGAGGATTGAATTAGGG | 101 |
| Strep-R2F2 | ATGTTGAAAAGTGTTTGGATGAT | 102 |
| Strep-R2R1 | TCTAAAATYAATAAWCCAAAATAAMCCCCTC | 103 |
| Strep-R2R2 | ACTACCAAYHATAWHTCATTAAC | 104 |
| Strep-R3F1 | AGGTTGAKATTTTTGTATTAGAGTA | 105 |
| Strep-R3F2 | RWAGTGATGGAGGGATGTAGTAGGTTAAT | 106 |
| Strep-R3R1 | CTTTTCTYAACAATATAACATCACT | 107 |
| Strep-R3R2 | CTCTCAMTCACCTAAAACTACTCA | 108 |
| Staph-R1F1 | AGAAGTTGATGAAGGATGTTATTAATGA | 109 |
| Staph-R1F2 | GTTATTGATATGTGAATWTATAGTATRTT | 110 |
| Staph-R1R1 | CAAAAYTHTTACCTTCTYTAATYC | 111 |
| Staph-R1R2 | CAACAAAATTYCACATACTCCAT | 112 |
| Staph-R2F1 | GATTTGATGTAAGGTTAAGTAGT | 113 |
| Staph-R2F2 | TTGGTTAGGTTGAAGTTTAGGTAATATTGAA | 114 |
| Staph-R2F3 | GATTTATGTTGAAAAGTGAGTGGATGAATTGA | 115 |
| Staph-R2R1 | CCTYTTTCTAACTCCCAAATTAAATTAAT | 116 |

TABLE 1-continued

Bacterial primers

| 23S Primers | Sequence 5'-3' | SEQ ID NO |
|---|---|---|
| Staph-R3F1 | GAAGTTGTGGATTGTTTTTGGATA | 117 |
| Staph-R3F2 | AAGGGTGTTGAAGTATGATTGTAAGGATAT | 118 |
| Staph-R3R1 | TACAMTCCAAYMACACACTTCACCTATCCTA | 119 |
| Staph-R3R2 | CAACAATATAAAATCAACAACTCAAA | 120 |
| Staph-R4F1 | AGGAGTGGTTAGTTTTTGTGAAGTTA | 121 |
| Staph-R4F1 | ACAAATTAAAAAWCCAACACAACT | 122 |
| Staph-R4F2 | TAACACTATCTCCCACCAYAATMAAT | 123 |

Table 2 sets out bacterial primer sequences used in amplifying simplified DNA from the recA protein coding gene using alignments from *Staphylococcus aureus* (SA), *Staphylococcus epidermidis* (SE), *Serratia marscesens* (SM), *Escherichia coli* (EC) and *Yersinia enterocolitica* (YE) for unique bacterial typing.

TABLE 2

Bacterial primer sequences used in amplifying simplified DNA from the recA protein coding gene

| RecA Specific | Sequence | SEQ ID NO |
|---|---|---|
| A-SA-F1 | TAGGTTGTTGAGTTTTAATTATA | 124 |
| A-SA-F2 | GAAGTATAAAGTAATGGTGGGGTG | 125 |
| A-SA-R1 | TACAATATCAACTACACCACTTCTAACAAAT | 126 |
| A-SA-R2 | TAATAAAAATAACAATTATATTT | 127 |
| A-SE-F1 | AAGGTTGTAGAGTATTAAGTATTTTAAG | 128 |
| A-SE-F2 | GTTGATAATGTATTAGGGGTTGGA | 129 |
| A-SE-F3 | ATATGGATTTGAAAGTTTAGGTAAGATG | 130 |
| A-SE-R1 | TACTACTAAATCAACAACAACAATATCCACA | 131 |
| A-SE-R2 | CTTAATACTTAAAACATTAATCT | 132 |
| A-SM-F1 | GAGAATAAGTAAAAGGTGTTAGTTGTG | 133 |
| A-SM-F2 | GATTTTTATTGGTTTATTGTTATTTGATATTGTT | 134 |
| A-SM-R1 | CAAATAATCAATATCAACACCCAACTTTTTC | 135 |
| A-SM-R2 | TACACACCACCAAACCCATATAC | 136 |
| A-EC-F1 | GAAAATAAATAGAAAGTGTTGGTG | 137 |
| A-EC-F2 | TGTTTTTATTGGATATTGTGTTT | 138 |
| A-EC-R1 | CAATAACATCTACTACACCAAAACAC | 139 |
| A-EC-R2 | CATATTAAACTACTTCAAATTAGCC | 140 |
| A-YE-F1 | TATGTGTTTTGGTGAAGATTGTTTA | 141 |
| A-YE-F2 | TTTTGATATTGTATTGGGGGTG | 142 |

TABLE 2-continued

Bacterial primer sequences used in amplifying simplified DNA from the recA protein coding gene

| RecA Specific | Sequence | SEQ ID NO |
|---|---|---|
| A-YE-F3 | GGTTTGTTAATGGGGTGTATTGTTGAG | 143 |
| A-YE-R1 | CATACTCTACATCAATAAAA | 144 |

Table 1 shows the bacterial primer sequences used in amplifying bisulfite simplified DNA from the 23S ribosomal RNA gene(s) using multiple alignments to generate optimal primers for the detection of Gram positive (denoted Pos), and Gram negative (denoted Neg), bacteria. In addition primers were also designed for specific detection of groups of species as well as for individual species. The designations for these bacterial primer groups are as follows; *Escherichia coli* and *Klebsiella pneumoniae* (EC), *Neisseria* spp (NG), *Chlamydia* (CT), *Mycoplasma* spp (Myc), *Streptococcus* spp (Strep) and *Staphylococcus* spp (Staph). The F and R sub designations refer to forward and reverse primers respectively. In addition, where more than one possible base is necessary at a given nucleotide position, the base degeneracy is given by the following code; N=A, G, T or C; D=A, G or T; H=A, T or C; B=G, T or C; V=G, A or C; K=G or T; S=C or G; Y=T or C; R=A or G; M=A or C; and W=A or T. To reiterate, all primers used in this invention are based on bisulfite simplified DNA sequences.

Table 2 shows bacterial primers sequences used in amplifying bisulfite simplified DNA from the recA protein coding gene using alignments from *Staphylococcus aureus* (SA), *Staphylococcus epidermidis* (SE), *Serratia marscesens* (SM). *Escherichia coli* (EC) and *Yersinia enterocolitica* (YE) for unique bacterial typing.

FIG. 8 shows the amplification products obtained by PCR from the genomically simplified 23S ribosomal gene regions of Gram positive and Gram negative bacteria, with appropriately sized amplicons being detected as bands of specific length by agarose gel electrophoresis. The arrow indicates the expected size of the amplicons relative to standard sized markers run in the Marker lane, (M). Using primers specific for Gram negative bacteria reveals bands only in the six Gram negative lanes 1 through 6, (top panel), for *Escherichia coli, Neisseria gonorrheae, Klebsiella pneumoniae, Moraxella catarrhalis, Pseudomonas aeruginosa* and *Proteus vulgaris*. Using primers specific for Gram positive bacteria reveals only bands in the six Gram positive lanes, 7 through 12 (lower panel) for *Enterococcus faecalis, Staphylococcus epidermidis, Staphylococcus aureus, Staphylococcus xylosis, Streptococcus pneumoniae* and *Streptococcus haemolyticus*.

FIG. 9 shows the amplification products obtained by PCR from the genomically simplified 23S ribosomal gene regions designed to detect amplicons from only two Gram negative bacterial species, (in this example) *E. coli* and *K. pneumoniae*. The specificity of the amplification methodology is illustrated by the presence of amplicons in lanes 1 and 3, representing *E. coli* and *K. pneumoniae*, and the absence of amplification products in lane 2, as well as from lanes 4 through 12, these 10 empty lanes representing the remaining 10 species of bacteria used in the test.

Figure 10:
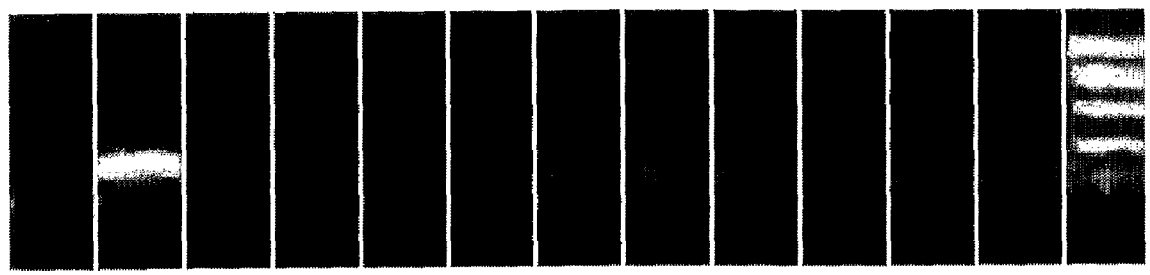

FIG. 10 shows the amplification products obtained by PCR from the genomically simplified 23S ribosomal gene regions using primers specific for only one bacterial group, *Neisseria*.

The specificity of the genomic simplification methodology is illustrated by the presence of an amplicon only in lane 2, representing *Neisseria gonorrheae*, and the absence of an amplification product in lane 1, as well as from lanes 3 through 12, these 11 empty lanes representing the remaining 11 species of bacteria used in the test.

For analysis of individual microbial species, protein coding genes can also be used where appropriate, with the proviso that different strains of microorganism are not polymorphic for their presence/absence of the gene sequence in question.

Figure 11:
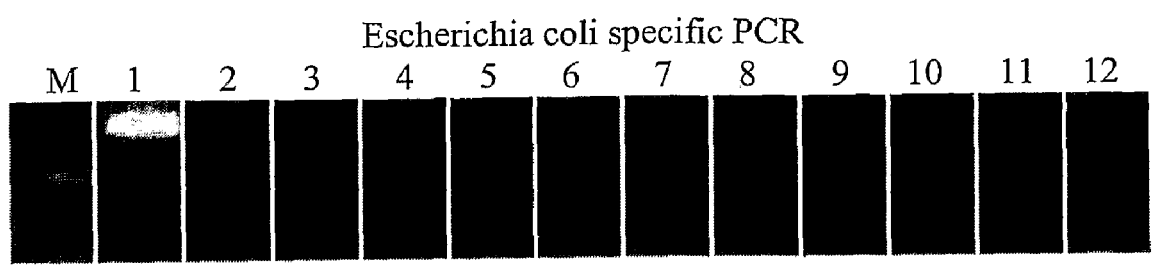

FIG. 11 illustrates the use of primers to the bacterial recA gene of *E. coli*. The specificity of the amplicon is illustrated by the presence of the correctly sized amplicon in lane 1 and its absence from the remaining lanes 2 through 12, representing other 11 species of bacteria.

Figure 12:
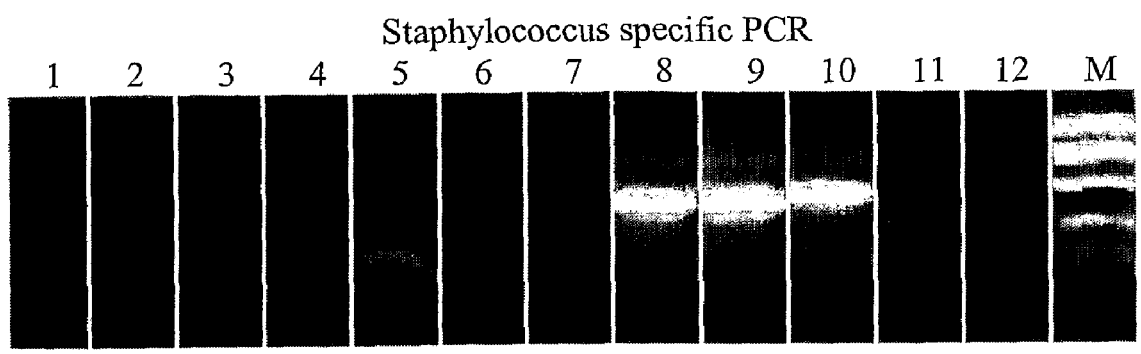

The data of FIG. 12 further illustrate the specificity of primers that reveal the membership of a larger bacterial group, such as Staphylococci. The amplification products obtained by PCR from the genomically simplified 23S ribosomal gene regions using primers specific for Staphylococci reveal amplicons only in lanes 8, 9, and 10, representing *Staphylococcus epidermidis, Staphylococcus aureus* and *Staphylococcus* xylosis. The absence of an amplification product in lanes 1 through 7, as well as from lanes 11 and 12, attest to the specificity of the reaction. The 9 empty lanes representing the 9 species of non Staphylococcal bacteria used in the test.

Figure 13:
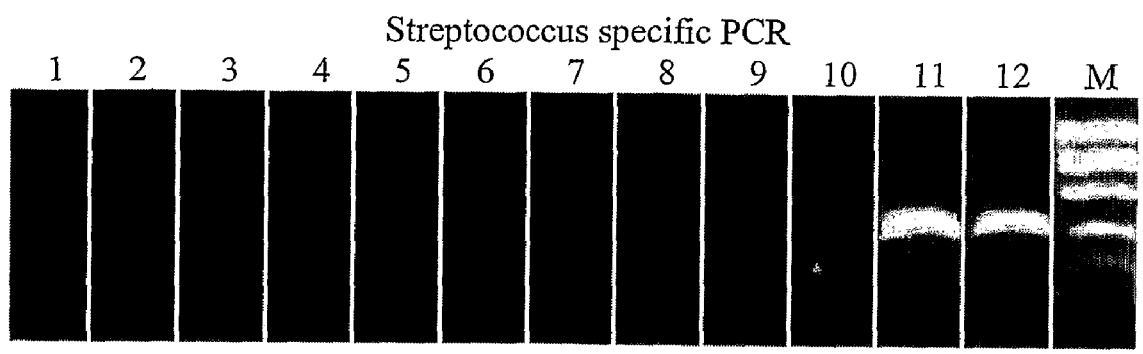

FIG. 13 shows the amplification products obtained by PCR from the genomically simplified 23S ribosomal gene regions using primers specific for Streptococcal bacteria. The amplification products obtained by PCR from the genomically simplified 23S ribosomal gene regions using primers specific for Streptoococci reveal amplicons only in lanes 11 and 12, representing *Streptococcus pneumoniae* and *Streptococcus haemolyticus*. The absence of an amplification product in lanes 1 through 10, reveal the specificity of the reaction. These 10 empty lanes representing the 10 species of non Streptococcal bacteria used in the test.

Figure 14:
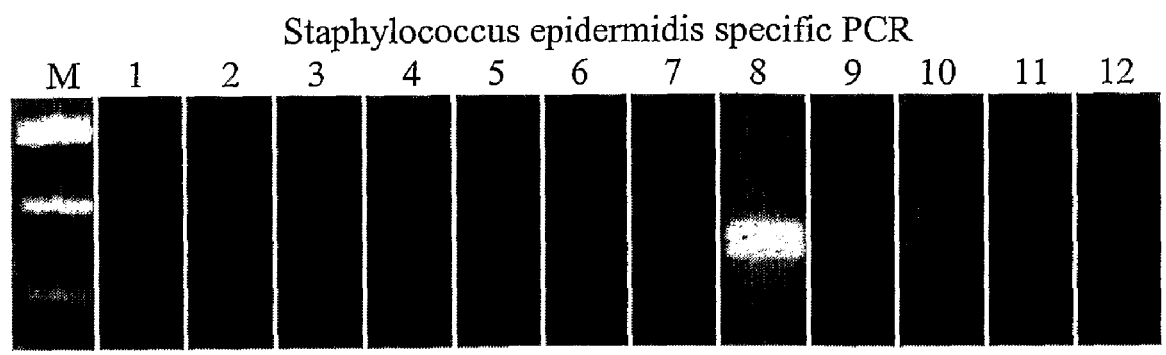

FIG. 14 shows the amplification products obtained by PCR from a protein coding gene from the genomically simplified region of the recA gene of *Staphylococcus epidermidis*, (lane 8). The two bands (arrowed) represent the carry over amplicons from the first round, (upper band) and second round (lower band), PCR amplifications. The absence of amplicons in lanes 1 through 7, and 9 through 12 show the specificity of the method and emphasizes the point that protein coding genes can be utilized in particular circumstances instead of the non coding components of the genome, to achieve detection of only one bacterial species.

Figure 15:
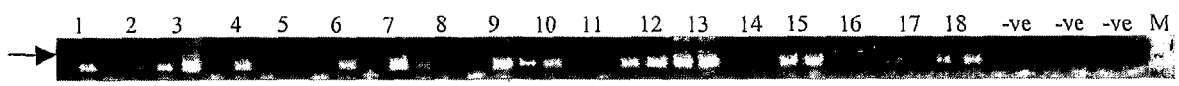

FIG. 15 shows detection of amplicons using specific primers targeting the genomically simplified 23S ribosomal genes of *Chlamydia* PCR reactions were carried out in duplicate due to the low amounts of starting DNA. Lane number 5 was DNA extracted from the urine of a known negative individual. The presence of a band in any of the duplicates was considered a positive reaction for the presence of *Chlamydia* DNA.

FIG. 16 shows the normal nucleotide sequence of the 23S ribosomal RNA gene from *E. coli* and the same sequence after genomic simplification, where for illustrative purposes all cytosines have been replaced with thymines.

FIG. 17 shows the normal nucleotide sequence of the recA gene from *E. coli* and the same sequence after genomic simplification, where for illustrative purposes all cytosines have been replaced with thymines.

In summary, the bisulfite-treated DNA from microbial sources, when amplified using genomically simplified primers, be they oligonucleotides or modified nucleic acids such as INAs provide an unsurpassed detection system for finding microorganisms of any type within a sample, be that sample from human clinical material or at another extreme from an environmental source such as contaminated water. The present invention has been demonstrated for a wide range of different bacterial species, and for a clinically relevant virus. The detection of single celled eukaryotic microorganisms such as the yeast *Saccharomyces cerevisiae* or its relatives is a simple extension of the method. It requires similar genomic sequence sources, such as the 18 or 28S ribosomal sequences, or as shown, protein coding sequences that are specific for a given species, type, strain or mutant or polymorphism.

The practical implications of the detection system according to the present invention are also important. While the principles described in detail herein have been demonstrated using PCR for amplification, readouts can be engaged via any methodology known in the art. With the current emphasis on microarray detection systems, one would be able to detect a far greater range of microorganisms using genomically simplified DNA since the bisulfite treatment reduces the genomic complexity and hence allows for more classes of micro organisms to be tested on microarrays with a smaller number of detectors (features).

If for example a microarray was to be constructed to detect 250,000 or so different microorganisms in one test, current methodology could not provide an adequate pragmatic detection platform, as it would be swamped by physical limitations of the detector platform. However, with genomic simplification, a small microarray could detect 1000 or so different high level bacterial categories. The positives from such a test could then be evaluated using another array, simply containing representatives of those groups that were positive in the initial test.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method for obtaining a microbial specific nucleic acid of a microbial genome or microbial nucleic acid comprising:

reducing the complexity of the microbial genome or a microbial nucleic acid by generating a derivative or simplified microbial genome or a derivative or simplified microbial nucleic acid in which substantially all of the positions naturally occupied by cytosines are occupied by uracil in said derivative microbial genome or said derivative microbial nucleic acid or in which substantially all of the positions naturally occupied by cytosine are replaced by thymine in said simplified microbial genome or simplified microbial nucleic acid such that said derivative or simplified microbial genome or derivative or simplified microbial nucleic acid has a nucleotide sequence which is not found in a microbial genome or said microbial nucleic acid in which substantially all of the positions naturally occupied by cytosines have not been occupied by uracil or thymine; and obtaining a microbial specific nucleic acid from the derivative or simplified microbial genome or derivative or simplified microbial nucleic acid, wherein said microbial-specific nucleic acid comprises at least a portion of said derivative or simplified microbial genome or said derivative or simplified microbial nucleic acid.

2. The method according to claim 1 comprising converting microbial RNA to DNA prior to carrying out the method.

3. The method according to claim 1 comprising carrying out the method on microbial RNA to yield a derivative RNA molecule then converting the derivative RNA to DNA.

4. The method according to claim 1 wherein substantially all of the positions naturally occupied by cytosine have been occupied by uracil.

5. The method according to claim 1 wherein substantially all of the positions naturally occupied by cytosine have been occupied by thymine.

6. The method according to claim 1 wherein the microbial genome or microbial nucleic acid is treated with an agent selected from the group consisting of bisulphite, acetate and citrate that modifies cytosine to uracil.

7. The method according to claim 1 wherein the microbial genome or microbial nucleic acid is treated with an agent selected from the group consisting of bisulphite, acetate and citrate that modifies cytosine to uracil; and wherein said method further comprises amplifying the derivative microbial genome or the derivative microbial nucleic acid to produce a microbial genome or microbial nucleic acid having a reduced complexity.

8. The method according to claim 7 wherein amplification is carried out by polymerase chain reaction (PCR), isothermal amplification, or signal amplification.

9. The method according to claim 6 wherein the agent is sodium bisulphite.

10. The method according to claim 1 wherein the microbial specific nucleic acid comprises one or more nucleotide sequences unique to a microorganism.

11. The method according to claim 1 wherein the microbial genome or microbial nucleic acid is obtained from a phage, virus, viroid, bacterium, fungus, alga, protozoan, spirochaete, or single cell organism.

12. The method according to claim 1 wherein the microbial genome or microbial nucleic acid is from a prokaryote or single celled eukaryotic microorganism and is selected from the group consisting of a protein encoding nucleic acid, non-protein encoding nucleic acid, and ribosomal gene regions.

13. The method according to claim 12 wherein the ribosomal gene regions are 16S or 23S in prokaryotes and 18S or 28S in single celled eukaryotic microorganisms.

14. A method for obtaining or identifying a microbial specific nucleic acid sequence of a microbial genome or microbial nucleic acid comprising:
    obtaining the nucleic acid sequence of the microbial genome or microbial nucleic acid;
    reducing the base complexity of the nucleic acid sequence by changing substantially all cytosines in the sequence to thymine to form a simplified nucleic acid sequence containing substantially only bases selected from adenine (A), guanine (G) and thymine (T) such that said simplified nucleic acid has a nucleotide sequence which is not found in said microbial genome or said microbial nucleic acid in which substantially all of the cytosines have not been changed to thymine; and
    obtaining or identifying a microbial specific nucleic acid sequence from the simplified nucleic acid sequence, wherein said microbial-specific nucleic acid comprises at least a portion of said simplified nucleic acid.

15. The method according to claim 14 wherein said microbial specific nucleic acid sequence contains one or more sequences unique to a microorganism.

16. The method according to claim 14 wherein the microbial genome or nucleic acid is obtained from a phage, virus, viroid, bacterium, fungus, alga, protozoan, spirochaete, or single cell organism.

17. The method according to claim 14 wherein the microbial genome or microbial nucleic acid is from a prokaryote or single celled eukaryotic microorganism and is selected from the group consisting of a protein encoding nucleic acid, non-protein encoding nucleic acid, and ribosomal gene regions.

18. The method according to claim 17 wherein the ribosomal gene regions are 16S or 23S in prokaryotes and 18S or 28S in single celled eukaryotic microorganisms.

19. A method for simplification of a microbial nucleic acid comprising:
    treating microbial nucleic acid from a ribosomal gene region of a prokaryote or a single celled eukaryotic microorganism with an agent that modifies cytosine to uracil to form derivative microbial nucleic acid such that said derivative microbial nucleic acid has a nucleotide sequence which is not found in said ribosomal gene region which has not been treated with said agent; and
    producing a simplified form of the microbial genome or nucleic acid by amplifying said derivative microbial nucleic acid.

20. The method according to claim 19 wherein the ribosomal gene region is 16S or 23S in a prokaryote or 18S or 28S in single celled eukaryotic microorganism.

21. The method according to claim 19 wherein the agent is selected from the group consisting of bisulphite, acetate and citrate.

22. The method according to claim 21 wherein the agent is sodium bisulphite.

23. The method according to claim 19 wherein the agent modifies a cytosine to a uracil in each strand of complementary double stranded microbial DNA forming two derivative but non-complementary microbial nucleic acid molecules.

24. The method according to claim 19 wherein the derivative microbial nucleic acid has a reduced total number of cytosines compared with the corresponding untreated microbial nucleic acid.

25. The method according to claim 19 wherein the simplified form of the microbial nucleic acid has a reduced total number of cytosines compared with the corresponding untreated microbial genome or nucleic acid.

26. The method according to claim 19 wherein the derivative microbial nucleic acid substantially contains bases adenine (A), guanine (G), thymine (T) and uracil (U) and has substantially the same total number of bases as the corresponding untreated microbial nucleic acid.

27. The method according to claim 19 wherein the simplified form of the microbial nucleic acid is comprised substantially of bases adenine (A), guanine (G) and thymine (T).

28. The method according to claim 19, wherein amplification is carried out by polymerase chain reaction (PCR), isothermal amplification, or signal amplification.

29. A method for producing a microbial-specific nucleic acid molecule comprising:
    treating a sample containing microbial derived DNA with an agent that modifies cytosine to uracil to form derivative microbial nucleic acid such that said derivative microbial nucleic acid has a nucleotide sequence which is not found in said microbial derived DNA which has not been treated with said agent; and
    producing a simplified nucleic acid molecule by amplifying at least part of the derivative microbial nucleic acid, the simplified nucleic acid molecule having a reduced total number of cytosines compared with the corresponding untreated microbial nucleic acid wherein said simplified nucleic acid molecule comprises at least a portion of said derivative microbial nucleic acid and wherein the simplified nucleic acid molecule includes a nucleic acid sequence specific for a microorganism or microorganism type.

30. The method according to claim 29 wherein the microorganism is selected from the group consisting of a phage, virus, viroid, bacterium, fungus, alga, protozoan, spirochaete and single cell organism.

31. The method according to claim 29 wherein the microbial nucleic acid is from a prokaryote or single celled eukaryotic microorganism and is selected from the group consisting of protein encoding nucleic acid, non-protein encoding nucleic acid, and ribosomal gene regions.

32. The method according to claim 31 wherein the ribosomal gene regions are 16S or 23S in prokaryotes and 18S or 28S in single celled eukaryotic microorganisms.

33. The method according to claim 29 wherein the agent modifies unmethylated cytosine.

34. The method according to claim 29 wherein the agent is selected from the group consisting of bisulphite, acetate and citrate.

35. The method according to claim 34 wherein the agent is sodium bisulphite.

36. The method according to claim 29 wherein amplification is carried out by polymerase chain reaction (PCR), isothermal amplification, or signal amplification.

37. The method according to claim 29 further comprising:
    detecting the microbial-specific nucleic acid molecule.

38. The method according to claim 37 wherein the microbial-specific nucleic acid molecule is detected by real-time PCR.

39. The method according to claim 37 wherein the microbial-specific nucleic acid molecule is detected by a microarray detection system.

40. The method according to claim 37 wherein the microbial-specific nucleic acid molecule is detected by:
providing a detector ligand capable of binding to a target region of the microbial-specific nucleic acid molecule and allowing sufficient time for the detector ligand to bind to the target region; and
measuring binding of the detector ligand to the target region to detect the presence of the microbial-specific nucleic acid molecule.

41. The method according to claim 40 wherein the microbial-specific nucleic acid molecule is detected by separating an amplification product and visualising the separated product.

42. The method according to claim 41 wherein the amplification product is separated by electrophoresis and detected by visualising one or more bands on a gel.

43. The method according to claim 29 wherein the simplified nucleic acid molecule has substantially no cytosines.

44. The method according to claim 43 wherein the microbial-specific nucleic acid molecule does not occur naturally in the microorganism.

45. The method according to claim 29 wherein the microbial-specific nucleic acid molecule has a nucleic acid sequence indicative of a taxonomic level of the microorganism.

46. The method according to claim 45 wherein the taxonomic level of the microorganism includes family, genus, species, strain, type, or different populations from the same or different geographic or benthic populations.

47. A method for selecting a sequence of a microbial-specific nucleic acid molecule comprising:
obtaining a DNA sequence from a microorganism;
forming a simplified form of the microbial DNA sequence by carrying out a conversion of the microbial DNA sequence by changing substantially all cytosines to thymine such that the sequence of the simplified form of the microbial DNA comprises substantially bases adenine, guanine and thymine and such that said simplified form of the microbial DNA sequence has a nucleotide sequence which is not found in said microbial DNA sequence in which substantially all cytosines have not been converted to thymine, wherein the conversion mimics the action of an agent that converts cytosine to uracil; and
selecting a microbial-specific nucleic acid sequence from the simplified form of the microbial DNA sequence.

48. The method according to claim 47 wherein the conversion is carried out in silico.

49. The method according to claim 47 wherein simplified forms of two or more microbial DNA sequences are obtained and the two or more sequences are compared to obtain at least one microbial-specific nucleic acid molecule.

50. A method for detecting the presence of a microorganism in a sample comprising:
treating a microbial nucleic acid with an agent that modifies cytosine to uracil to form derivative microbial nucleic acid;
providing primers capable of allowing amplification of a desired microbial-specific nucleic acid molecule to the derivative microbial nucleic acid, wherein said desired microbial-specific nucleic acid comprises at least a portion of said derivative microbial nucleic acid;
carrying out an amplification reaction on the derivative microbial nucleic acid to generate an amplification product having a nucleotide sequence which is not found in a microbial genome which has not been treated with said agent; and
assaying for the presence of said amplification product containing the desired microbial-specific nucleic acid molecule, wherein detection of the desired microbial-specific nucleic acid molecule is indicative of the presence of the microorganism.

51. The method according to claim 50 wherein the microorganism is selected from the group consisting of a phage, virus, viroid, bacterium, fungus, alga, protozoan, spirochaete and single cell organism.

52. The method according to claim 50 wherein the agent is selected from the group consisting of bisulphite, acetate and citrate.

53. The method according to claim 52 wherein the agent is sodium bisulphite.

54. The method according to claim 50 wherein amplification is carried out by polymerase chain reaction (PCR), isothermal amplification, or signal amplification.

55. The method according to claim 50 wherein the microbial-specific nucleic acid molecule is detected by real-time PCR.

56. The method according to claim 50 wherein the microbial-specific nucleic acid molecule is detected by a microarray detection system.

57. The method according to claim 50 wherein the microbial-specific nucleic acid molecule is detected by:
providing a detector ligand capable of binding to a region of the microbial-specific nucleic acid molecule and allowing sufficient time for the detector ligand to bind to the region; and
measuring binding of the detector ligand to the microbial-specific nucleic acid molecule to detect the presence of the microbial-specific nucleic acid molecule.

58. The method according to claim 50 wherein the microbial-specific nucleic acid molecule is detected by separating an amplification product and visualising the separated product.

59. The method according to claim 7 wherein the agent is sodium bisulphite.

60. The method according to claim 8 wherein the agent is sodium bisulphite.

61. The method according to claim 51 wherein the microorganism is a virus.

62. The method according to claim 51 wherein the microorganism is a bacterium.

63. The method according to claim 50, wherein the amplification product does not encode a polypeptide which is encoded by the corresponding region of microbial nucleic acid which has not been treated with said agent.

* * * * *